US006358956B1

(12) United States Patent
Hartman et al.

(10) Patent No.: US 6,358,956 B1
(45) Date of Patent: Mar. 19, 2002

(54) INHIBITORS OF PRENYL-PROTEIN TRANSFERASE

(75) Inventors: George D. Hartman, Lansdale; William C. Lumma, Jr., Pennsburg; John T. Sisko, Lansdale; Anthony M. Smith, Green Lane; Thomas J. Tucker, North Wales; Gerald E. Stokker, Gwynedd Valley, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/516,750

(22) Filed: Mar. 1, 2000

Related U.S. Application Data

(60) Provisional application No. 60/127,253, filed on Mar. 31, 1999, and provisional application No. 60/122,768, filed on Mar. 3, 1999.

(51) Int. Cl.$^7$ ............... A06L 31/295; A07D 241/01; A07D 233/00; A07D 233/54; A07D 403/00
(52) U.S. Cl. ............... 514/252.13; 544/379; 544/358; 544/366; 544/389; 544/391; 548/311.1; 548/314.7
(58) Field of Search .............. 514/252.13; 544/379, 544/358, 366, 383, 389, 391; 548/311.1, 314.7

(56) References Cited

U.S. PATENT DOCUMENTS

| | | | |
|---|---|---|---|
| 3,328,396 A | 6/1967 | Kirchner et al. ............. | 260/243 |
| 3,331,830 A | 7/1967 | Tomcufcik et al. .......... | 260/154 |
| 4,663,641 A | 5/1987 | Iiyamaa et al. .............. | 346/204 |
| 4,829,065 A | 5/1989 | Pascal et al. ................. | 514/255 |
| 5,219,856 A | 6/1993 | Olson ........................... | 514/252 |
| 5,340,809 A | 8/1994 | Gaudry et al. ............... | 514/252 |
| 5,384,319 A | 1/1995 | Ferrini ....................... | 514/227.8 |
| 5,478,934 A | 12/1995 | Yuan et al. .................. | 540/546 |
| 5,856,326 A | 1/1999 | Anthony et al. ............. | 514/252 |

FOREIGN PATENT DOCUMENTS

| | | |
|---|---|---|
| BE | 820242 | 1/1975 |
| EP | 0 318 235 | 11/1988 |
| EP | 0 441 226 A1 | 8/1991 |
| EP | 441226 | * 10/1996 |
| JP | S51-141831 | 5/1975 |
| WO | WO 95/34311 | 12/1995 |
| WO | 9630343 | * 10/1996 |
| WO | WO96/31501 | 10/1996 |
| WO | WO 97/36592 | 10/1997 |
| WO | WO 98/57954 | 12/1998 |
| WO | WO99/09985 | 3/1999 |

OTHER PUBLICATIONS

Lerner, et al., Disruption of Oncogenic K–Ras4B Processing and Signaling by a Potent Geranylgeranyltransferase I Inhibitor, Nov. 1995, The Journal of Biological Chemistry, vol. 210 No. 45, pp. 26770–26773.

Miquel, et al., GGTI–298 Induces G0–G1 Block and Apaptosis Whereas FTI–277 Causes G2–M Enrichment in A549 Cells, May 1997, Cancer Research, vol. 57, pp. 1846–1850.

Moores, et al., Sequence Dependence of Protein Isoprenylation, Aug. 1991, The Journal of Biological Chemistry, vol. 266, No. 22, pp. 14603–14610.

McGuire, et al., Platelet–derived Growth Factor Receptor Tyrosine Phosphorylation Requires Protein Geranylgeranylation but not Farnesylation, Nov. 1996, The Journal of Biological Chemistry, vol. 271, pp. 27402–27407.

Orjales, et al., Synthesis and Structure–Activity Relationship of New Piperdinyl and Piperazinyl Derivatives as Antiallergies, May–Jun. 1995, Journal of Heterocyclic Chemistry, vol. 32, No. 3, pp. 707–718.

Sepp–Lorenzino, et al., A Peptidomimetic Inhibitor of Farnesyl:Protein Transferase Blocks the Anchorage–dependant and –independent Growth of Human Tumor Cell Lines, Nov. 1995, Cancer Research, vol. 55, pp. 5302–5309.

Kohl, et al., Inhibition of farnesyltransferase induces regression of mammary and salivary carcinomas in ras transgenic mice, Aug. 1995, Nature Medicine, vol. 1, No. 8, pp. 792–797.

Kohl, et al., Protein farnesyltransferase inhibitors block the growth of ras–dependent tumors in nude mice, Sep. 1994, Porc. Natl. Acad. Sci. USA, vol. 91, pp. 9141–9145.

Kohl, et al., Selective Inhibition of ras–Dependent Transformation by a Farnesyltransferase Inhibitor, Jun. 25, 1993, Science, vol. 260, pp. 1934–1937.

James, et al., Polylsine and CVIM Sequences of K–RasB Dictate Specificity of Prenylation and Confer Resistance to Benzodiazepine Peptidomimetic inVitro, Mar. 17, 1995, The Journal of Biological Chemistry, vol. 270, No. 11, pp. 6221–6226.

James, et al., Benzodiazepine Peptidomimetic BZA–5B Interrupts the MAP Kinase Activation Pathway in H–Ras–transformed Rat–1 Cells, but Not in Untransformed Cells, Nov. 4, 1994, The Journal of Biological Chemistry, vol. 269, No. 44, pp. 27706–27714.

Gibbs, et al., Selective Inhibition of Farnesyl–Protein Transferase Blocks Ras Processing In Vivo, Apr. 1993, The Journal of Biological Chemistry, vol. 268, No. 11, pp. 7617–7620.

Graham, et al., Inhibitors of protein farnesylation, 1996, Exp. Opin. Ther. Patents 6(12):1295–1304.

(List continued on next page.)

Primary Examiner—Mukund J. Shah
Assistant Examiner—Sudhaker B. Patel
(74) Attorney, Agent, or Firm—David A. Muthard; Mark R. Daniel

(57) ABSTRACT

The present invention comprises piperazine-containing compounds which inhibit prenyl-protein transferases, including-farnesyl-protein transferase and geranylgeranyl-protein transferase type I. Such therapeutic compounds are useful in the treatment of cancer.

22 Claims, No Drawings

OTHER PUBLICATIONS

Graham, Inhibitors of protein farnesylation: a new approach to cancer chemotherapy, 1995, Exp. Opin. Ther. Patents 5(12):1269–1285.

Carceller, et al., (Pyridylcyanomethyl)piperazines as Orally Active PAF Antagonists, 1992, Journal of Medicinal Chemistry, vol. 35, pp. 4118–4134.

CA 109: 231076q, (Imidazolylalkyl)piperazine derivatives as platelet aggregation inhibitors, T. Komoto, et al.

Sajiki, et al., The Formation of a Novel Pd/C–Ethlenediamine Complex Catalyst: Chemoselective Hydrogenation without Deprotection of the O –Benzyl and N –Cbz Groups, 1991, J. Org. Chem., vol. 63, No. 22, pp. 7990–7992.

* cited by examiner

SEQUENCE LISTING

<160> NUMBER OF SEQ ID NOS: 21

<210> SEQ ID NO 1
<211> LENGTH: 4
<212> TYPE: PRT
<213> ORGANISM: Artificial Sequence
<220> FEATURE:
<223> OTHER INFORMATION: completely synthetic sequence

<400> SEQUENCE: 1

Cys Val Leu Ser
 1

<210> SEQ ID NO 2
<211> LENGTH: 15
<212> TYPE: PRT
<213> ORGANISM: Artificial Sequence
<220> FEATURE:
<223> OTHER INFORMATION: completely synthetic sequence

<400> SEQUENCE: 2

Gly Lys Lys Lys Lys Lys Ser Lys Thr Lys Cys Val Ile Met
 1               5                  10                  15

<210> SEQ ID NO 3
<211> LENGTH: 52
<212> TYPE: DNA
<213> ORGANISM: Artificial Sequence
<220> FEATURE:
<223> OTHER INFORMATION: completely synthetic sequence

<400> SEQUENCE: 3
gagagggaat tcgggccctt cctgcatgct gctgctgctg ctgctgctgg gc        52

<210> SEQ ID NO 4
<211> LENGTH: 41
<212> TYPE: DNA
<213> ORGANISM: Artificial Sequence
<220> FEATURE:
<223> OTHER INFORMATION: completely synthetic sequence

<400> SEQUENCE: 4
gagagagctc gaggttaacc cgggtgcgcg gcgtcggtgg t                    41

<210> SEQ ID NO 5
<211> LENGTH: 42
<212> TYPE: DNA
<213> ORGANISM: Artificial Sequence
<220> FEATURE:
<223> OTHER INFORMATION: completely synthetic sequence

<400> SEQUENCE: 5
gagagagtct agagttaacc cgtggtcccc gcgttgcttc ct                   42

<210> SEQ ID NO 6
<211> LENGTH: 43
<212> TYPE: DNA
<213> ORGANISM: Artificial Sequence
<220> FEATURE:
<223> OTHER INFORMATION: completely synthetic sequence

<400> SEQUENCE: 6
gaagaggaag cttggtaccg ccactgggct gtaggtggtg gct                  43

<210> SEQ ID NO 7
<211> LENGTH: 27
<212> TYPE: DNA
<213> ORGANISM: Artificial Sequence
<220> FEATURE:
<223> OTHER INFORMATION: completely synthetic sequence

<400> SEQUENCE: 7
ggcagagctc gtttagtgaa ccgtcag                                27

<210> SEQ ID NO 8
<211> LENGTH: 27
<212> TYPE: DNA
<213> ORGANISM: Artificial Sequence
<220> FEATURE:
<223> OTHER INFORMATION: completely synthetic sequence

<400> SEQUENCE: 8
gagagatctc aaggacggtg actgcag                                27

<210> SEQ ID NO 9
<211> LENGTH: 86
<212> TYPE: DNA
<213> ORGANISM: Artificial Sequence
<220> FEATURE:
<223> OTHER INFORMATION: completely synthetic sequence

<400> SEQUENCE: 9
tctcctcgag gccaccatgg ggagtagcaa gagcaagcct aaggacccca gccagcgccg    60
gatgacagaa tacaagcttg tggtgg                                 86

<210> SEQ ID NO 10
<211> LENGTH: 33
<212> TYPE: DNA
<213> ORGANISM: Artificial Sequence
<220> FEATURE:
<223> OTHER INFORMATION: completely synthetic sequence

<400> SEQUENCE: 10
cacatctaga tcaggacagc acagacttgc agc                         33

<210> SEQ ID NO 11
<211> LENGTH: 41
<212> TYPE: DNA
<213> ORGANISM: Artificial Sequence
<220> FEATURE:
<223> OTHER INFORMATION: completely synthetic sequence

<400> SEQUENCE: 11
tctcctcgag gccaccatga cagaatacaa gcttgtggtg g                41

<210> SEQ ID NO 12
<211> LENGTH: 38
<212> TYPE: DNA
<213> ORGANISM: Artificial Sequence
<220> FEATURE:
<223> OTHER INFORMATION: completely synthetic sequence

<400> SEQUENCE: 12
cactctagac tggtgtcaga gcagcacaca cttgcagc                    38

<210> SEQ ID NO 13
<211> LENGTH: 38
<212> TYPE: DNA
<213> ORGANISM: Artificial Sequence
<220> FEATURE:

<223> OTHER INFORMATION: completely synthetic sequence

<400> SEQUENCE: 13
gagagaattc gccaccatga cggaatataa gctggtgg        38

<210> SEQ ID NO 14
<211> LENGTH: 33
<212> TYPE: DNA
<213> ORGANISM: Artificial Sequence
<220> FEATURE:
<223> OTHER INFORMATION: completely synthetic sequence

<400> SEQUENCE: 14
gagagtcgac gcgtcaggag agcacacact tgc        33

<210> SEQ ID NO 15
<211> LENGTH: 22
<212> TYPE: DNA
<213> ORGANISM: Artificial Sequence
<220> FEATURE:
<223> OTHER INFORMATION: completely synthetic sequence

<400> SEQUENCE: 15
ccgccggcct ggaggagtac ag        22

<210> SEQ ID NO 16
<211> LENGTH: 38
<212> TYPE: DNA
<213> ORGANISM: Artificial Sequence
<220> FEATURE:
<223> OTHER INFORMATION: completely synthetic sequence

<400> SEQUENCE: 16
gagagaattc gccaccatga ctgagtacaa actggtgg        38

<210> SEQ ID NO 17
<211> LENGTH: 32
<212> TYPE: DNA
<213> ORGANISM: Artificial Sequence
<220> FEATURE:
<223> OTHER INFORMATION: completely synthetic sequence

<400> SEQUENCE: 17
gagagtcgac ttgttacatc accacacatg gc        32

<210> SEQ ID NO 18
<211> LENGTH: 21
<212> TYPE: DNA
<213> ORGANISM: Artificial Sequence
<220> FEATURE:
<223> OTHER INFORMATION: completely synthetic sequence

<400> SEQUENCE: 18
gttggagcag ttggtgttgg g        21

<210> SEQ ID NO 19
<211> LENGTH: 38
<212> TYPE: DNA
<213> ORGANISM: Artificial Sequence
<220> FEATURE:
<223> OTHER INFORMATION: completely synthetic sequence

<400> SEQUENCE: 19
gagaggtacc gccaccatga ctgaatataa acttgtgg        38

-continued

```
<210> SEQ ID NO 20
<211> LENGTH: 36
<212> TYPE: DNA
<213> ORGANISM: Artificial Sequence
<220> FEATURE:
<223> OTHER INFORMATION: completely synthetic sequence

<400> SEQUENCE: 20
ctctgtcgac gtatttacat aattacacac tttgtc                36

<210> SEQ ID NO 21
<211> LENGTH: 24
<212> TYPE: DNA
<213> ORGANISM: Artificial Sequence
<220> FEATURE:
<223> OTHER INFORMATION: completely synthetic sequence

<400> SEQUENCE: 21
gtagttggag ctgttggcgt aggc                             24
```

INHIBITORS OF PRENYL-PROTEIN TRANSFERASE

RELATED APPLICATION

The present patent application is a continuation-in-part application of copending provisional application Ser. No. 60/127,253, filed Mar. 31, 1999, and copending provisional application Ser. No. 60/122,768, filed Mar. 3, 1999.

BACKGROUND OF THE INVENTION

The present invention relates to certain compounds that are useful for the inhibition of prenyl-protein transferases and the treatment of cancer. In particular, the invention relates to prenyl-protein transferase inhibitors which are efficacious in vivo as inhibitors of geranylgeranyl-protein transferase type I (GGTase-I) and that inhibit the cellular processing of both the H-Ras protein and the K4B-Ras protein.

Prenylation of proteins by prenyl-protein transferases represents a class of post-translational modification (Glomset, J. A., Gelb, M. H., and Farnsworth, C. C. (1990). Trends Biochem. Sci. 15, 139–142; Maltese, W. A. (1990). FASEB J. 4, 3319–3328). This modification typically is required for the membrane localization and function of these proteins. Prenylated proteins share characteristic C-terminal sequences including CAAX (C, Cys; A, an aliphatic amino acid; X, another amino acid), XXCC, or XCXC. Three post-translational processing steps have been described for proteins having a C-terminal CAAX sequence: addition of either a 15 carbon (farnesyl) or 20 carbon (geranylgeranyl) isoprenoid to the Cys residue, proteolytic cleavage of the last 3 amino acids, and methylation of the new C-terminal carboxylate (Cox, A. D. and Der, C. J. (1992a). Critical Rev. Oncogenesis 3:365–400; Newman, C. M. H. and Magee, A. I. (1993). Biochim. Biophys. Acta 1155:79–96). Some proteins may also have a fourth modification: almitoylation of one or two Cys residues N-terminal to the farnesylated Cys. While some mammalian cell proteins terminating in XCXC are carboxymethylated, it is not clear whether carboxy methylation follows prenylation of proteins terminat-ing with a XXCC motif (Clarke, S. (1992). Annu. Rev. Biochem. 61, 355–386). For all of the prenylated proteins, addition of the isoprenoid is the first step and is required for the subsequent steps (Cox, A. D. and Der, C. J. (1992a). Critical Rev. Oncogenesis 3:365–400; Cox, A. D. and Der, C. J. (1992b) Current Opinion Cell Biol. 4:1008–1016).

Three enzymes have been described that catalyze protein prenylation: farnesyl-protein transferase (FPTase), geranylgeranyl-protein transferase type I (GGPTase-I), and geranylgeranyl-protein transferase type-II (GGPTase-II, also called Rab GGPTase). These enzymes are found in both yeast and mammalian cells (Clarke, 1992; Schafer, W. R. and Rine, J. (1992) Annu. Rev. Genet. 30:209–237). Each of these enzymes selectively uses farnesyl diphosphate or geranyl-geranyl diphosphate as the isoprenoid donor and selectively recognizes the protein substrate. FPTase farnesylates CaaX-containing proteins that end with Ser, Met, Cys, Gln or Ala. For FPTase, CaaX tetrapeptides comprise the minimum region required for interaction of the protein substrate with the enzyme. The enzymological characterization of these three enzymes has demonstrated that it is possible to selectively inhibit one with little inhibitory effect on the others (Moores, S. L., Schaber, M. D., Mosser, S. D., Rands, E., O'Hara, M. B., Garsky, V. M., Marshall, M. S., Pompliano, D. L., and Gibbs, J. B., J. Biol. Chem., 266:17438 (1991), U.S. Pat. No. 5,470,832).

The prenylation reactions have been shown genetically to be essential for the function of a variety of proteins (Clarke, 1992; Cox and Der, 1992a; Gibbs, J. B. (1991). Cell 65: 1–4; Newman and Magee, 1993; Schafer and Rine, 1992). This requirement often is demonstrated by mutating the CaaX Cys acceptors so that the proteins can no longer be prenylated. The resulting proteins are devoid of their central biological activity. These studies provide a genetic "proof of principle" indicating that inhibitors of prenylation can alter the physiological responses regulated by prenylated proteins.

The Ras protein is part of a signaling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation, Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, Ann. Rev. Biochem. 62:851–891 (1993)). Activation of Ras leads to activation of multiple intracellular signal transduction pathways, including the MAP Kinase pathway and the Rho/Rac pathway (Joneson et al., Science 271:810–812).

Mutated ras genes are found in many human cancers, including colorectal carcinoma, exocrine pancreatic carcinoma, and myeloid leukemias. The protein products of these genes are defective in their GTPase activity and constitutively transmit a growth stimulatory signal.

The Ras protein is one of several proteins that are known to undergo post-translational modification. Farnesyl-protein transferase utilizes farnesyl pyrophosphate to covalently modify the Cys thiol group of the Ras CAAX box with a farnesyl group (Reiss et al., Cell, 62:81–88 (1990); Schaber et al., J. Biol. Chem., 265:14701–14704 (1990); Schafer et al., Science, 249:1133–1139 (1990); Manne et al., Proc. Natl. Acad. Sci USA, 87:7541–7545 (1990)).

Ras must be localized to the plasma membrane for both normal and oncogenic functions. At least 3 post-ranslational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., Nature 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., Ann. Rev. Biochem. 61:355–386 (1992); W. R. Schafer and J. Rine, Ann. Rev. Genetics 30:209–237 (1992)). Direct inhibition of farnesyl-protein transferase would be more specific and attended by fewer side effects than would occur with the required dose of a general inhibitor of isoprene biosynthesis.

Other farnesylated proteins include the Ras-related GTP-binding proteins such as RhoB, fungal mating factors, the nuclear lamins, and the gamma subunit of transducin. James, et al., J. Biol. Chem. 269, 14182 (1994) have identified a peroxisome associated protein Pxf which is also farnesylated. James, et al., have also suggested that there are farnesylated proteins of unknown structure and function in addition to those listed above. Inhibitors of farnesyl-protein transferase (FPTase) have been described in two general classes. The first class includes analogs of farnesyl diphosphate (FPP), while the second is related to protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., PNAS, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., Science, 260:1934–1937 (1993); Graham, et al., J. Med. Chem., 37, 725 (1994)).

Mammalian cells express four types of Ras proteins (H-, N-, K4A-, and K4B-Ras) among which K4B-Ras is the most frequently mutated form of Ras in human cancers. The genes that encode these proteins are abbreviated H-ras, N-ras, K4A-ras and K4B-ras respectively. H-ras is an abbreviation for Harvey-ras. K4A-ras and K4B-ras are abbreviations for the Kirsten splice variants of ras that contain the 4A and 4B exons, respectively. Inhibition of farnesyl-protein transferase has been shown to block the growth of H-ras-transformed cells in soft agar and to modify other aspects of their transformed phenotype. It has also been demonstrated that certain inhibitors of farnesyl-protein transferase selectively block the processing of the H-Ras oncoprotein intracellularly (N. E. Kohl et al., Science, 260:1934–1937 (1993) and G. L. James et al., Science, 260:1937–1942 (1993). Recently, it has been shown that an inhibitor of farnesyl-protein transferase blocks the growth of H-ras-dependent tumors in nude mice (N. E. Kohl et al., Proc. Natl. Acad. Sci U.S.A., 91:9141–9145 (1994) and induces regression of mammary and salivary carcinomas in H-ras transgenic mice (N. E. Kohl et al., Nature Medicine, 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., Science 245:379 (1989)). These drugs inhibit HMG-CoA reductase, the rate limiting enzyme for the production of polyisoprenoids including farnesyl pyrophosphate. Inhibition of farnesyl pyrophosphate biosynthesis by inhibiting HMG-CoA reductase blocks Ras membrane localization in cultured cells.

It has been disclosed that the lysine-rich region and terminal CVIM sequence of the C-terminus of K-RasB confer resist-ance to inhibition of the cellular processing of that protein by certain selective FPTase inhibitors. (James, et al., J. Biol. Chem. 270, 6221 (1995) Those FPTase inhibitors were effective in inhibiting the processing of H-Ras proteins. James et al. suggested that prenylation of the K4B-Ras protein by GGTase-I contributed to the resistance to the selective FPTase inhibitors. Selective inhibitors of GGTase-I have been previously disclosed (see for example U.S. Pat. No. 5,470,832, issued Nov. 28, 1995). Other compounds have been described as selective inhibitors of GGTase-I (see for example PCT Publication No. WO 96/21456). Combinations of a selective inhibitor of FPTase and a selective inhibitor of GGTase-I have been disclosed as useful in the treatment of cancer (PCT Publication No. WO 97/34664).

Several groups of scientists have recently disclosed compounds that are non-selective FPTase/GGTase-I inhibitors. (Nagasu et al. Cancer Research, 55:5310–5314 (1995); PCT application WO 95/25086).

It is the object of the instant invention to provide a prenyl-protein transferase inhibitor which is efficacious in vivo as an inhibitor of geranylgeranyl-protein transferase type I (GGTase-I), also known as CAAX GGTase.

It is also the object of the present invention to provide a compound which inhibits the cellular processing of both the H-Ras protein and the K4B-Ras protein.

It is also the object of the present invention to provide a compound which is efficacious in vivo as an inhibitor of the growth of cancer cells characterized by a mutated K4B-Ras protein.

A composition which comprises such an inhibitor compound is used in the present invention to treat cancer.

SUMMARY OF THE INVENTION

The present invention comprises piperazine-containing compounds which inhibit prenyl-protein transferases. Further contained in this invention are chemotherapeutic compositions containing these prenyl transferase inhibitors and methods for their production.

The compounds of this invention are illustrated by the formula A:

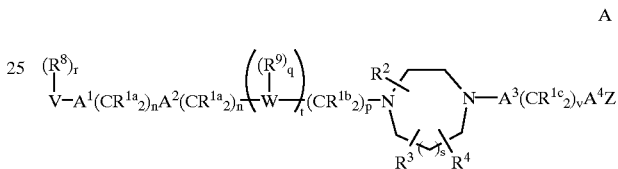

DETAILED DESCRIPTION OF THE INVENTION

The compounds of this invention are useful in the inhibition of prenyl-protein transferases and the prenylation of the oncogene protein Ras. In a first embodiment of this invention, the inhibitors of prenyl-protein transferases are illustrated by the formula A:

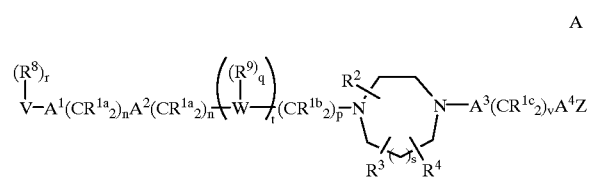

wherein:

$R^{1a}$ and $R^{1b}$ are independently selected from:
a) hydrogen,
b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $R^{10}NC(O)$—, $(R^{10})_2NC(O)$—, $R^{10}{}_2N$—C$(NR^{10})$—, CN, $NO_2$, $R^{10}C(O)$—, $N_3$, —$N(R^{10})_2$, or $R^{11}OC(O)NR^{10}$—,
c) unsubstituted or substituted $C_1$–$C_6$ alkyl wherein the substituent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2NC(O)$—, $R^{10}{}_2N$—C$(NR^{10})$—, CN, $R^{10}C(O)$—, $N_3$, —$N(R^{10})_2$, and $R^{11}OC(O)$—$NR^{10}$—;

$R^{1c}$ is independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$ or $R^{11}OC(O)NR^{10}$—, c) unsubstituted or substituted $C_1$–$C_6$ alkyl wherein the substituent on the substituted $C_1$–$C_6$ alkyl is selected from unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$ and $R^{11}OC(O)$—$NR^{10}$—;

or two $R^{1c}$s on the same carbon are combined with that carbon to form a $C_4$–$C_6$ cycloalkyl or $C_6$–$C_{10}$ multi-cyclic alkyl ring;

$R^2$ and $R^3$ are independently selected from: H; unsubstituted or substituted $C_{1-8}$ alkyl, unsubstituted or substituted $C_{2-8}$ alkenyl, unsubstituted or substituted $C_{2-8}$ alkynyl, unsubstituted or substituted aryl, unsubstituted or substituted heterocycle,

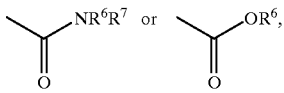

wherein the substituted group is substituted with one or more of:

1) aryl or heterocycle, unsubstituted or substituted with:
   a) $C_{1-4}$ alkyl,
   b) $(CH_2)_pOR^6$,
   c) $(CH_2)_pNR^6R^7$,
   d) halogen,
   e) CN,
   f) aryl or heteroaryl,
   g) perfluoro-$C_{1-4}$ alkyl,
   h) $SR^{6a}$, $S(O)R^{6a}$, $SO_2R^{6a}$,
2) $C_{3-6}$ cycloalkyl,
3) $OR^6$,
4) $SR^{6a}$, $S(O)R^{6a}$, or $SO_2R^{6a}$, 5) 

6) 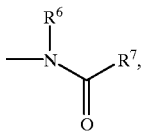

7) 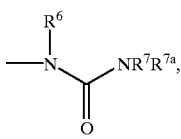

8) 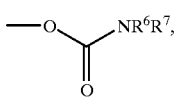

9) 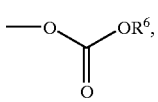

10) 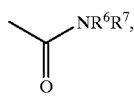

11) —$SO_2$—$NR^6R^7$,

12) 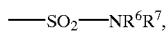

13) 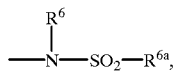

14) 

15) $N_3$,

16) F, or 17) perfluoro-$C_{1-4}$-alkyl; or $R^2$ and $R^3$ are attached to the same C atom and are combined to form —$(CH_2)_u$— wherein one of the carbon atoms is optionally replaced by a moiety selected from: O, $S(O)_m$, —$NC(O)$—, and —$N(COR^{10})$—;

$R^4$ is selected from H and $CH_3$; and any two of $R^2$, $R^3$ and $R^4$ are optionally attached to the same carbon atom;

$R^6$, $R^7$ and $R^{7a}$ are independently selected from: H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:

a) $C_{1-4}$ alkoxy,
b) aryl or heterocycle,
c) halogen,
d) HO,
e) 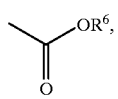

f) —$SO_2R^{11}$, or
g) $N(R^{10})_2$; or $R^6$ and $R^7$ may be joined in a ring;
$R^7$ and $R^{7a}$ may be joined in a ring;

$R^{6a}$ is selected from: $C_{1-4}$ alkyl, $C_{3-6}$ cycloalkyl, heterocycle, aryl, unsubstituted or substituted with:

a) $C_{1-4}$ alkoxy,
b) aryl or heterocycle,
c) halogen, d) HO, e) 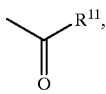

f) —SO$_2$R$^{11}$, or g) N(R$^{10}$)$_2$;

R$^8$ is independently selected from:

a) hydrogen, b) unsubstituted or substituted aryl, unsubstituted or substituted heterocycle, unsubstituted or substituted C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—, and c) C$_1$–C$_6$ alkyl unsubstituted or substituted by aryl, cyanophenyl, heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NH—, (R$^{10}$)$_2$NC(O)—, R$^{10}$$_2$N—C(NR$^{10}$)—, CN, R$^{10}$C(O)—, N$_3$, —N(R$^{10}$)$_2$, or R$^{10}$OC(O)NH—;

R$^9$ is selected from:

a) hydrogen, b) alkenyl, alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—, and c) C$_1$–C$_6$ alkyl unsubstituted or substituted by perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, N$_3$, —N(R$^{10}$)$_2$, or R$^{11}$OC(O)NR$^{10}$—;

R$^{10}$ is independently selected from hydrogen, C$_1$–C$_6$ alkyl, benzyl and aryl;

R$^{11}$ is independently selected from C$_1$–C$_6$ alkyl and aryl;

A$^1$ and A$^2$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

A$^3$ is selected from: —C(O)—, —C(O)NR$^{10}$—, —C(O)O—, and S(O)$_m$;

A$^4$ is selected from: a bond, O, and NR$^{10}$;

V is selected from:

a) hydrogen, b) heterocycle, c) aryl, d) C$_1$–C$_{20}$ alkyl wherein from 0 to 4 carbon atoms are replaced with a heteroatom selected from O, S, and N, and e) C$_2$–C$_{20}$ alkenyl, provided that V is not hydrogen if A$^1$ is S(O)$_m$ and V is not hydrogen if A$^1$ is a bond, n is 0 and A$^2$ is S(O)$_m$;

W is a heterocycle;

Z is unsubstituted or substituted aryl or unsubstituted or substituted heteroaryl;

m is 0, 1 or 2;

n is 0, 1, 2, 3 or 4;

p is 0, 1, 2, 3 or 4;

q is 1 or 2;

r is 0 to 5, provided that r is 0 when V is hydrogen;

s is 0 or 1;

t is 0 or 1;

u is 4 or 5; and v is 0, 1, 2 or 3; provided that v is not 0 if A$^3$ is —C(O)—or S(O)$_m$;

or the pharmaceutically acceptable salts thereof.

In a preferred embodiment of this invention, the inhibitors of prenyl-protein transferase are illustrated by the formula A:

$$\text{(R}^8\text{)}_r\text{—V—A}^1\text{(CR}^{1a}\text{}_2\text{)}_n\text{A}^2\text{(CR}^{1a}\text{}_2\text{)}_n\text{—(R}^9\text{)}_q\text{—W—(CR}^{1b}\text{}_2\text{)}_p\text{—N}\begin{pmatrix}R^2\\R^3\end{pmatrix}\begin{pmatrix}\\R^4\end{pmatrix}_s\text{N—A}^3\text{(CR}^{1c}\text{}_2\text{)}_v\text{A}^4\text{Z}$$

A wherein:

R$^{1a}$ is independently selected from: hydrogen or C$_1$–C$_6$ alkyl;

R$^{1b}$ is independently selected from:

a) hydrogen, b) aryl, heterocycle, cycloalkyl, CN, R$^{10}$O—, R$^{10}$NC(O)—, —N(R$^{10}$)$_2$ or C$_2$–C$_6$ alkenyl, c) unsubstituted or substituted C$_1$–C$_6$ alkyl wherein the substituent on the substituted C$_1$–C$_6$ alkyl is selected from unsubstituted or substituted aryl, heterocycle, cycloalkyl, alkenyl, R$^{10}$O— and —N(R$^{10}$)$_2$;

R$^{1c}$ is independently selected from:

a) hydrogen, b) C$_3$–C$_{10}$ cycloalkyl, R$^{10}$O—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$ or R$^{11}$OC(O)NR$^{10}$—, c) unsubstituted or substituted C$_1$–C$_6$ alkyl wherein the substituent on the substituted C$_1$–C$_6$ alkyl is selected from R$^{10}$O—, R$^{10}$C(O)NR$^{10}$—, (R$^{10}$)$_2$NC(O)—, R$^{10}$$_2$N—C(NR$^{10}$)—, CN, R$^{10}$C(O)—, N$_3$, —N(R$^{10}$)$_2$ and R$^{11}$OC(O)—NR$^{10}$—;or two R$^{1c}$s on the same carbon are combined with that carbon to form a C$_4$–C$_6$ cycloalkyl or C$_6$–C$_{10}$ multicyclic alkyl ring;

R$^3$ and R$^4$ are independently selected from H and CH$_3$;

R$^2$ is H;

$$\begin{matrix}\text{NR}^6\text{R}^7;\\\|\\\text{O}\end{matrix}\quad\begin{matrix}\text{OR}^6;\\\|\\\text{O}\end{matrix}$$

or C$_{1-5}$ alkyl, unbranched or branched, unsubstituted or substituted with one or more of:

1) aryl, 2) heterocycle,

3) OR$^6$,

4) SR$^{6a}$, SO$_2$R$^{6a}$, or

5)

$$\begin{matrix}\text{NR}^6\text{R}^7;\\\|\\\text{O}\end{matrix}$$

and any two of R$^2$, R$^3$, R$^4$, and R$^5$ are optionally attached to the same carbon atom;

R$^6$ and R$^7$ are independently selected from: H; C$_{1-4}$ alkyl, C$_{3-6}$ cycloalkyl, aryl, heterocycle, unsubstituted or substituted with:

a) $C_{1-4}$ alkoxy,
b) halogen, or
c) aryl or heterocycle;

$R^{6a}$ is selected from: $C_{1-4}$ alkyl or $C_{3-6}$ cycloalkyl, unsubstituted or substituted with:
a) $C_{1-4}$ alkoxy,
b) halogen, or
c) aryl or heterocycle;

$R^8$ is independently selected from:
a) hydrogen,
b) $C_1-C_6$ alkyl, $C_2-C_6$ alkenyl, $C_2-C_6$ alkynyl, $C_1-C_6$ perfluoroalkyl, F, Cl, $R^{10}O-$, $R^{10}C(O)NR^{10}-$, CN, $NO_2$, $(R^{10})_2N-C(NR^{10})-$, $R^{10}C(O)-$, $-N(R^{10})_2$, or $R^{11}OC(O)NR^{10}-$, and
c) $C_1-C_6$ alkyl substituted by $C_1-C_6$ perfluoroalkyl, $R^{10}O-$, $R^{10}C(O)NR^{10}-$, $(R^{10})_2N-C(NR^{10})-$, $R^{10}C(O)-$, $-N(R^{10})_2$, or $R^{11}OC(O)NR^{10}-$;

$R^9$ is selected from:
a) hydrogen,
b) $C_2-C_6$ alkenyl, $C_2-C_6$ alkynyl, $C_1-C_6$ perfluoroalkyl, F, Cl, $R^{10}O-$, $R^{11}S(O)_m-$, $R^{10}C(O)NR^{10}-$, CN, $NO_2$, $(R^{10})_2N-C(NR^{10})-$, $R^{10}C(O)-$, $-N(R^{10})_2$, or $R^{11}OC(O)NR^{10}-$, and
c) $C_1-C_6$ alkyl unsubstituted or substituted by $C_1-C_6$ perfluoroalkyl, F, Cl, $R^{10}O-$, $R^{11}S(O)_m-$, $R^{10}C(O)NR^{10}-$, CN, $(R^{10})_2N-C(NR^{10})-$, $R^{10}C(O)-$, $-N(R^{10})_2$, or $R^{11}OC(O)NR^{10}-$;

$R^{10}$ is independently selected from hydrogen, $C_1-C_6$ alkyl, benzyl and aryl;
$R^{11}$ is independently selected from $C_1-C_6$ alkyl and aryl;
$A^1$ and $A^2$ are independently selected from: a bond, $-CH=CH-$, $-C\equiv C-$, $-C(O)-$, $-C(O)NR^{10}-$, O, $-N(R^{10})-$, or $S(O)_m$;
$A^3$ is selected from: $-C(O)-$, $-C(O)NR^{10}-$, $-C(O)O-$, and $S(O)_m$;
$A^4$ is selected from: a bond, O, and $NR^{10}$;
V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl,
c) aryl,
d) $C_1-C_{20}$ alkyl wherein from 0 to 4 carbon atoms are replaced with a heteroatom selected from O, S, and N, and
e) $C_2-C_{20}$ alkenyl, and provided that V is not hydrogen if $A^1$ is $S(O)_m$ and V is not hydrogen if $A^1$ is a bond, n is 0 and $A^2$ is $S(O)_m$;

W is a heterocycle selected from pyrrolidinyl, imidazolyl, pyridinyl, thiazolyl, pyridonyl, 2-oxopiperidinyl, indolyl, quinolinyl, or isoquinolinyl;
Z is unsubstituted or substituted aryl or unsubstituted or substituted heteroaryl;
m is 0, 1 or 2;
n is 0, 1, 2, 3 or 4;
p is 0, 1, 2, 3 or 4;
q is 1 or 2;
r is 0 to 5, provided that r is 0 when V is hydrogen;
s is 0 or 1;
t is 0 or 1; and
v is 0, 1, 2 or 3; provided that v is not 0 if $A^3$ is $-C(O)-$ or $S(O)_m$;
or the pharmaceutically acceptable salts thereof.

A preferred embodiment of the compounds of this invention are illustrated by the formula B:

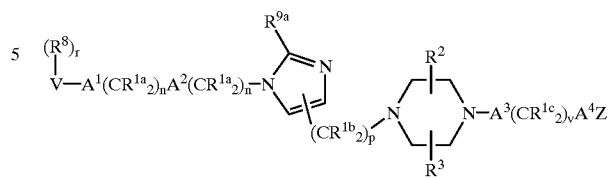

B wherein:
$R^{1a}$ and $R^{1b}$ are independently selected from:
a) hydrogen,
b) aryl, heterocycle, cycloalkyl, CN, $R^{10}O-$, $R^{10}NC(O)-$, $-N(R^{10})_2$ or $C_2-C_6$ alkenyl,
c) $C_1-C_6$ alkyl unsubstituted or substituted by aryl, heterocycle, cycloalkyl, alkenyl, $R^{10}O-$, or $-N(R^{10})_2$;

$R^{1c}$ is independently selected from:
a) hydrogen,
b) $C_3-C_{10}$ cycloalkyl, $R^{10}O-$, $R^{10}C(O)NR^{10}-$, $(R^{10})_2NC(O)-$, $R^{10}_2N-C(NR^{10})-$, CN, $NO_2$, $R^{10}C(O)-$, $N_3$, $-N(R^{10})_2$ or $R^{11}OC(O)NR^{10}-$,
c) unsubstituted or substituted $C_1-C_6$ alkyl wherein the substituent on the substituted $C_1-C_6$ alkyl is selected from $R^{10}O-$, $R^{10}C(O)NR^{10}-$, $(R^{10})_2NC(O)-$, $R^{10}_2N-C(NR^{10})-$, CN, $R^{10}C(O)-$, $N_3$, $-N(R^{10})_2$ and $R^{11}OC(O)-NR^{10}-$; or two $R^{1c}$s on the same carbon are combined with that carbon to form a $C_4-C_6$ cycloalkyl or $C_6-C_{10}$ multicyclic alkyl ring;

$R^3$ is selected from H and $CH_3$;
$R^2$ is selected from H;

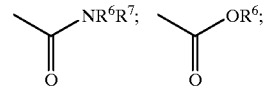

or $C_{1-5}$ alkyl, unbranched or branched, unsubstituted or substituted with one or more of:
1) aryl,
2) heterocycle,
3) $OR^6$,
4) $SR^{6a}$, $SO_2R^{6a}$, or
5)

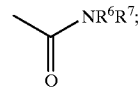

and $R^2$ and $R^3$ are optionally attached to the same carbon atom;
$R^6$ and $R^7$ are independently selected from: H; $C_{1-4}$ alkyl, $C_{3-6}$ cycloalkyl, aryl, heterocycle, unsubstituted or substituted with:
a) $C_{1-4}$ alkoxy,
b) halogen, or
c) aryl or heterocycle;

$R^{6a}$ is selected from: $C_{1-4}$ alkyl or $C_{3-6}$ cycloalkyl, unsubstituted or substituted with:
a) $C_{1-4}$ alkoxy,
b) halogen, or c) aryl or heterocycle;
$R^8$ is independently selected from:
a) hydrogen,
b) $C_1-C_6$ alkyl, $C_2-C_6$ alkenyl, $C_2-C_6$ alkynyl, $C_1-C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1-C_6$ alkyl substituted by $C_1-C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;
$R^{9a}$ is hydrogen, $C_1-C_6$ alkyl or chloro;
$R^{10}$ is independently selected from hydrogen, $C_1-C_6$ alkyl, benzyl and aryl;
$R^{11}$ is independently selected from $C_1-C_6$ alkyl and aryl;
$A^1$ and $A^2$ are independently selected from: a bond, —CH=CH—, —C≡C—, —C(O)—, —C(O)NR$^{10}$—, O, —N(R$^{10}$)—, or $S(O)_m$;
$A^3$ is selected from: —C(O)—, —C(O)NR$^{10}$—, —C(O)O— and $S(O)_m$;
$A^4$ is selected from: a bond, O, and NR$^{10}$;
V is selected from:
a) hydrogen,
b) heterocycle selected from pyrradinyl, imidazolyl, pyridinyl, thiazolyl, pyridonyl, 2-oxopiperidinyl, indolyl, quinolinyl, isoquinolinyl, and thienyl,
c) aryl,
d) $C_1-C_{20}$ alkyl wherein from 0 to 4 carbon atoms are replaced with a heteroatom selected from O, S, and N, and
e) $C_2-C_{20}$ alkenyl, and provided that V is not hydrogen if $A^1$ is $S(O)_m$ and V is not hydrogen if $A^1$ is a bond, n is 0 and $A^2$ is $S(O)_m$;
Z is unsubstituted or substituted aryl or unsubstituted or substituted heteroaryl;
m is 0, 1 or 2;
n is 0, 1, 2, 3 or 4;
p is 0, 1, 2, 3 or 4;
r is 0 to 5, provided that r is 0 when V is hydrogen; and
v is 0, 1, 2 or 3; provided that v is not 0 if $A^3$ is —C(O)— or $S(O)_m$;
or the pharmaceutically acceptable salts thereof.

Another preferred embodiment of the compounds of this invention are illustrated by the formula C:

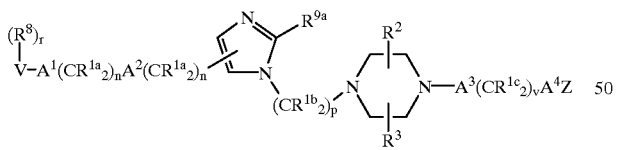

C wherein:
$R^{1a}$ and $R^{1b}$ are independently selected from:
a) hydrogen,
b) aryl, heterocycle, cycloalkyl, CN, $R^{10}O$—, $R^{10}NC(O)$—, —$N(R^{10})_2$ or $C_2-C_6$ alkenyl,
c) $C_1-C_6$ alkyl unsubstituted or substituted by aryl, heterocycle, cycloalkyl, alkenyl, $R^{10}O$—, or —$N(R^{10})_2$;
$R^{1c}$ is independently selected from:
a) hydrogen,
b) $C_3-C_{10}$ cycloalkyl, $R^{10}O$—, $R^{10}C(O)NR^{10}$—, $(R^{10})_2NC(O)$—, $R^{10}_2N$—$C(NR^{10})$—, CN, $NO_2$, $R^{10}C(O)$—, $N_3$, —$N(R^{10})_2$ or $R^{11}OC(O)NR^{10}$—, c) unsubstituted or substituted $C_1-C_6$ alkyl wherein the substituent on the substituted $C_1-C_6$ alkyl is selected from $R^{10}O$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$ and $R^{11}OC(O)$—$NR^{10}$—;or two $R^{1c}$s on the same carbon are combined with that carbon to form a $C_4-C_6$ cycloalkyl or $C_6-C_{10}$ multicyclic alkyl ring;
$R^3$ is selected from H and $CH_3$;
$R^2$ is selected from H;

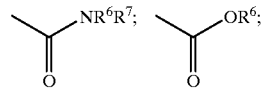

or $C_{1-5}$ alkyl, unbranched or branched, unsubstituted or substituted with one or more of:
1) aryl,
2) heterocycle,
3) $OR^6$,
4) $SR^{6a}$, $SO_2R^{6a}$, or
5)

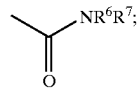

and $R^2$ and $R^3$ are optionally attached to the same carbon atom;
$R^6$ and $R^7$ are independently selected from: H; $C_{1-4}$ alkyl, $C_{3-6}$ cycloalkyl, aryl, heterocycle, unsubstituted or substituted with:
a) $C_{1-4}$ alkoxy,
b) halogen, or
c) aryl or heterocycle;
$R^{6a}$ is selected from: $C_{1-4}$ alkyl or $C_{3-6}$ cycloalkyl, unsubstituted or substituted with:
a) $C_{1-4}$ alkoxy,
b) halogen, or
c) aryl or heterocycle;
$R^8$ is independently selected from:
a) hydrogen,
b) $C_1-C_6$ alkyl, $C_2-C_6$ alkenyl, $C_2-C_6$ alkynyl, $C_1-C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1-C_6$ alkyl substituted by $C_1-C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;
$R^{9a}$ is hydrogen, $C_1-C_6$ alkyl or chloro;
$R^{10}$ is independently selected from hydrogen, $C_1-C_6$ alkyl, benzyl and aryl;
$R^{11}$ is independently selected from $C_1-C_6$ alkyl and aryl;
$A^1$ and $A^2$ are independently selected from: a bond, —CH=CH—, —C≡C—, —C(O)—, —C(O)NR$^{10}$—, O, —N(R$^{10}$)—, or $S(O)_m$;
$A^3$ is selected from: —C(O)—, —C(O)NR$^{10}$—, —C(O)O— and $S(O)_m$;
$A^4$ is selected from: a bond, O, and NR$^{10}$;
V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl, c) aryl, d) $C_1$–$C_{20}$ alkyl wherein from 0 to 4 carbon atoms are replaced with a heteroatom selected from O, S, and N, and e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

Z is unsubstituted or substituted aryl or unsubstituted or substituted heteroaryl;

m is 0, 1 or 2;

n is 0, 1, 2, 3 or 4;

p is 2, 3 or 4;

r is 0 to 5, provided that r is 0 when V is hydrogen; and v is 0, 1, 2 or 3; provided that v is not 0 if $A^3$ is —C(O)— or $S(O)_m$;

or the pharmaceutically acceptable salts thereof.

A further embodiment of the compounds of this invention is illustrated by the formula D:

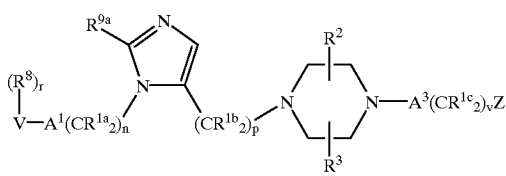

D wherein:

$R^{1a}$ and $R^{1b}$ are independently selected from:

a) hydrogen, b) aryl, heterocycle, cycloalkyl, CN, $R^{10}O$—, $R^{10}NC(O)$—, —$N(R^{10})_2$ or $C_2$–$C_6$ alkenyl, c) $C_1$–$C_6$ alkyl unsubstituted or substituted by aryl, heterocycle, cycloalkyl, alkenyl, $R^{10}O$—, or —$N(R^{10})_2$;

$R^{1c}$ is independently selected from:

a) hydrogen, b) $C_3$–$C_{10}$ cycloalkyl, $R^{10}O$—, $R^{10}C(O)NR^{10}$—, $(R^{10})_2NC(O)$—, $R^{10}_2N$—$C(NR^{10})$—, CN, $NO_2$, $R^{10}C(O)$—, $N_3$, —$N(R^{10})_2$ or $R^{11}OC(O)NR^{10}$—, c) unsubstituted or substituted $C_1$–$C_6$ alkyl wherein the substituent on the substituted $C_1$–$C_6$ alkyl is selected from $R^{10}O$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$ and $R^{11}OC(O)$—$NR^{10}$—; or two $R^{1c}$s on the same carbon are combined with that carbon to form a $C_4$–$C_6$ cycloalkyl or $C_6$–$C_{10}$ multicyclic alkyl ring;

$R^3$ is selected from H and $CH_3$;

$R^2$ is selected from H;

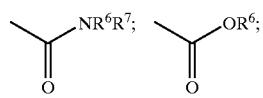

or $C_{1-5}$ alkyl, unbranched or branched, unsubstituted or substituted with one or more of:

1) aryl, 2) heterocycle,

3) $OR^6$,

4) $SR^{6a}$, $SO_2R^{6a}$, or

5)

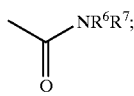

and $R^2$ and $R^3$ are optionally attached to the same carbon atom;

$R^6$ and $R^7$ are independently selected from: H; $C_{1-4}$ alkyl, $C_{3-6}$ cycloalkyl, aryl, heterocycle, unsubstituted or substituted with:

a) $C_{1-4}$ alkoxy, b) halogen, or c) aryl or heterocycle;

$R^{6a}$ is selected from: $C_{1-4}$ alkyl or $C_{3-6}$ cycloalkyl, unsubstituted or substituted with:

a) $C_{1-4}$ alkoxy, b) halogen, or c) aryl or heterocycle;

$R^8$ is independently selected from:

a) hydrogen, b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

$R^{9a}$ is hydrogen, $C_1$–$C_6$ alkyl or chloro;

$R^{10}$ is independently selected from hydrogen, $C_1$–$C_6$ alkyl, benzyl and aryl;

$R^{11}$ is independently selected from $C_1$–$C_6$ alkyl and aryl;

$A^1$ is selected from: a bond, —CH=CH—, —C≡C—, —C(O)—, —C(O)NR^{10}—, O, —N(R^{10})—, or $S(O)_m$;

$A^3$ is selected from: —C(O)—, —C(O)NR^{10}—, —C(O)O— and $S(O)_m$;

V is selected from:

a) heterocycle selected from pyridinyl and quinolinyl, and b) aryl;

Z is unsubstituted or substituted aryl or unsubstituted or substituted heteroaryl;

m is 0, 1 or 2;

n is 0, 1, 2, 3 or 4;

p is 0, 1, 2, 3 or 4;

r is 0 to 5, and v is 0, 1, 2 or 3; provided that v is not 0 if $A^3$ is —C(O)— or $S(O)_m$;

or the pharmaceutically acceptable salts thereof.

Another embodiment of the compounds of this invention is illustrated by the formula E:

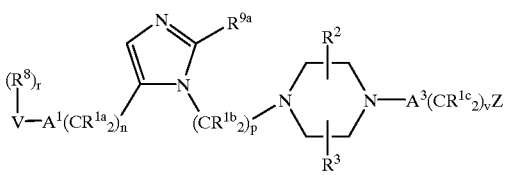

E wherein:

$R^{1a}$ and $R^{1b}$ are independently selected from:

a) hydrogen, b) aryl, heterocycle, cycloalkyl, CN, $R^{10}O-$, $R^{10}NC(O)-$, $-N(R^{10})_2$ or $C_2-C_6$ alkenyl, c) $C_1-C_6$ alkyl unsubstituted or substituted by aryl, heterocycle, cycloalkyl, alkenyl, $R^{10}O-$, or $-N(R^{10})_2$;

$R^{1c}$ is independently selected from:

a) hydrogen, b) $C_3-C_{10}$ cycloalkyl, $R^{10}O-$, $R^{10}C(O)NR^{10}-$, $(R^{10})_2NC(O)-$, $R^{10}{}_2N-C(NR^{10})-$, CN, $NO_2$, $R^{10}C(O)-$, $N_3$, $-N(R^{10})_2$ or $R^{11}OC(O)NR^{10}-$, c) unsubstituted or substituted $C_1-C_6$ alkyl wherein the substituent on the substituted $C_1-C_6$ alkyl is selected from $R^{10}O-$, $R^{10}C(O)NR^{10}-$, $(R^{10})_2NC(O)-$, $R^{10}{}_2N-C(NR^{10})-$, CN, $R^{10}C(O)-$, $N_3$, $-N(R^{10})_2$ and $R^{11}OC(O)-NR^{10}-$; or two $R^{1c}$s on the same carbon are combined with that carbon to form a $C_4-C_6$ cycloalkyl or $C_6-C_{10}$ multicyclic alkyl ring;

$R^3$ is selected from H and $CH_3$;

$R^2$ is selected from H;

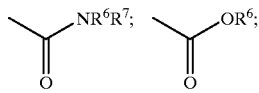

or $C_{1-5}$ alkyl, unbranched or branched, unsubstituted or substituted with one or more of:

1) aryl,
2) heterocycle,
3) $OR^6$,
4) $SR^{6a}$, $SO_2R^{6a}$, or
5)

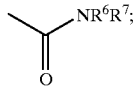

and $R^2$ and $R^3$ are optionally attached to the same carbon atom;

$R^6$ and $R^7$ are independently selected from: H; $C_{1-4}$ alkyl, $C_{3-6}$ cycloalkyl, aryl, heterocycle, unsubstituted or substituted with:

a) $C_{1-4}$ alkoxy,
b) halogen, or
c) aryl or heterocycle;

$R^{6a}$ is selected from: $C_{1-4}$ alkyl or $C_{3-6}$ cycloalkyl, unsubstituted or substituted with:

a) $C_{1-4}$ alkoxy,
b) halogen, or
c) aryl or heterocycle;

$R^8$ is independently selected from:

a) hydrogen, b) $C_1-C_6$ alkyl, $C_2-C_6$ alkenyl, $C_2-C_6$ alkynyl, $C_1-C_6$ perfluoroalkyl, F, Cl, $R^{10}O-$, $R^{10}C(O)NR^{10}-$, CN, $NO_2$, $(R^{10})_2N-C(NR^{10})-$, $R^{10}C(O)-$, $-N(R^{10})_2$, or $R^{11}OC(O)NR^{10}-$, and c) $C_1-C_6$ alkyl substituted by $C_1-C_6$ perfluoroalkyl, $R^{10}O-$, $R^{10}C(O)NR^{10}-$, $(R^{10})_2N-C(NR^{10})-$, $R^{10}C(O)-$, $-N(R^{10})_2$, or $R^{11}OC(O)NR^{10}-$;

$R^{9a}$ is hydrogen, $C_1-C_6$ alkyl or chloro;

$R^{10}$ is independently selected from hydrogen, $C_1-C_6$ alkyl, benzyl and aryl;

$R^{11}$ is independently selected from $C_1-C_6$ alkyl and aryl;

$A^1$ is selected from: a bond, $-CH=CH-$, $-C\equiv C-$, $-C(O)-$, $-C(O)NR^{10}-$, O, $-N(R^{10})-$, or $S(O)_m$;

$A^3$ is selected from: $-C(O)-$, $-C(O)NR^{10}-$, $-C(O)O-$ and $S(O)_m$;

V is selected from:

a) heterocycle selected from pyridinyl and quinolinyl, and b) aryl;

Z is unsubstituted or substituted aryl or unsubstituted or substituted heteroaryl;

m is 0, 1 or 2;

n is 0, 1, 2, 3 or 4;

p is 2, 3 or 4;

r is 0 to 5, and v is 0, 1, 2 or 3; provided that v is not 0 if $A^3$ is $-C(O)-$ or $S(O)_m$;

or the pharmaceutically acceptable salts thereof.

A still further embodiment of the compounds of this invention is illustrated by the formula F:

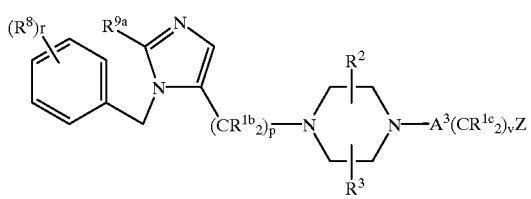

wherein:

$R^{1b}$ is independently selected from:

a) hydrogen, b) aryl, heterocycle, cycloalkyl, CN, $R^{10}O-$, $R^{10}NC(O)-$, $-N(R^{10})_2$ or $C_2-C_6$ alkenyl, c) $C_1-C_6$ alkyl unsubstituted or substituted by aryl, heterocycle, cycloalkyl, alkenyl, $R^{10}O-$, or $-N(R^{10})_2$;

$R^{1c}$ is independently selected from:

a) hydrogen, b) $C_3-C_{10}$ cycloalkyl, $R^{10}O-$, $R^{10}C(O)NR^{10}-$, $(R^{10})_2NC(O)-$, $R^{10}{}_2N-C(NR^{10})-$, CN, $NO_2$, $R^{10}C(O)-$, $N_3$, $-N(R^{10})_2$ or $R^{11}OC(O)NR^{10}-$, c) unsubstituted or substituted $C_1-C_6$ alkyl wherein the substituent on the substituted $C_1-C_6$ alkyl is selected from $R^{10}O-$, $R^{10}C(O)NR^{10}-$, $(R^{10})_2NC(O)-$, $R^{10}{}_2N-C(NR^{10})-$, CN, $R^{10}C(O)-$, $N_3$, $-N(R^{10})_2$ and $R^{11}OC(O)-NR^{10}-$; or two $R^{1c}$s on the same carbon are combined with that carbon to form a $C_4-C_6$ cycloalkyl or $C_6-C_{10}$ multicyclic alkyl ring;

$R^3$ is selected from H and $CH_3$;

$R^2$ is selected from H;

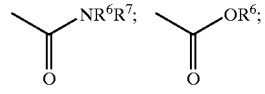

or $C_{1-5}$ alkyl, unbranched or branched, unsubstituted or substituted with one or more of:

1) aryl,
2) heterocycle,

3) $OR^6$,
4) $SR^{6a}$, $SO_2R^{6a}$, or
5)

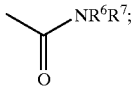

and $R^2$ and $R^3$ are optionally attached to the same carbon atom;

$R^6$ and $R^7$ are independently selected from: H; $C_{1-4}$ alkyl, $C_{3-6}$ cycloalkyl, aryl, heterocycle, unsubstituted or substituted with:
a) $C_{1-4}$ alkoxy,
b) halogen, or
c) aryl or heterocycle;

$R^{6a}$ is selected from: $C_{1-4}$ alkyl or $C_{3-6}$ cycloalkyl, unsubstituted or substituted with:
a) $C_{1-4}$ alkoxy,
b) halogen, or
c) aryl or heterocycle;

$R^8$ is independently selected from:
a) hydrogen,
b) $C_1-C_6$ alkyl, $C_2-C_6$ alkenyl, $C_2-C_6$ alkynyl, $C_1-C_6$ perfluoroalkyl, F, Cl, $R^{10}O-$, $R^{10}C(O)NR^{10}-$, CN, $NO_2$, $(R^{10})_2N-C(NR^{10})-$, $R^{10}C(O)-$, $-N(R^{10})_2$, or $R^{11}OC(O)NR^{10}-$, and
c) $C_1-C_6$ alkyl substituted by $C_1-C_6$ perfluoroalkyl, $R^{10}O-$, $R^{10}C(O)NR^{10}-$, $(R^{10})_2N-C(NR^{10})-$, $R^{10}C(O)-$, $-N(R^{10})_2$, or $R^{11}OC(O)NR^{10}-$;

$R^{9a}$ is hydrogen, $C_1-C_6$ alkyl or chloro;

$R^{10}$ is independently selected from hydrogen, $C_1-C_6$ alkyl, benzyl and aryl;

$R^{11}$ is independently selected from $C_1-C_6$ alkyl and aryl;

$A^3$ is selected from: $-C(O)-$, $-C(O)NR^{10}-$, $-C(O)O-$ and $S(O)_m$;

Z is unsubstituted or substituted phenyl, unsubstituted or substituted napthyl, unsubstituted or substituted pyridyl, unsubstituted or substituted quinoline or unsubstituted or substituted 1,2 methylenedioxybenzene;

m is 0, 1 or 2;
p is 1, 2 or 3;
r is 0 to 5, and
v is 0, 1, 2 or 3; provided that v is not 0 if $A^3$ is $-C(O)-$ or $S(O)_m$;

or the pharmaceutically acceptable salts thereof.

Another further embodiment of the compounds of this invention is illustrated by the formula G:

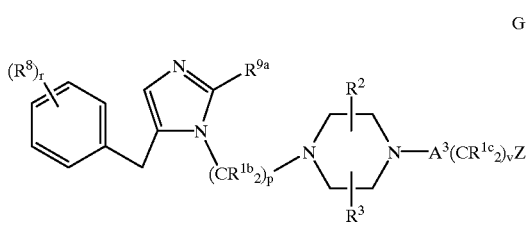

G wherein:
$R^{1b}$ is independently selected from:
a) hydrogen,
b) aryl, heterocycle, cycloalkyl, CN, $R^{10}O-$, $R^{10}NC(O)-$, $-N(R^{10})_2$ or $C_2-C_6$ alkenyl,
c) $C_1-C_6$ alkyl unsubstituted or substituted by aryl, heterocycle, cycloalkyl, alkenyl, $R^{10}O-$, or $-N(R^{10})_2$;

$R^{1c}$ is independently selected from:
a) hydrogen,
b) $C_3-C_{10}$ cycloalkyl, $R^{10}O-$, $R^{10}C(O)NR^{10}-$, $(R^{10})_2NC(O)-$, $R^{10}_2N-C(NR^{10})-$, CN, $NO_2$, $R^{10}C(O)-$, $N_3$, $-N(R^{10})_2$ or $R^{11}OC(O)NR^{10}-$,
c) unsubstituted or substituted $C_1-C_6$ alkyl wherein the substituent on the substituted $C_1-C_6$ alkyl is selected from $R^{10}O-$, $R^{10}C(O)NR^{10}-$, $(R^{10})_2NC(O)-$, $R^{10}_2N-C(NR^{10})-$, CN, $R^{10}C(O)-$, $N_3$, $-N(R^{10})_2$ and $R^{11}OC(O)-NR^{10}-$; or two $R^{1c}$s on the same carbon are combined with that carbon to form a $C_4-C_6$ cycloalkyl or $C_6-C_{10}$ multicyclic alkyl ring;

$R^3$ is selected from H and $CH^3$;
$R^2$ is selected from H;

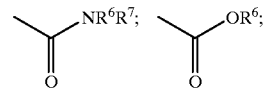

or $C_{1-5}$ alkyl, unbranched or branched, unsubstituted or substituted with one or more of:
1) aryl,
2) heterocycle,
3) $OR^6$,
4) $SR^{6a}$, $SO_2R^{6a}$, or
5)

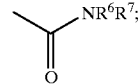

and $R^2$ and $R^3$ are optionally attached to the same carbon atom;

$R^6$ and $R^7$ are independently selected from: H; $C_{1-4}$ alkyl, $C_{3-6}$ cycloalkyl, aryl, heterocycle, unsubstituted or substituted with:
a) $C_{1-4}$ alkoxy,
b) halogen, or
c) aryl or heterocycle;

$R^{6a}$ is selected from: $C_{1-4}$ alkyl or $C_{3-6}$ cycloalkyl, unsubstituted or substituted with:
a) $C_{1-4}$ alkoxy,
b) halogen, or
c) aryl or heterocycle;

$R^8$ is independently selected from:
a) hydrogen,
b) $C_1-C_6$ alkyl, $C_2-C_6$ alkenyl, $C_2-C_6$ alkynyl, $C_1-C_6$ perfluoroalkyl, F, Cl, $R^{10}O-$, $R^{10}C(O)NR^{10}-$, CN, $NO_2$, $(R^{10})_2N-C(NR^{10})-$, $R^{10}C(O)-$, $-N(R^{10})_2$, or $R^{11}OC(O)NR^{10}-$, and
c) $C_1-C_6$ alkyl substituted by $C_1-C_6$ perfluoroalkyl, $R^{10}O-$, $R^{10}C(O)NR^{10}-$, $(R^{10})_2N-C(NR^{10})-$, $R^{10}C(O)-$, $-N(R^{10})_2$, or $R^{11}OC(O)NR^{10}-$;

$R^{9a}$ is hydrogen, $C_1-C_6$ alkyl or chloro;

$R^{10}$ is independently selected from hydrogen, $C_1-C_6$ alkyl, benzyl and aryl;

$R^{11}$ is independently selected from $C_1-C_6$ alkyl and aryl;

$A^3$ is selected from: $-C(O)-$, $-C(O)NR^{10}-$, $-C(O)O-$ and $S(O)_m$;

Z is unsubstituted or substituted phenyl, unsubstituted or substituted napthyl, unsubstituted or substituted pyridyl, unsubstituted or substituted quinoline or unsubstituted or substituted 1,2 methylenedioxybenzene;

m is 0, 1 or 2;
p is 2 or 3;
r is 0 to 5, and
v is 0, 1, 2 or 3; provided that v is not 0 if $A^3$ is —C(O)— or $S(O)_m$;
or the pharmaceutically acceptable salts thereof.

Specific examples of the compounds of this invention are as follows:

1-[1-(4'-Cyanobenzyl)imidazol-5-ylmethyl]-4-[1-phenyl-1-cyclopentylcarbonyl]piperazine
1-[1-(4'-Cyanobenzyl)imidazol-5-ylmethyl]-4-[cyclohexylphenylacetyl]piperazine
1-[1-(4'-Cyanobenzyl)imidazol-5-ylmethyl]-4-[1-(3-methoxyphenyl)-1-cyclopentylcarbonyl]piperazine
1-[1-(4'-Cyanobenzyl)imidazol-5-ylmethyl]-4-[1-(3-phenoxyphenyl)-1-cyclopentylcarbonyl]piperazine
1-[1-(4'-Cyano-3-fluorobenzyl)imidazol-5-ylmethyl]-4-[1-(3-hydroxyphenyl)-1-cyclohexylcarbonyl]piperazine
1-[1-(4'-Cyanobenzyl)imidazol-5-ylmethyl]piperazine-4-carboxylic acid-(2,6-dimethoxy)benzyl ester
1-[1-(4'-Cyanobenzyl)imidazol-5-ylmethyl]piperazine-4-(DL-2-hydroxy-2-(o-methoxyphenyl))acetamide
1-[1-(4'-Cyanobenzyl)imidazol-5-ylmethyl]-4-[1-(2,6-dimethylbenzyloxycarbonyl]piperazine
1-[1-(4'-Cyanobenzyl)imidazol-5-ylmethyl]-4-[1-(2-methoxyphenyl)-1-cyclopentylcarbonyl]piperazine
(±) 1-[1-(4'-Cyanobenzyl)imidazol-5-ylmethyl]-4-[1-(bicyclo[3.1.0]hex-3-yl)-1-(3-methoxyphenyl)-carbonyl]piperazine
(R/S) 2-[4-((Phenyl)methyloxycarbonyl-1-piperazine)]-2-[1-(4'-cyanobenzyl)-2-methyl-5-imidazol]acetonitrile
1-[1-(4'-methylbenzyl)imidazol-5-ylmethyl]-4-[1-(2,6-dimethylbenzyloxycarbonyl]piperazine
1-[1-(4'-Cyanobenzyl)imidazol-5-ylmethyl]piperazine-4-carboxylic acid-(4-nitro)phenyl ester
1-[1-(4-Cyanobenzyl)imidazol-5-ylmethyl]-4-[3-(4-fluorophenyl)-3-(tricyclo[3.3.1.1$^{3,7}$]dec-2-yl)-propionyl]piperazine
2-(1-(4'-cyanobenzyl)imidazol-5-yl)-2-[4-(phenylmethyloxy carbonyl)piperazin-1-yl]acetamide
1-[1-(4'-cyanobenzyl)imidazol-5-ylmethyl]-4-[1-(2-methoxy-5-chlorobenzyloxycarbonyl]piperazine
1-[1-(4'-cyanobenzyl)imidazol-5-ylmethyl]-4-[1-(pentafluororobenzyloxycarbonyl]piperazine
1-[1-(4'-cyanobenzyl)imidazol-5-ylmethyl]-4-[1-(2-ethoxybenzyloxycarbonyl]piperazine
1-[1-(4'-cyanobenzyl)imidazol-5-ylmethyl]-4-{1-[(2-methoxypyridin-3-yl)methyloxycarbonyl]}piperazine
1-[1-(4'-cyanobenzyl)imidazol-5-ylmethyl]-4-[1-(2-trifluoromethoxybenzyloxycarbonyl]piperazine
1-[1-(4'-cyanobenzyl)imidazol-5-ylmethyl]-4-[1-(2,3-methylenedioxybenzyloxycarbonyl]piperazine
1-[1-(4'-Cyanobenzyl)imidazol-5-ylmethyl]piperazine-4-carboxylic acid benzyl ester
1-[1-(4'-Cyanobenzyl)imidazol-5-ylmethyl]-piperazine-3-carboxylic acid-4-carboxylic acid benzyl ester
1-[1-(4'-Cyanobenzyl)imidazol-5-ylmethyl]-3-methyl carboxy-piperazine-4-carboxylic acid benzyl ester
1-[1-(4'-Cyanobenzyl)imidazol-5-ylmethyl]piperazine-4-(N-3-isopropenyl-1,1-dimethylbenzyl)carboxamide
1-[1-(4'-cyanobenzyl)imidazol-5-ylmethyl]-4-phenylmethanesulfonyl-(cis)-2,6-dimethylpiperazine
2-(1-(4'-cyanobenzyl)-5-imidazolyl))-2-[(4'-phenylmethyloxycarbonyl)piperazin-1'-yl]acetonitrile
1-[1-(4'-Cyanobenzyl)imidazol-5-ylmethyl]-4-(2-tert-butyl-3-phenyl)propionyl piperazine
1-[1-(4'-Cyanobenzyl)imidazol-5-ylmethyl]-4-[1-(4-methoxyphenyl)-1-cyclohexyl]carbonyl piperazine
1-[1-(4'-Cyanobenzyl)imidazol-5-ylmethyl]-4-{1-[(2-ethoxypyridin-3-yl)methyloxycarbonyl]piperazine
1-[1-(4'-Cyanobenzyl)imidazol-5-ylmethyl]-4-[1-(2-methanesulfonylbenzyloxycarbonyl)piperazine
1-[1-(4'-Cyanobenzyl)imidazol-5-yl)-piperazine-4-(N-2-(ethoxybenzyl)carbamide)
1-[1-(4'-Cyanobenzyl)-2-methyl)imidazol-5-yl)-4-(benzyloxycarbonyl)]piperazine
1-[1-(4'-Cyanobenzyl)imidazol-5-ylmethyl]piperazine-4-(N-3-methylbenzyl)carboxamide
1-[1-(4'-Cyanobenzyl)imidazol-5-ylmethyl]piperazine-4-(N-2-chlorobenzyl)carboxamide
1-[1-(4'-Cyanobenzyl)imidazol-5-yl)]piperazine-4-(N-2-methoxybenzyl)carboxamide
1-[1-(4'-Cyanobenzyl)imidazol-5-yl]piperazine-4-(N-3-methoxy-6-chlorobenzyl)carboxamide
1-[1-(4'-Cyanobenzyl)imidazol-5-yl]piperazine-4-(N-(2-methyl-5-chlorobenzyl))carboxamide
1-[1-(4'-Cyanobenzyl)imidazol-5-yl]piperazine-4-(N-(3-phenylpropyl))carboxamide
1-[1-(4'-Cyanobenzyl)imidazol-5-yl]piperazine-4-(N-(2,5-dimethylbenzyl))carbamide
1-[1-(4'-Cyanobenzyl)imidazole-5-ylmethyl]-4-benzyloxycarbonyl)-(trans)-2,5-dimethylpiperazine
1-[(4-cyanophenyl)methylimidazol-5-ylmethyl]piperazine-4-2,4-dimethylbenzyloxycarbonyl
1-[1-(4-cyanophenyl)methylimidazol-5-ylmethyl]piperazine-4-(2-methylbenzyloxycarbonyl)
1-[1-(4-cyanophenyl)methylimidazol-5-ylmethyl]piperazine-4-(4'-acetamidobenzyloxycarbonyl)
1-[1-(4-cyanophenyl)methylimidazol-5-ylmethyl]piperazine-4-[(3'-methylbenzyloxycarbonyl)
1-[1-(4-cyanophenyl)methylimidazol-5-ylmethyl]piperazine-4-(2'-methoxybenzyloxycarbonyl)
1-[1-(4-cyanophenyl)methylimidazol-5-ylmethyl]piperazine-4-(3'-methoxybenzyloxycarbonyl)
1-[1-(4-cyanophenyl)methylimidazol-5-ylmethyl]piperazine-4-(1-oxypyridine-3-methyloxycarbonyl)
1-[1-(4-cyanophenyl)methylimidazol-5-ylmethyl]piperazine-4-(3-pyridinemethyloxycarbonyl)
1-[1-(4-cyanophenyl)methylimidazol-5-ylmethyl]piperazine-4-(4'-pyridinemethyloxycarbonyl)
1-[1-(4-cyanophenyl)methylimidazol-5-ylmethyl]piperazine-4-(2',5'-dimethylbenzyloxycarbonyl)
1-[1-(4-cyanophenyl)methylimidazol-5-ylmethyl]piperazine-4-[(1,3-benzodioxolan-5-methyl)oxycarbonyl]
1-[1-(4-cyanobenzyl)-2-methylimidazol-5-ylmethyl]-4-[2-ethoxybenzyloxycarbonyl]piperazine
1-[1-(4-cyanobenzyl)-2-methylimidazol-5-ylmethyl]-4-[2-(trifluoromethoxy)benzyloxycarbonyl]piperazine
1-[1-(4-cyanobenzyl)-2-methylimidazol-5-ylmethyl]-4-[2,3-(difluoromethylenedioxy)benzyloxycarbonyl]piperazine
1-[1-(4-cyanobenzyl)-2-methylimnidazol-5-ylmethyl]-4-[3-ethoxybenzyloxy)carbonyl]piperazine
1-[1-(4-cyanobenzyl)-2-methylimidazol-5-ylmethyl]-4-[2-(difluoromethoxy)benzyloxycarbonyl]piperazine
1-[1-(4-cyanobenzyl)-2-methylimidazol-5-ylmethyl]-4-[2-(trifluoromethyl)benzyloxycarbonyl]piperazine
1-[1-(4-cyanobenzyl)-2-methylimidazol-5-ylmethyl]-4-[2-(difluoromethoxy)-5-methylbenzyloxycarbonyl]piperazine 1-[1-(4-cyanobenzyl)-2-methylimidazol-5-ylmethyl]-4-[2-(trifluormethylsulfonyl)benzyloxycarbonyl]piperazine (±)-1-[1-(4-cyanobenzyl)-2-methylimidazol-5-ylmethyl]-4-[2-(trifluormethylsulfoxy)benzyloxycarbonyl]piperazine 1-[1-(4-cyanobenzyl)-2-methylimidazol-5-ylmethyl]-4-[2-(trifluormethylthio)benzyloxycarbonyl]piperazine 1-[1-(4'-Cyanobenzyl)imidazole-5-ylmethyl]-4-[2-(2,2,2-trifluoroethoxy)benzyloxycarbonyl]piperazine (R/S) 2-[4-((2-ethoxyphenyl)methyloxycarbonyl-1-piperazine)]-2-[1-(4-cyanobenzyl)-2-methyl-5-imadazol]acetonitrile 1-[1-(4'-Cyanobenzyl)-2-methyl-imidazol-5-ylmethyl]piperazine-4-(N-2-trifluoromethoxybenzyl)carboxamide 1-[1-(4'-Cyanobenzyl)-2-methyl-imidazol-5-ylmethyl]piperazine-4-{N-[2-(3-trifluoromethylphenyl)ethyl]}carboxamide 1-[1-(4'-Cyanobenzyl)-2-methyl-imidazol-5-ylmethyl]piperazine-4-N-(2-fluoro-5-trifluoromethylbenzyl)carboxamide 1-[1-(4'-Cyanobenzyl)-2-methyl imidazol-5-ylmethyl]piperazine-4-carboxylic acid-(2-fluoro-3-trifluoromethyl)benzyl ester or the pharmaceutically acceptable salts or optical isomers thereof.

Particular examples of compounds of this invention are:

1-[1-(4'-Cyanobenzyl)imidazol-5-ylmethyl]piperazine-4-carboxylic acid-(2,6-dimethoxy)benzyl ester

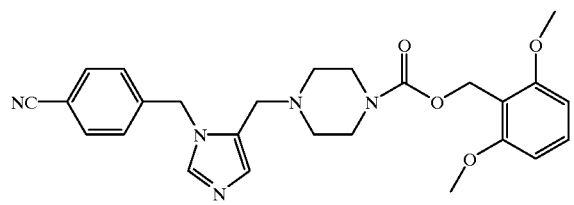

1-[1-(4'-Cyanobenzyl)imidazol-5-ylmethyl]-4-[1-(2,6-dimethylbenzyloxycarbonyl]piperazine

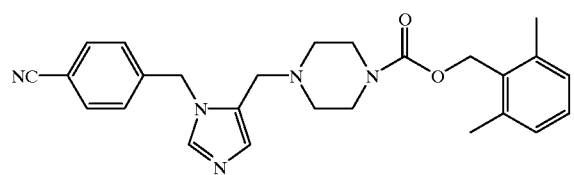

1-[1-(4'-methylbenzyl)imidazol-5-ylmethyl]-4-[1-(2,6-dimethylbenzyloxycarbonyl]piperazine

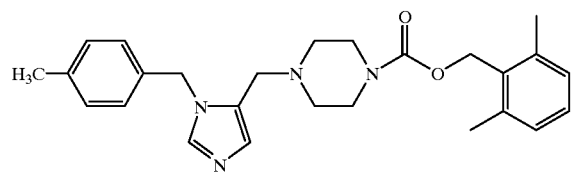

1-[1-(4'-cyanobenzyl)imidazol-5-ylmethyl]-4-[1-(2-ethoxybenzyloxycarbonyl]piperazine

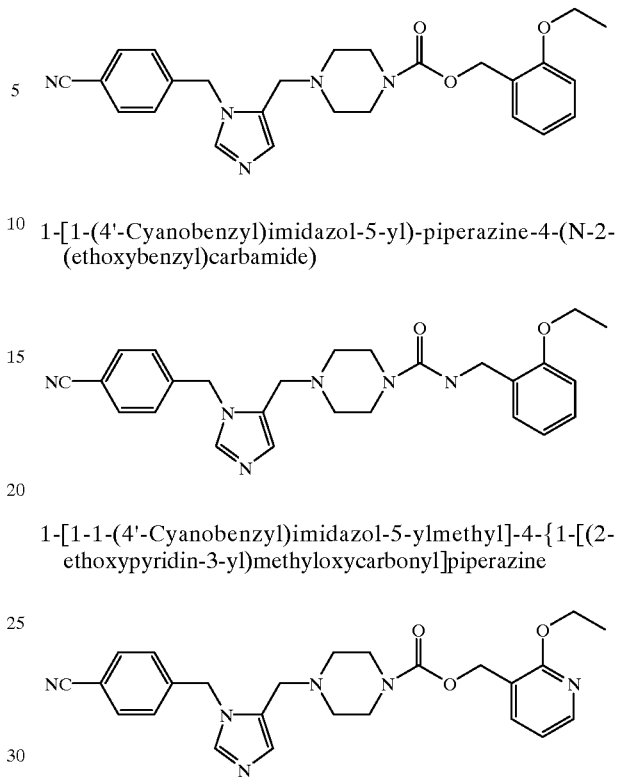

1-[1-(4'-Cyanobenzyl)imidazol-5-yl)-piperazine-4-(N-2-(ethoxybenzyl)carbamide)

1-[1-1-(4'-Cyanobenzyl)imidazol-5-ylmethyl]-4-{1-[(2-ethoxypyridin-3-yl)methyloxycarbonyl]piperazine or the pharmaceutically acceptable salts or optical isomers thereof.

The compounds of the instant invention differ from previously disclosed piperazinone-containing and piperazine-containing compounds, (PCT Publ. No. WO 96/30343—Oct. 3, 1996; PCT Publ. No. WO 96/31501—Oct. 10, 1996; PCT Publ. No. WO 97/36593—Oct. 9, 1997; PCT Publ. No. WO 97/36592—Oct. 9, 1997) that were described as inhibitors of farnesyl-protein transferase (FPTase), in that, among other things, the instant compounds are dual inhibitors of farnesyl-protein transferase and geranylgeranyl-protein transferase type I (GGTase-I).

In one embodiment of the invention, the compounds are further characterized in that the inhibitory activity of the compounds against GGTase-I is greater than the inhibitory activity against FPTase. Preferably, the compounds of this embodiment of the instant invention inhibit FPTase in vitro (Example 59) at an $IC_{50}$ of less than 1 μM and inhibit GGTase-I in vitro (Example 60) at an $IC_{50}$ of less than 50 nM. Also preferably, the compounds of this embodiment of the instant invention inhibit the cellular processing of the Rap1 protein (Example 65) at an $EC_{50}$ of less than about 1 μM. More preferably, the compounds of this embodiment of the instant invention inhibit the cellular processing of the Rap1 protein (Example 65) at an $EC_{50}$ of less than about 50 nM. Also more preferably, the ratio of the $IC_{50}$ of the compounds of this embodiment of the instant invention for in vitro inhibition of FPTase to the $IC_{50}$ of the compounds of the instant invention for in vitro inhibition of GGTase type I is greater than 25. Also more preferably, the ratio of the $EC_{50}$ of the compounds of this embodiment of the instant invention for inhibition of the cellular processing of the hDJ protein (Example 64) to the $EC_{50}$ of the compounds of the instant invention for inhibition of the cellular processing of the Rap1 protein is about equal to or less than 1.

In a second embodiment of the compounds of the instant invention, the compounds are further characterized in that the inhibitory activity of the compounds against FPTase is greater than the inhibitory activity against GGTase-I. Preferably, the compounds of this second embodiment of the instant invention inhibit FPTase in vitro (Example 59) at an $IC_{50}$ of less than 100 nM and inhibit GGTase-I in vitro (Example 60) at an $IC_{50}$ of less than 5 $\mu$M. Preferably, the compounds of this second embodiment of the instant invention inhibit the cellular processing of the hDJ protein (Example 64) at an $EC_{50}$ of less than about 250 nM. Also preferably, the compounds of this second embodiment of the instant invention inhibit the cellular processing of the Rap1 protein (Example 65) at an $EC_{50}$ of less than about 10 $\mu$M. More preferably, the compounds of this second embodiment of the instant invention inhibit the cellular processing of the Rap1 protein (Example 65) at an $EC_{50}$ of less than about 1 $\mu$M. Also more preferably, the ratio of the $IC_{50}$ of the compounds of this embodiment of the instant invention for in vitro inhibition of GGTase type I to the $IC_{50}$ of the compounds of the instant invention for in vitro inhibition of FPTase is greater than 1 and less than 25. Also more preferably, the ratio of the $EC_{50}$ of the compounds of this second embodiment of the instant invention for inhibition of the cellular processing of the hDJ protein (Example 64) to the $EC_{50}$ of the compounds of the instant invention for inhibition of the cellular processing of the Rap1 protein is between about 1 and about 100.

The compounds of the present invention may have asymmetric centers and occur as racemates, racemic mixtures, and as individual diastereomers, with all possible isomers, including optical isomers, being included in the present invention. When any variable (e.g. aryl, heterocycle, $R^1$, $R^2$ etc.) occurs more than one time in any constituent, its definition on each occurrence is independent at every other occurrence. Also, combinations of substituents/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge. "Alkenyl" is intended to include both branched and straight-chain unsaturated aliphatic hydrocarbon groups having the specified number of carbon atoms. "Halogen" or "halo" as used herein means fluoro, chloro, bromo and iodo.

As used herein, "cycloalkyl" is intended to include monocyclic saturated aliphatic hydrocarbon groups having the specified number of carbon atoms. Examples of such cycloalkyl groups includes, but are not limited to, cyclopropyl, cyclobutyl, cyclohexyl, cycloheptyl and cyclooctyl.

As used herein, "aryl" is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

The term heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings are fused to a benzene ring. The term heterocycle or heterocyclic includes heteroaryl moieties. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyridyl N-oxide, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, and thienyl.

As used herein in the defmition of $R^2$ and $R^3$, the term "the substituted group" is intended to mean a substituted $C_{1-8}$ alkyl, substituted $C_{2-8}$ alkenyl, substituted $C_{2-8}$ alkynyl, substituted aryl or substituted heterocycle from which the substituent(s) $R^2$ and $R^3$ are selected.

As used herein in the definition of $R^6$, $R^{6a}$, $R^7$ and $R_{7a}$, the substituted $C_{1-8}$ alkyl, substituted $C_{3-6}$ cycloalkyl, substituted aroyl, substituted aryl, substituted heteroaroyl, substituted arylsulfonyl, substituted heteroarylsulfonyl and substituted heterocycle include moieties containing from 1 to 3 substituents in addition to the point of attachment to the rest of the compound. Preferably, such substituents are selected from the group which includes but is not limited to F, Cl, Br, $CF_3$, $NH_2$, $N(C_1–C_6$ alkyl$)_2$, $NO_2$, CN, $(C_1–C_6$ alkyl)O—, —OH, $(C_1–C_6$ alkyl)S(O)$_m$—, $(C_1–C_6$ alkyl)C(O)NH—, $H_2N$—C(NH)—, $(C_1–C_6$ alkyl)C(O)—, $(C_1–C_6$ alkyl)OC (O)—, $N_3$,$(C_1–C_6$ alkyl)OC(O)NH—, phenyl, pyridyl, imidazolyl, oxazolyl, isoxazolyl, thiazolyl, thienyl, furyl, isothiazolyl and $C_1–C_{20}$ alkyl.

As used herein in the definition of Z the substituted aryl and substituted heteroaryl include moieties containing from 1 to 5 substituents in addition to the point of attachment to the rest of the compound. Preferably, such substituents are selected from the group which includes but is not limited to F, Cl, Br, $CF_3$, $OCF_3$, $NH_2$, $N(C_1–C_6$ alkyl$)_2$, $NO_2$, $SO_2CH_3$, CN, $(C_1–C_6$ alkyl)O—, (aryl)O—, —OH, $(C_1–C_6$ alkyl)S (O)$_m$—, $(C_1–C_6$ alkyl)C(O)NH—, $H_2N$—C(NH)—, $(C_1–C_6$ alkyl)C(O)—, $(C_1–C_6$ alkyl)OC(O)—, $N_3$, $(C_1–C_6$ alkyl)OC (O)NH—, phenyl, pyridyl, imidazolyl, oxazolyl, isoxazolyl, thiazolyl, thienyl, furyl, isothiazolyl and $C_1$–$C_{20}$ alkyl, $C_2$–$C_6$ alkenyl.

When $R^2$ and $R^3$ are combined to form —$(CH_2)_u$—, cyclic moieties are formed. Examples of such cyclic moieties include, but are not limited to:

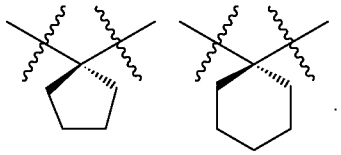

In addition, such cyclic moieties may optionally include a heteroatom(s). Examples of such heteroatom-containing cyclic moieties include, but are not limited to:

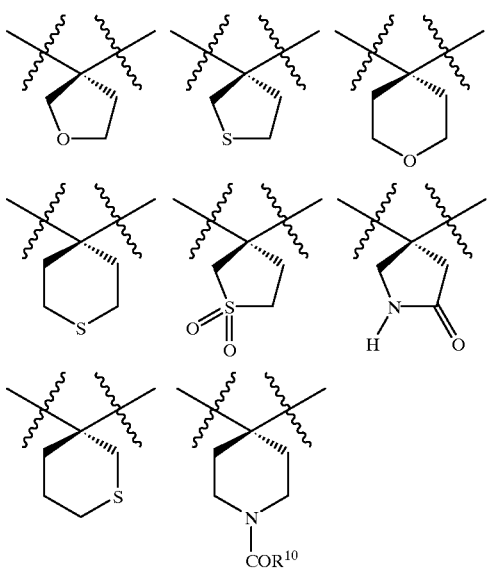

The moiety formed when, in the definition of $R^6$, $R^7$ and $R^{7a}$, $R^6$ and $R^7$ or $R^7$ and $R^{7a}$ are joined to form a ring, is illustrated by, but not limited to, the following:

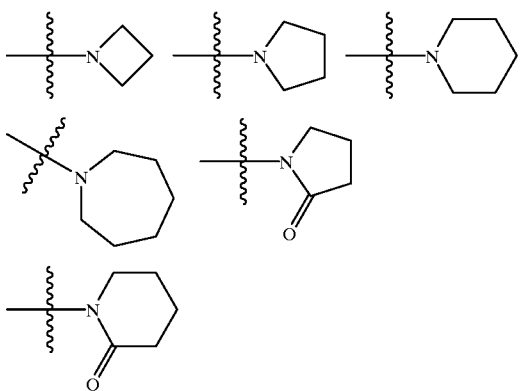

Lines drawn into the ring systems from substituents (such as from $R^2$, $R^3$, $R^4$ etc.) indicate that the indicated bond may be attached to any of the substitutable ring carbon atoms.

The term $C_4$–$C_6$ cycloalkyl in the definition of $R^{1c}$ wherein two $R^{1c}$s are combined is illustrated by the following:

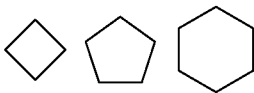

The term $C_6$–$C_{10}$ "multicyclic alkyl ring" in the definition of $R^{1c}$ wherein two $R^{1c}$s are combined is intended to include polycyclic saturated and unsaturated aliphatic hydrocarbon groups having the specified number of carbon atoms. Examples of such cycloalkyl groups includes, but are not limited to:

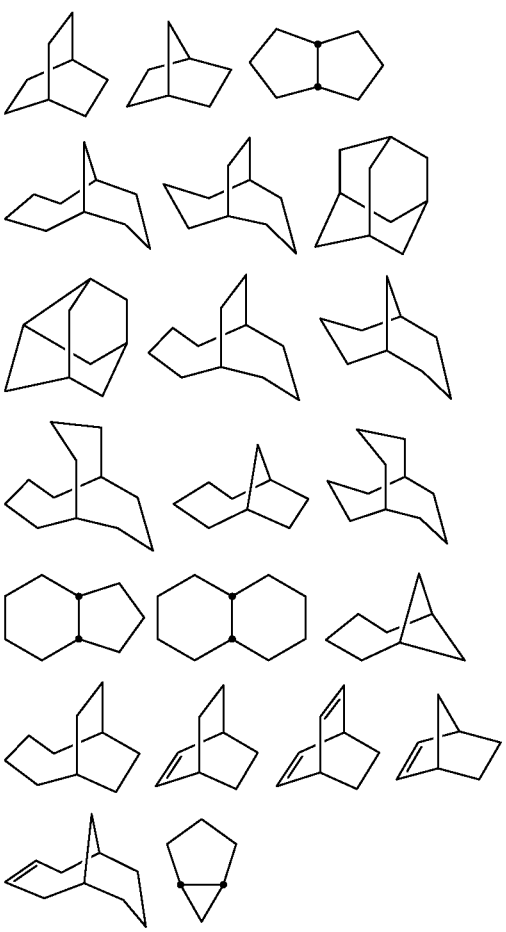

Preferably, $R^{1a}$ and $R^{1b}$ are independently selected from: hydrogen, CN, —$N(R^{10})_2$, $R^{10}NC(O)$—, $R^{10}C(O)NR^{10}$— or unsubstituted or substituted $C_1$–$C_6$ alkyl wherein the substituent on the substituted $C_1$–$C_6$ alkyl is selected from unsubstituted or substituted phenyl, —$N(R^{10})_2$, $R^{10}O$— and $R^{10}C(O)NR^{10}$—.

Preferably, $R^{1c}$ is independently selected from: hydrogen, $C_3$–$C_{10}$ cycloalkyl, $R^{10}O$—, $C_1$–$C_6$ alkyl, or two $R^{1c}$s on the same carbon are combined with that carbon to form a $C_4$–$C_6$ cycloalkyl or $C_6$–$C_{10}$ multicyclic alkyl ring.

Preferably, $R^2$ is selected from: hydrogen,

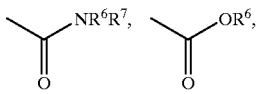

and an unsubstituted or substituted group, the group selected from $C_{1-8}$ alkyl, $C_{2-8}$ alkenyl and $C_{2-8}$ alkynyl; wherein the substituted group is substituted with one or more of:

1) aryl or heterocycle,
2) $OR^6$,
3) $SR^{6a}$, $SO_2R^{6a}$,

Preferably $R^3$ is selected from H and $CH_3$.
Preferably, $R^4$ is hydrogen.
Preferably, $R^6$ and $R^7$ are selected from: hydrogen, unsubstituted or substituted $C_1$–$C_6$ alkyl, unsubstituted or substituted aryl and unsubstituted or substituted $C_3$–$C_6$ cycloalkyl.
Preferably, $R^{6a}$ is unsubstituted or substituted $C_1$–$C_6$.
Preferably, $R^9$ is hydrogen, chloro or $C_1$–$C_6$ alkyl.
Preferably, $R^{10}$ is selected from H, $C_1$–$C_6$ alkyl, benzyl and aryl.
Preferably, $A^1$ and $A^2$ are independently selected from: a bond, $-C(O)NR^{10}-$, $-NR^{10}C(O)-$, O, $-N(R^{10})-$, $-S(O)_2N(R^{10})-$ and $-N(R^{10})S(O)_2-$. Most preferably, $A^1$ and $A^2$ are a bond.
Preferably, $A^3$ is selected from: $-C(O)-$, $-C(O)NR^{10}-$, $-C(O)O-$ and $S(O)_m$.
Preferably, V is selected from heteroaryl and aryl. More preferably, V is phenyl.
Preferably, W is selected from imidazolyl, pyridinyl, thiazolyl, indolyl, quinolinyl, and isoquinolinyl. More preferably W is selected from imidazolyl and pyridinyl.
Preferably, Z is selected from unsubstituted or substituted phenyl, unsubstituted or substituted napthyl, unsubstituted or substituted pyridyl, unsubstituted or substituted quinoline and unsubstituted or substituted 1,2 methylenedioxybenzene, wherein the substituted phenyl, substituted napthyl, substituted pyridyl, substituted quinoline and substituted 1,2 methylenedioxybenzene are substituted with one or more of the following:

a) OH,
b) alkoxy,
c) aryloxy,
d) $C_1$–$C_6$ alkyl,
e) $NO_2$,
f) halogen,
g) $C_2$–$C_6$ alkenyl,
h) $OCF_3$,
i) $SO_2CH_3$, or
j) $(C_1$–$C_6$ alkyl)C(O)NH—

More preferably, Z is unsubstituted or substituted phenyl, unsubstituted or substituted pyridyl or unsubstituted or substituted 1,2 methylenedioxybenzene wherein the substituted phenyl, substituted pyridyl and substituted 1,2 methylenedioxybenzene are substituted with one or more of the following:

a) OH,
b) alkoxy,
c) aryloxy,
d) $C_1$–$C_6$ alkyl,
e) $NO_2$,
f) halogen,
g) $C_2$–$C_6$ alkenyl,
h) $OCF_3$,
I) $SO_2CH_3$, or
j) $(C_1$–$C_6$ alkyl)C(O)NH—

Preferably, n and r are independently 0, 1, or 2.
Preferably p is 1, 2 or 3.
Preferably s is 0.
Preferably t is 1.
Preferably v is 0, 1, 2 or 3; provided that v is not 0 if $A^3$ is $-C(O)-$ or $S(O)_m$.
Preferably, the moiety

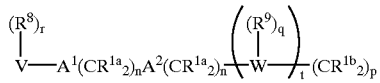

is selected from:

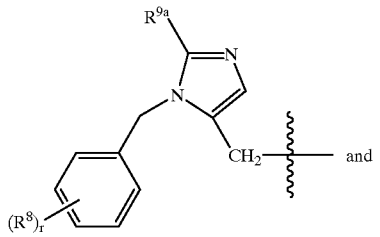

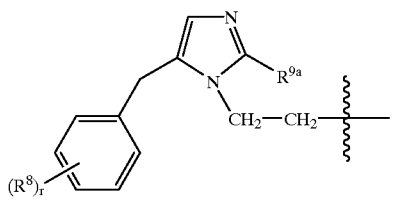

Preferably, the moiety

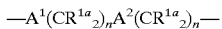

is not a bond.

It is intended that the definition of any substituent or variable (e.g., $R^{1a}$, $R^9$, n, etc.) at a particular location in a molecule be independent of its definitions elsewhere in that molecule. Thus, $-N(R^{10})_2$ represents $-NHH$, $-NHCH_3$, $-NHC_2H_5$, etc. It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Reactions used to generate the compounds of this invention are prepared by employing reactions as shown in the Schemes 1–20, in addition to other standard manipulations such as ester hydrolysis, cleavage of protecting groups, etc., as may be known in the literature or exemplified in the experimental procedures. Substituents R, $R^a$ and $R^b$, as shown in the Schemes, represent the substituents $R^2$, $R^3$ and $R^4$; however their point of attachment to the ring is illustrative only and is not meant to be limiting. Substituent Z', as shown in the Schemes, represents the substituent Z as defined hereinabove or a protected precursor thereof.

These reactions may be employed in a linear sequence to provide the compounds of the invention or they may be used to synthesize fragments which are subsequently joined by the alkylation reactions described in the Schemes.

Synopsis of Schemes 1–20

The requisite intermediates are in some cases commercially available, or can be prepared according to literature procedures, for the most part. In Scheme 1, for example, the synthesis of N-protected substituted piperazines is outlined. Boc-protected amino acids I, available commercially or by procedures known to those skilled in the art, can be coupled to N-benzyl amino acid esters using a variety of dehydrating agents such as DCC (dicyclohexycarbodiimide) or EDC-HCl (1-ethyl-3-(3-dimethylaminopropyl)carbodiimide hydrochloride) in a solvent such as methylene chloride, chloroform, dichloroethane, or dimethylformamide. The product II is then deprotected with acid, for example hydrogen chloride in chloroform or ethyl acetate, or trifluoroacetic acid in methylene chloride, and cyclized under weakly basic conditions to give the diketopiperazine III. Reduction of III with lithium aluminum hydride in a refluxing ether gives the piperazine IV, which is protected as the Boc derivative V. The N-benzyl group can be cleaved under standard conditions of hydrogenation, e.g., 10% palladium on carbon at 60 psi hydrogen on a Parr apparatus for 24–48 h. The product VI can be reacted with a suitably substituted carboxylic acid to provide the piperazine VII (Scheme 2); a final acid deprotection as previously described gives the intermediate VIII (Scheme 2). The intermediate VIII can itself be reductively alkylated with a variety of aldehydes, such as IX. The aldehydes can be prepared by standard procedures, such as that described by O. P. Goel, U. Krolls, M. Stier and S. Kesten in *Organic Syntheses*, 1988, 67, 69–75, from the appropriate amino acid (Scheme 3). The reductive alkylation can be accomplished at pH 5–7 with a variety of reducing agents, such as sodium triacetoxyborohydride or sodium cyanoborohydride in a solvent such as dichloroethane, methanol or dimethylformamide. The product X can be deprotected to give the final compounds XI with trifluoroacetic acid in methylene chloride. The final product XI is isolated in the salt form, for example, as a trifluoroacetate, hydrochloride or acetate salt, among others. The product diamine XI can further be selectively protected to obtain XII, which can subsequently be reductively alkylated with a second aldehyde to obtain XIII. Removal of the protecting group, and conversion to cyclized products such as the dihydroimidazole XV can be accomplished by literature procedures.

As shown in Scheme 4, the piperazine intermediate VIII can be reductively alkylated with other aldehydes such as 1-trityl-4-imidazolyl-carboxaldehyde or 1-trityl-4-imidazolylacetaldehyde, to give products such as XVI. The trityl protecting group can be removed from XVI to give XVII, or alternatively, XVI can first be treated with an alkyl halide then subsequently deprotected to give the alkylated imidazole XVIII. Alternatively, the intermediate VIII can be acylated or sulfonylated by standard techniques.

Incorporation of a hydroxyl moiety on the sidechain carbon alpha to the amide carbonyl of compounds of the formula XVIII can be accomplished as illustrated in Scheme 5. A suitably substituted primary alcohol XIX undergoes a one carbon homologation, via a Swern oxidation, nitrile addition and hydrolysis, to provide the substituted hydroxyacetic acid XX. The trifluoromethyl ketal is formed and reacted with the previously described protected piperazine VI to provide, following deprotection, the intermediate XXI. Intermediate XXI can undergo a variety of reactions at its unsubstituted nitrogen. For example, treatment of XXI with a suitably substituted imidazolylmethyl halide to provide the instant compound XXII.

Scheme 6 illustrates incorporation of an arylalkoxycarbonyl or heteroarylalkoxycarbonyl moiety onto the piperazine nitrogen. Thus a suitably substituted alcohol XXIII is reacted with nitrophenylchloroformate to provide the intermediate XXIV, which is reacted with a suitably substituted piperazine to provide the instant compound XXV. An analogous reaction sequence alternatively provides the corresponding aminocarbonyl substitution on the piperazine nitrogen, as shown in Scheme 7.

Scheme 8 illustrates the preparation of compounds analogous to compound XXI wherein the alcohol utilized in the first step is a suitably substituted phenol. The scheme also illustrates the incorporation of an indole moiety for the substituent W in place of the preferred benzylimidazolyl moiety.

Scheme 9 illustrates synthesis of an instant compound wherein a non-hydrogen $R^{9b}$ is incorporated in the instant compound. Thus, a readily available 4-substituted imidazole XXVI may be selectively iodinated to provide the 5-iodoimidazole XXVII. That imidazole may then be protected and coupled to a suitably substituted benzyl moiety to provide intermediate XXVIII. Attachment of the imidazolyl nitrogen via an ethyl linker to the piperazine nitrogen of intermediate XXI, described above, provides the instant compound XXIX.

Compounds of the instant invention wherein the $A^1(CR^{1a}_2)_nA^2(CR^{1a}_2)_n$ linker is oxygen may be synthesized by methods known in the art, for example as shown in Scheme 10. The suitably substituted phenol XXX may be reacted with methyl N-(cyano)methanimidate to provide the 4-phenoxyimidazole XXI. After selective protection of one of the imidazolyl nitrogens, the intermediate XXXII can undergo alkylation reactions as described for the benzylimidazoles in Scheme 8.

If the piperazine VIII is reductively alkylated with an aldehyde which also has a protected hydroxyl group, such as XXXIII in Scheme 11, the protecting groups can be subsequently removed to unmask the hydroxyl group. The Boc protected amino alcohol XXXIV can then be utilized to synthesize 2-aziridinylmethylpiperazines such as XXXV.

Reaction Scheme 12 provides an illustrative example of the synthesis of compounds of the instant invention wherein the substituents $R^2$ and $R^3$ are combined to form —$(CH_2)_u$—. For example, 1-aminocyclohexane-1-carboxylic acid XLV can be converted to the spiropiperazine XLVI essentially according to the procedures outlined in Schemes 1 and 2. The piperazine intermediate XLVI can be deprotected as before, and carried on to final products as described in Schemes 3–8. It is understood that reagents utilized to provide the imidazolylalkyl substituent may be readily replaced by other reagents well known in the art and readily available to provide other N-substituents on the piperazine.

Amino acids of the general formula LI which have a sidechain not found in natural amino acids may be prepared by the reactions illustrated in Scheme 13 starting with the readily prepared imine LII.

Schemes 14–18 illustrate syntheses of suitably substituted aldehydes useful in the syntheses of the instant compounds wherein the variable W is present as a pyridyl moiety. Similar synthetic strategies for preparing alkanols that incorporate other heterocyclic moieties for variable W are also well known in the art. For example, Scheme 18 illustrates the preparation of the corresponding quinoline aldehyde.

Scheme 19 depicts a general method for synthesizing a key intermediate useful in the preparation of preferred embodiments of the instant invention wherein V is phenyl and W is imidazole. A piperazine moiety can be readily added to this benzyl-imidazole intermediate as set forth in Scheme 20.

SCHEME 1

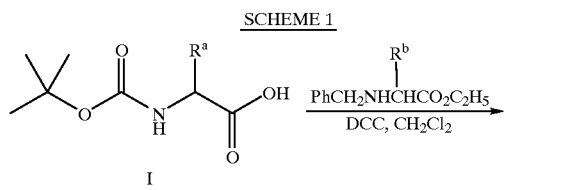

I

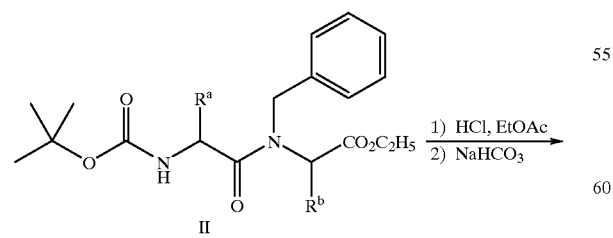

II

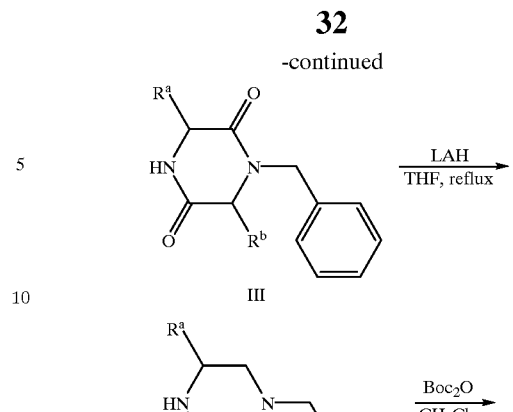

III

IV

V

VI

SCHEME 2

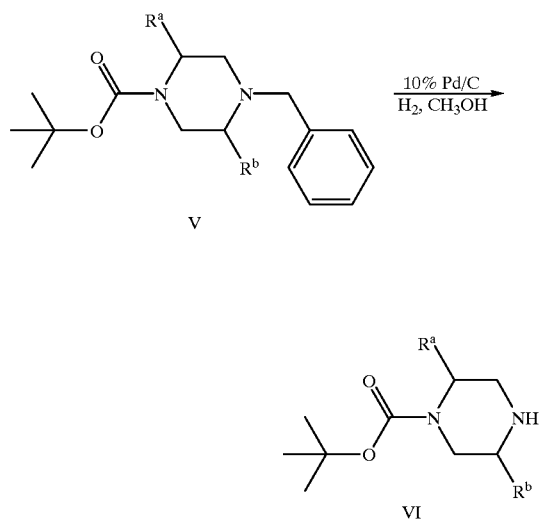

VI

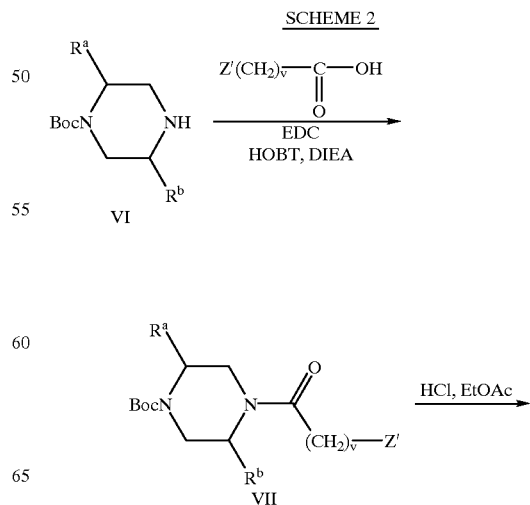

VII

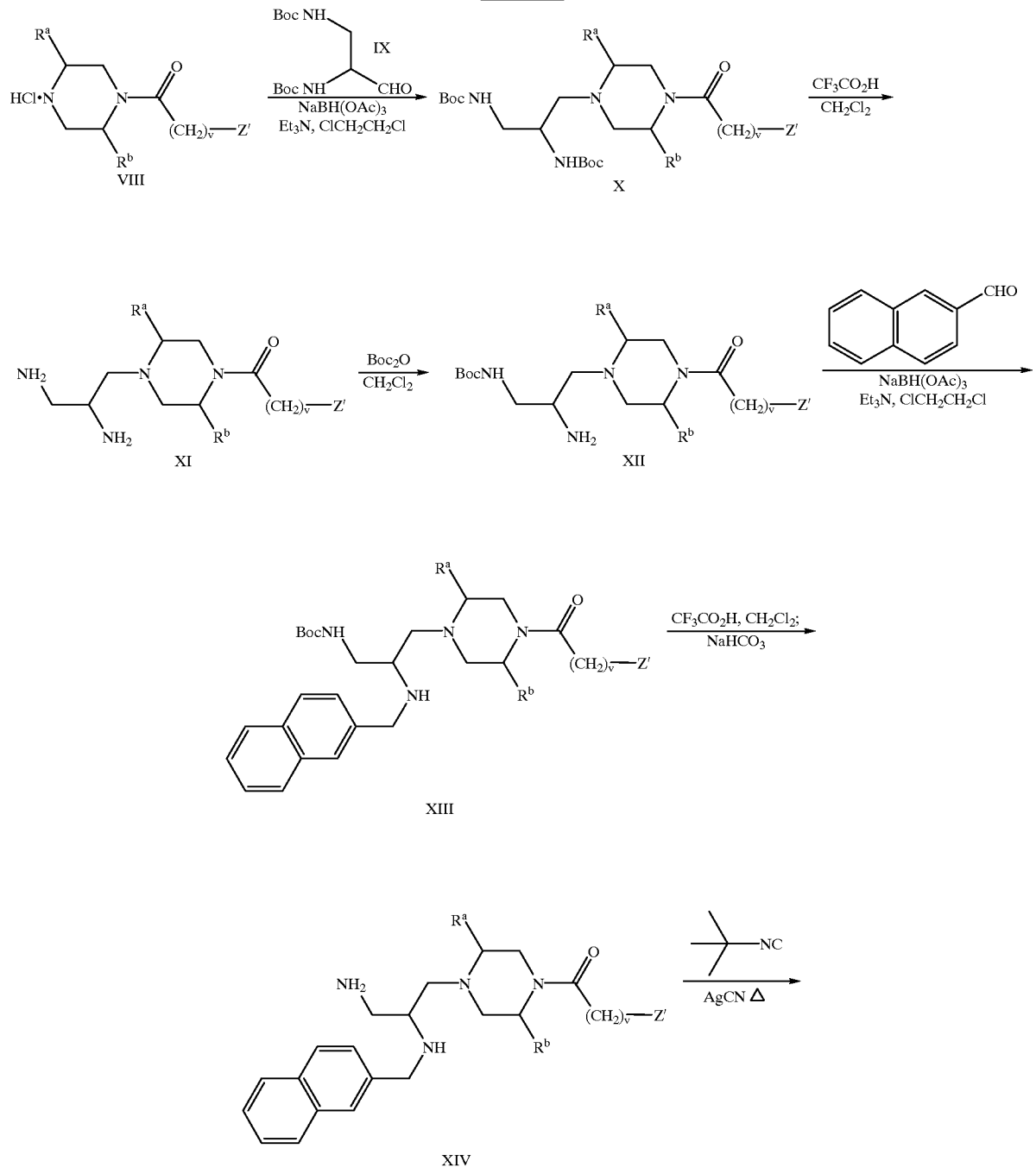

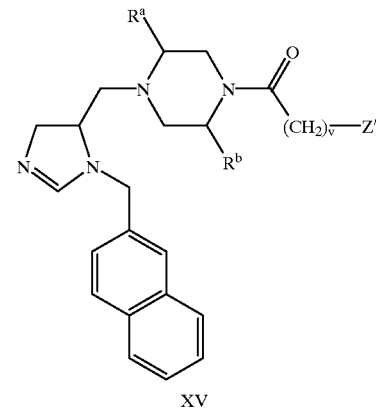
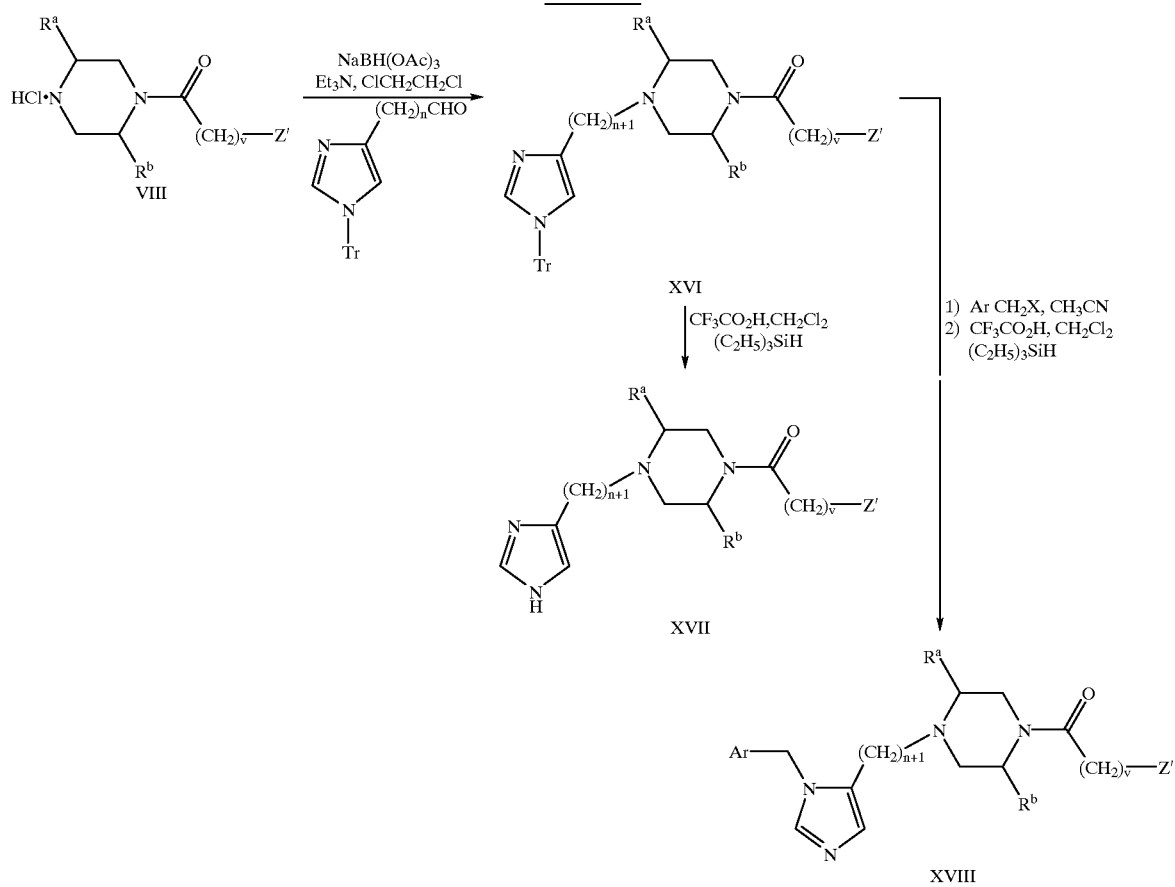
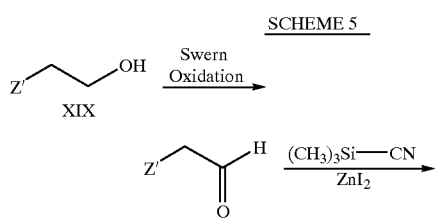
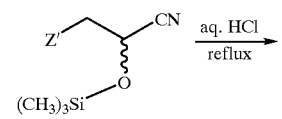

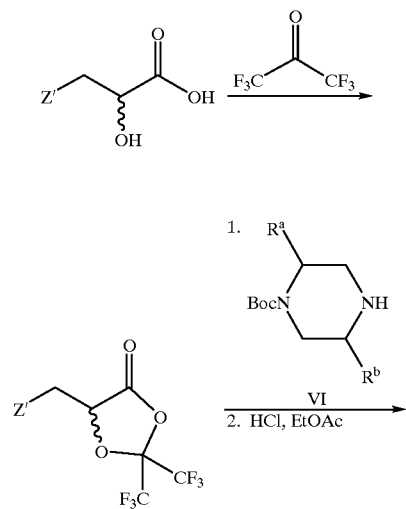
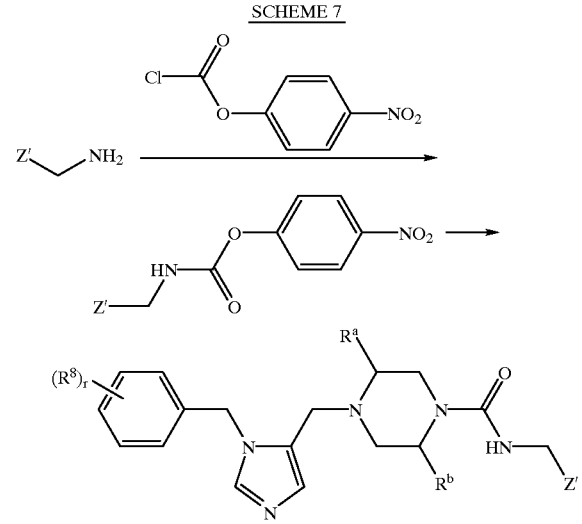
SCHEME 7
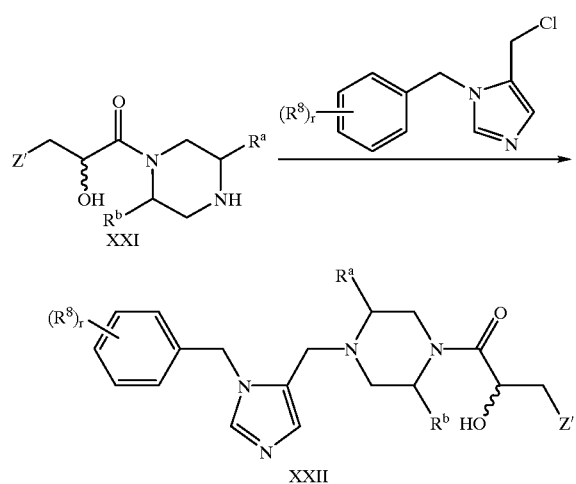
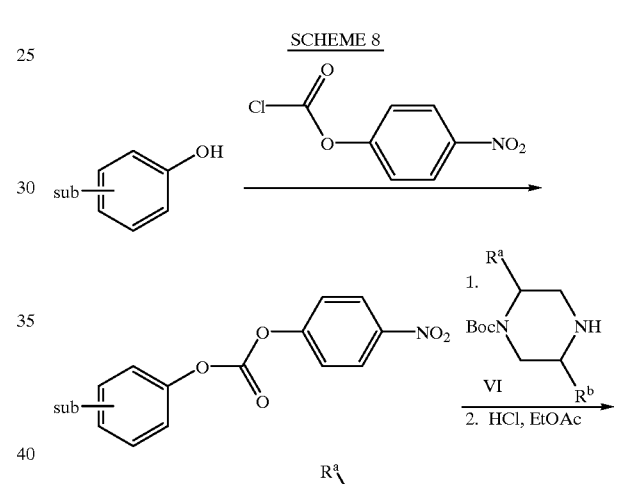
SCHEME 8
SCHEME 6
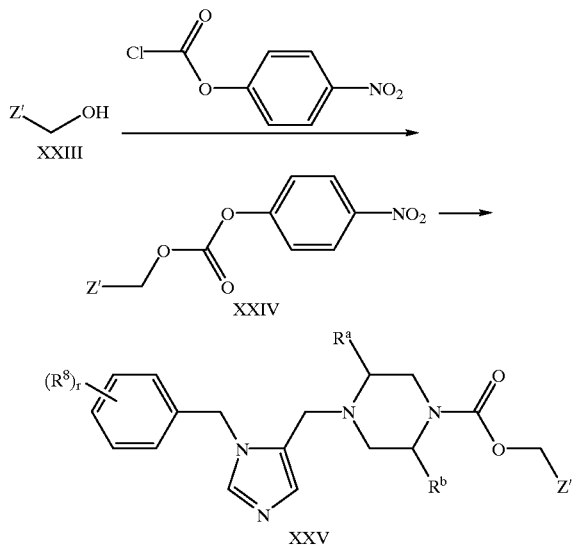
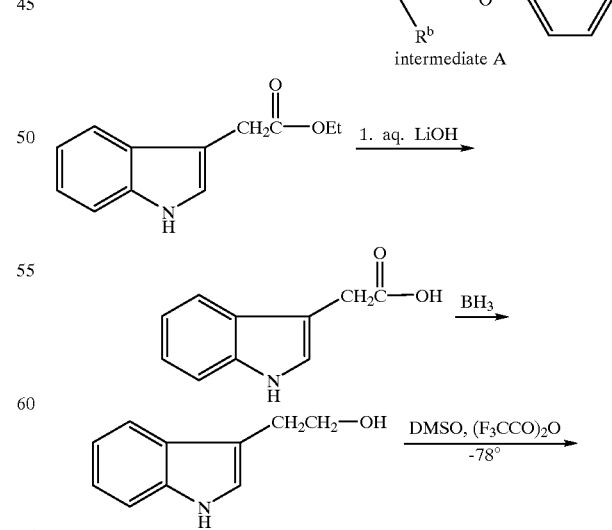

-continued
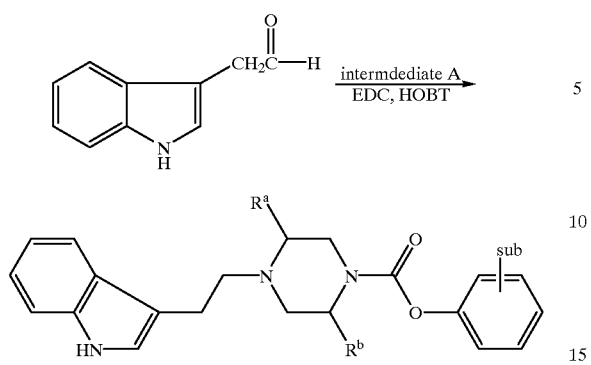
SCHEME 9
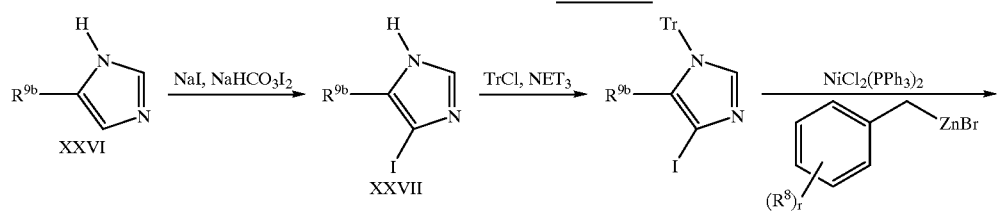
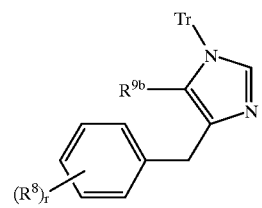
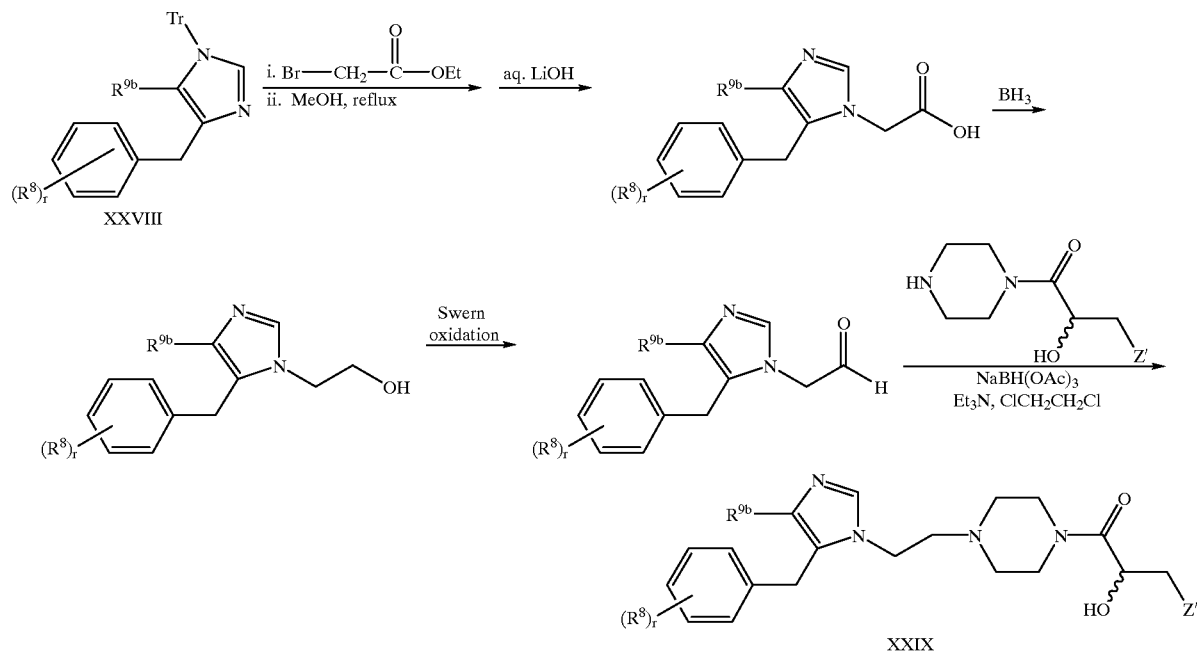

SCHEME 10
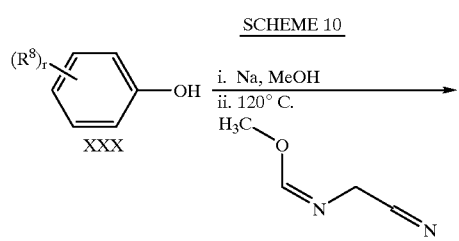 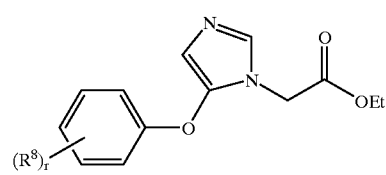
SCHEME 11
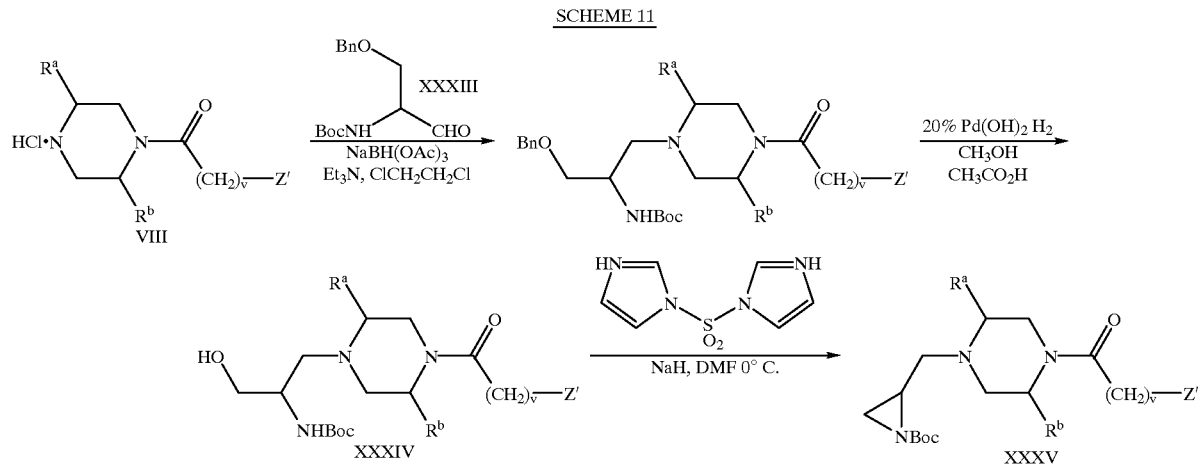
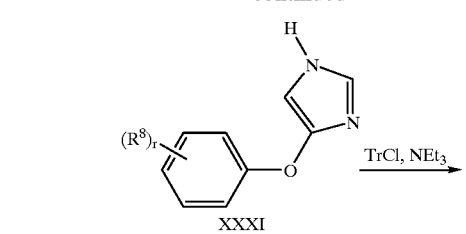 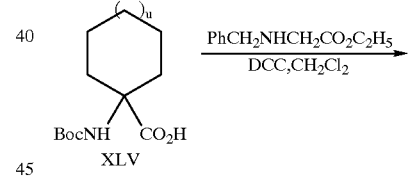
SCHEME 12
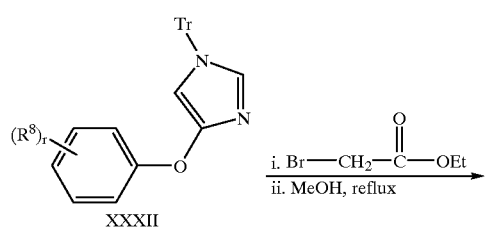 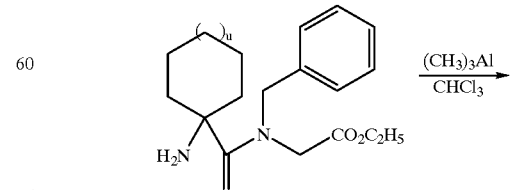

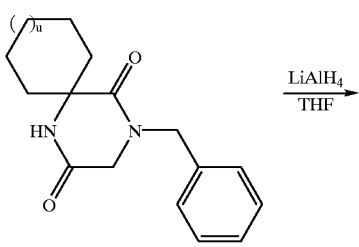
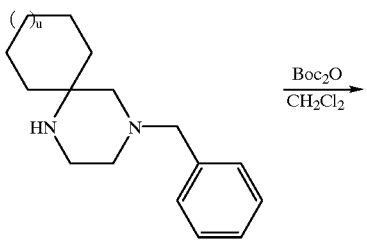
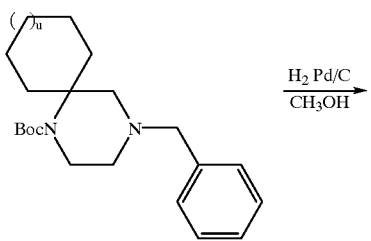
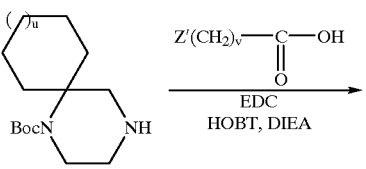
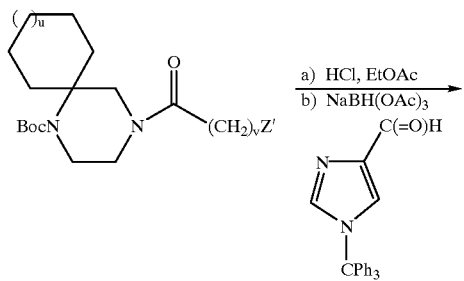
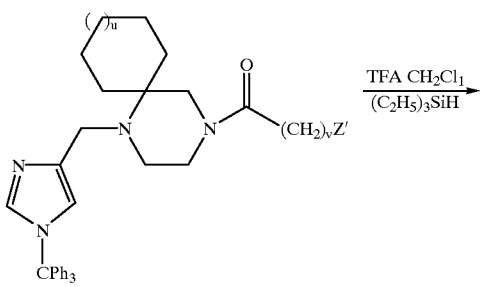
XLVI
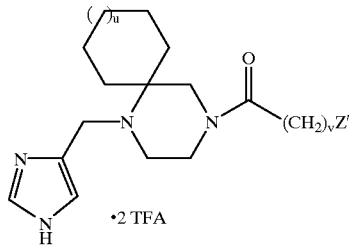
•2 TFA
SCHEME 13
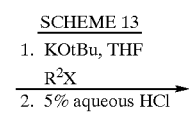
LII
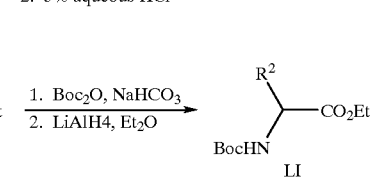
SCHEME 14
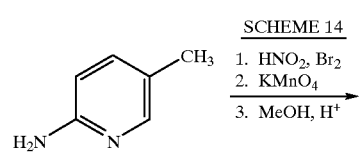
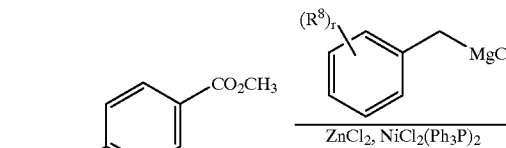
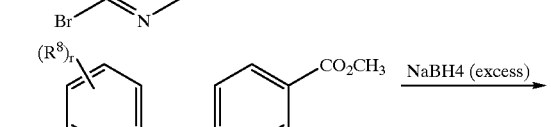
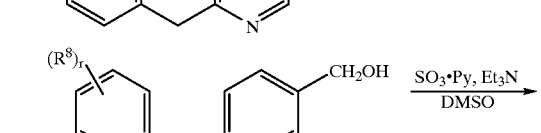
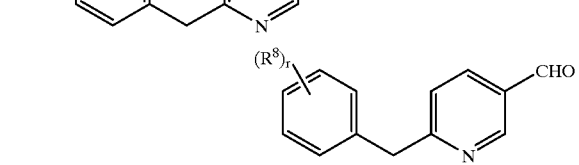
SCHEME 15
1. EtO(CO)Cl
2. 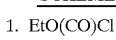
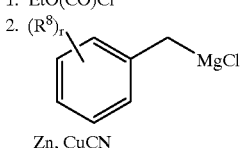
3. S, xylene, heat

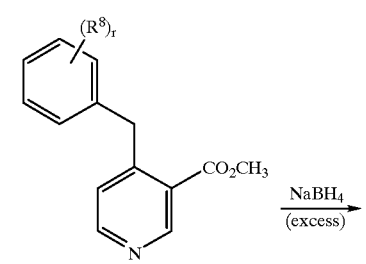
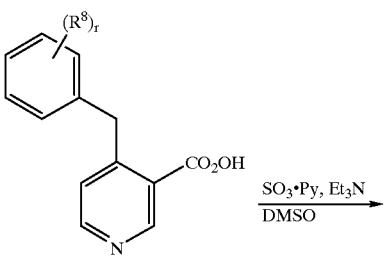
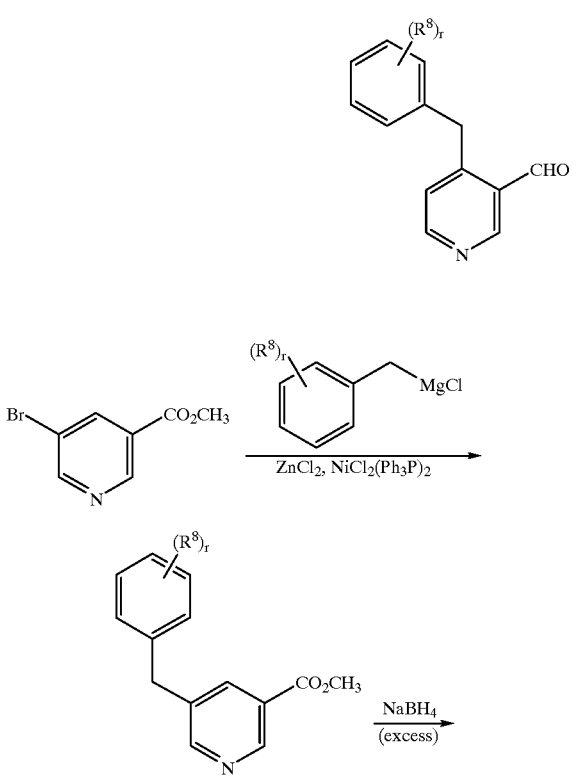
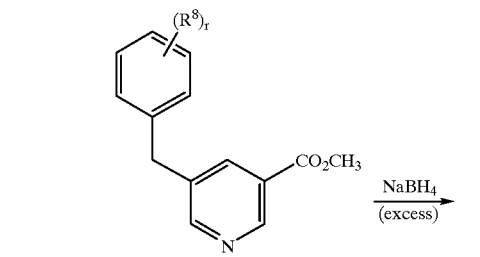
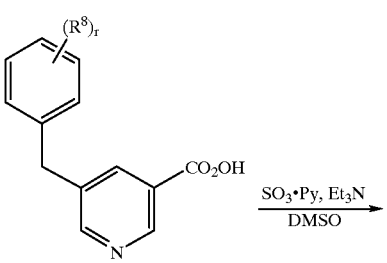
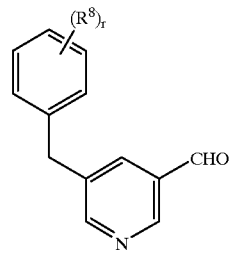
SCHEME 16
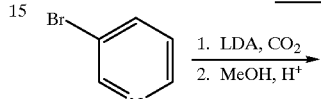
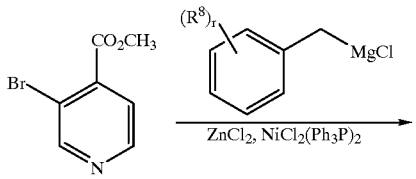
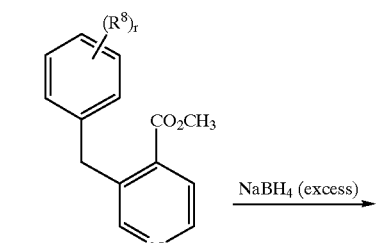
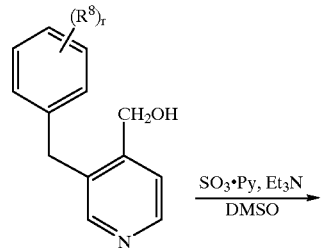
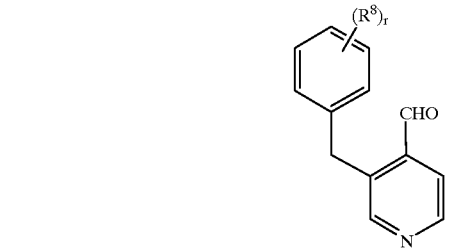
SCHEME 17
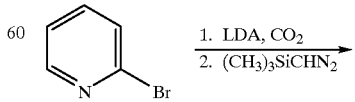

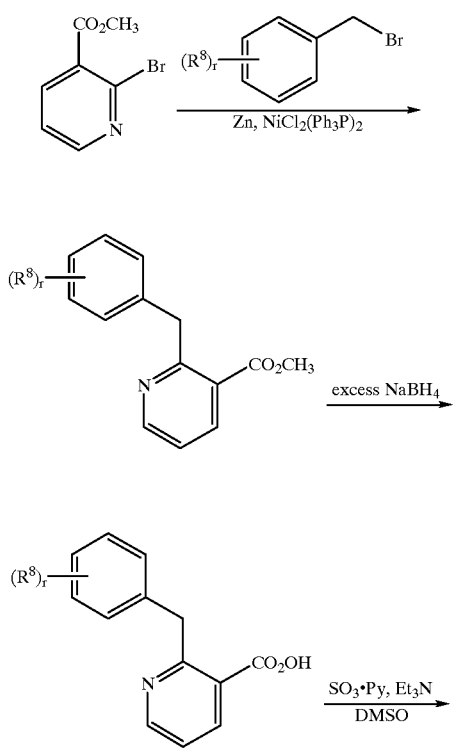
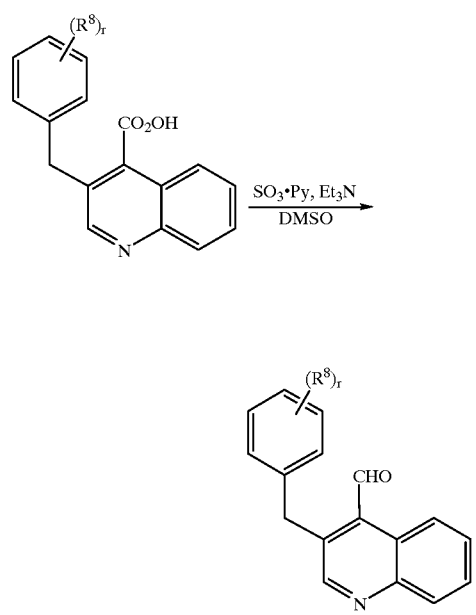
SCHEME 18
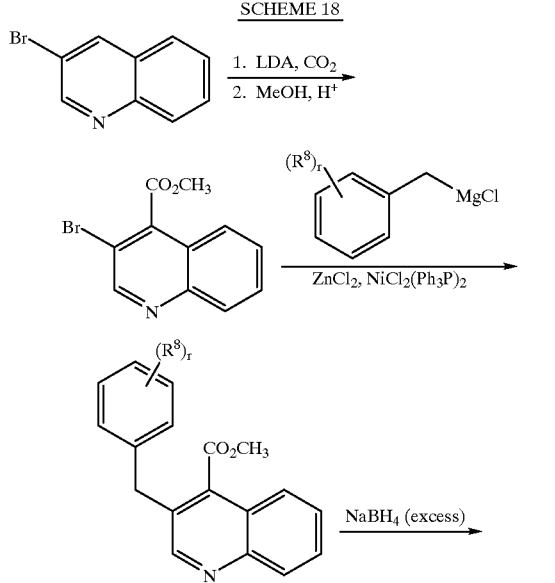
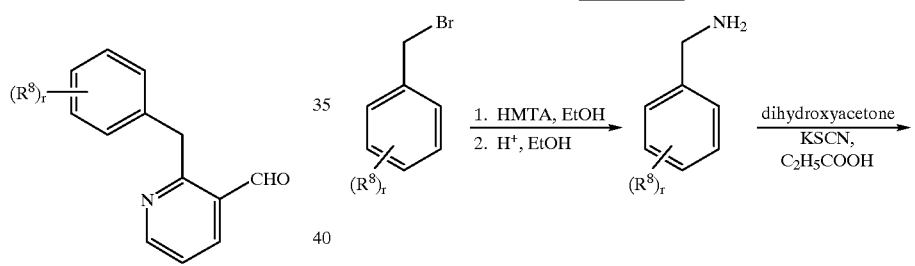
SCHEME 19
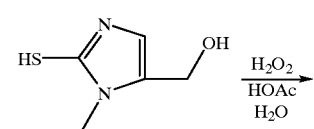
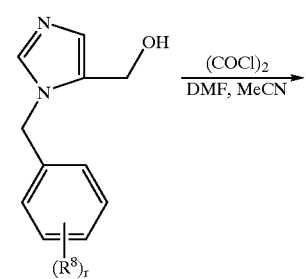

-continued

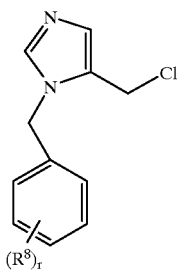

The instant compounds may also be useful in the treatment of certain viral infections, in particular in the treatment of hepatitis delta and related viruses (J. S. Glenn et al. Science, 256:1331–1333 (1992).

The compounds of the instant invention are also useful in the prevention of restenosis after percutaneous transluminal coronary angioplasty by inhibiting neointimal formation (C. Indolfi et al. Nature medicine, 1:541–545(1995).

The instant compounds may also be useful in the treatment and prevention of polycystic kidney disease (D. L. Schaffner et al. American Journal of Pathology, 142:1051–1060 (1993) and B. Cowley, Jr. et al.FASEB Journal, 2:A3160 (1988)).

SCHEME 20

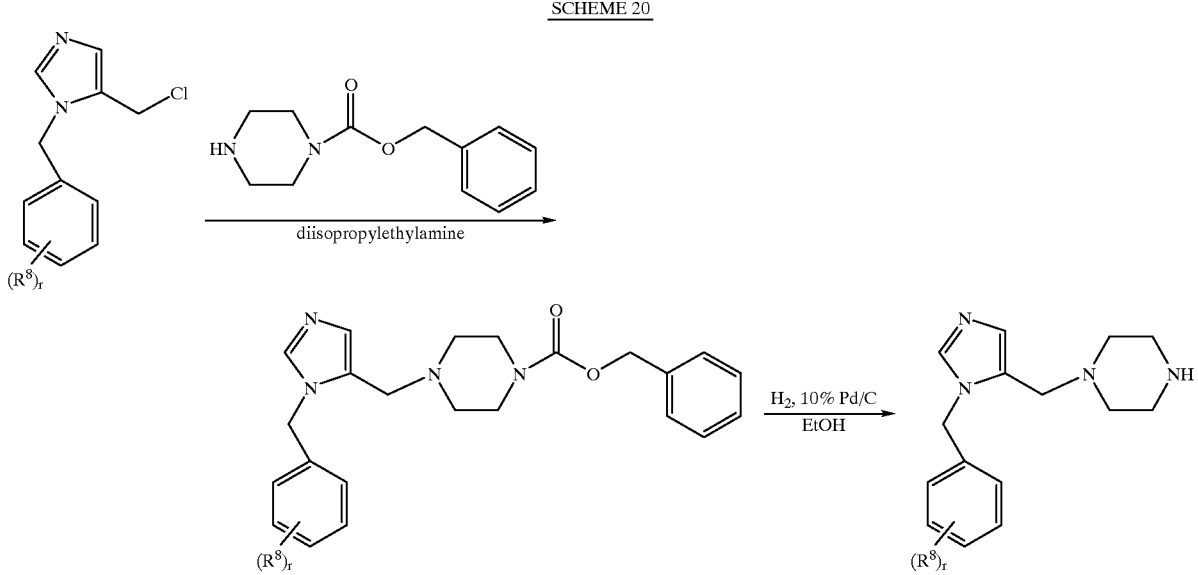

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, src, abl, lck, fyn) or by other mechanisms.

The compounds of the instant invention inhibit prenyl-protein transferase and the prenylation of the oncogene protein Ras. The instant compounds may also inhibit tumor angiogenesis, thereby affecting the growth of tumors (J. Rak et al. Cancer Research, 55:4575–4580 (1995)). Such anti-angiogenesis properties of the instant compounds may also be useful in the treatment of certain forms of vision deficit related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, a component of NF-1 is a benign proliferative disorder.

The instant compounds may also be useful for the treatment of fungal infections.

The instant compounds may also be useful as inhibitors of proliferation of vascular smooth muscle cells and therefore useful in the prevention and therapy of arteriosclerosis and diabetic vascular pathologies.

The compounds of this invention may be administered to mammals, preferably humans, either alone or, preferably, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula A may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula A are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

As used herein, the term "composition" is intended to encompass a product comprising the specified ingredients in the specific amounts, as well as any product which results, directly or indirectly, from combination of the specific ingredients in the specified amounts.

When a compound according to this invention is administered into a human subject, the daily dosage will normally be determined by the prescribing physician with the dosage generally varying according to the age, weight, sex and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention may also be co-administered with other well known therapeutic agents that are selected for their particular usefulness against the condition that is being treated. For example, the compounds of the instant invention may also be co-administered with other well known cancer therapeutic agents that are selected for their particular usefulness against the condition that is being treated. Included in such combinations of therapeutic agents are combinations of the instant prenyl-protein transferase inhibitors and an antineoplastic agent. It is also understood that such a combination of antineoplastic agent and inhibitor of prenyl-protein transferase may be used in conjunction with other methods of treating cancer and/or tumors, including radiation therapy and surgery.

Examples of an antineoplastic agent include, in general, microtubule-stabilizing agents (such as paclitaxel (also known as Taxol®), docetaxel (also known as Taxotere®), epothilone A, epothilone B, desoxyepothilone A, desoxyepothilone B or their derivatives); microtubule-disruptor agents; alkylating agents, anti-metabolites; epidophyllotoxin; an antineoplastic enzyme; a topoisomerase inhibitor; procarbazine; mitoxantrone; platinum coordination complexes; biological response modifiers and growth inhibitors; hormonal/anti-hormonal therapeutic agents and haematopoietic growth factors.

Example classes of antineoplastic agents include, for example, the anthracycline family of drugs, the vinca drugs, the mitomycins, the bleomycins, the cytotoxic nucleosides, the taxanes, the epothilones, discodermolide, the pteridine family of drugs, diynenes and the podophyllotoxins. Particularly useful members of those classes include, for example, doxorubicin, carminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podo-phyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, cisplatin, carboplatin, cyclophosphamide, bleomycin, tamoxifen, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

The preferred class of antineoplastic agents is the taxanes and the preferred antineoplastic agent is paclitaxel.

Radiation therapy, including x-rays or gamma rays which are delivered from either an externally applied beam or by implantation of tiny radioactive sources, may also be used in combination with the instant inhibitor of prenyl-protein transferase alone to treat cancer.

Additionally, compounds of the instant invention may also be useful as radiation sensitizers, as described in WO 97/38697, published on Oct. 23, 1997, and herein incorporated by reference.

The instant compounds may also be useful in combination with other inhibitors of parts of the signaling pathway that links cell surface growth factor receptors to nuclear signals initiating cellular proliferation. Thus, the instant compounds may be utilized in combination with a compound which has Raf antagonist activity. The instant compounds may also be co-administered with compounds that are selective inhibitors of farnesyl-protein transferase, dual inhibitors of farnesyl-protein transferase and geranylgeranylprotein transferase type I or selective inhibitors of geranylgeranyl-protein transferase type I. Such a selective inhibitor or dual inhibitor may be an inhibitor that is competitive with the binding of the CAAX-containing protein substrate of farnesyl-protein transferase or may be farnesyl pyrophosphate competitive inhibitors.

In particular, the compounds disclosed in the following patents and publications may be useful as farnesyl pyrophosphate-competitive inhibitor component of the instant composition: U.S. Ser. Nos. 08/254,228 and 08/435,047. Those patents and publications are incorporated herein by reference.

In practicing methods of this invention, which comprise administering, simultaneously or sequentially or in any order, two or more of a protein substrate-competitive inhibitor and a prenyl pyrophosphate-competitive inhibitor, such administration can be orally or parenterally, including intravenous, intramuscular, intraperitoneal, subcutaneous, rectal and topical routes of administration. It is preferred that such administration be orally. It is more preferred that such administration be orally and simultaneously. When the protein substrate-competitive inhibitor and a prenyl pyrophosphate-competitive inhibitor are administered sequentially, the administration of each can be by the same method or by different methods.

The instant compounds may also be useful in combination with an integrin antagonist for the treatment of cancer, as described in U.S. Ser. No. 09/055,487, filed Apr. 6, 1998, which is incorporated herein by reference.

As used herein the term an integrin antagonist refers to compounds which selectively antagonize, inhibit or counteract binding of a physiological ligand to an integrin(s) that is involved in the regulation of angiogenisis, or in the growth and invasiveness of tumor cells. In particular, the term refers to compounds which selectively antagonize, inhibit or counteract binding of a physiological ligand to the $\alpha v \beta 3$ integrin, which selectively antagonize, inhibit or counteract binding of a physiological ligand to the $\alpha v \beta 5$ integrin, which antagonize, inhibit or counteract binding of a physiological ligand to both the $\alpha v \beta 3$ integrin and the $\alpha v \beta 5$ integrin, or which antagonize, inhibit or counteract the activity of the particular integrin(s) expressed on capillary endothelial cells. The term also refers to antagonists of the $\alpha v \beta 6$, $\alpha v \beta 8$, $\alpha 1 \beta 1$, $\alpha 2 \beta 1$, $\alpha 5 \beta 1$, $\alpha 6 \beta 1$ and $\alpha 6 \beta 4$ integrins. The term also refers to antagonists of any combination of $\alpha v \beta 3$, $\alpha v \beta 5$, $\alpha v \beta 6$, $\alpha v \beta 8$, $\alpha 2 \beta 1$, $\alpha 2 \beta 1$, $\alpha 5 \beta 1$, $\alpha 6 \beta 1$ and $\alpha 6 \beta 4$ integrins. The instant compounds may also be useful with other agents that inhibit angiogenisis and thereby inhibit the growth and invasiveness of tumor cells, including, but not limited to angiostatin and endostatin.

Similarly, the instant compounds may be useful in combination with agents that are effective in the treatment and prevention of NF-1, restenosis, polycystic kidney disease, infections of hepatitis delta and related viruses and fungal infections.

If formulated as a fixed dose, such combination products employ the combinations of this invention within the dosage range described below and the other pharmaceutically active agent(s) within its approved dosage range. Combinations of the instant invention may alternatively be used sequentially with known pharmaceutically acceptable agent(s) when a multiple combination formulation is inappropriate.

EXAMPLES

Examples provided are intended to assist in a further understanding of the invention. Particular materials employed, species and conditions are intended to be further illustrative of the invention and not limitative of the reasonable scope thereof.

Example 1

Preparation of 1-(4-cyanobenzyl)-5-chloromethyl Imidazole HCl Salt

Step 1

Preparation of 4-Cyanobenzylamine

Method 1 (Hydrochloride Salt)

A 72 liter vessel was charged with 190 proof ethanol (14.4 L) followed by the addition of 4-cyanobenzylbromide (2.98 kg) and HMTA (2.18 kg) at ambient temperature. The mixture was heated to about 72–75° C. over about 60 min. On warming, the solution thickens and additional ethanol (1.0 liter) was added to facilitate stirring. The batch was aged at about 72–75° C. for about 30 min.

The mixture was allowed to cool to about 20° C. over about 60 min, and HCl gas (2.20 kg) was sparged into the slurry over about 4 hours during which time the temperature rose to about 65° C. The mixture was heated to about 70–72° C. and aged for about 1 hour. The slurry was cooled to about 30° C. and ethyl acetate (22.3 L) added over about 30 min. The slurry was cooled to about −5° C. over about 40 min and aged at about −3 to about −5° C. for about 30 min. The mixture was filtered and the crystalline solid was washed with chilled ethyl acetate (3×3 L). The solid was dried under a $N_2$ stream for about 1 hour before charging to a 50 liter vessel containing water (5.5 L). The pH was adjusted to about 10–10.5 with 50% NaOH (4.0 kg) maintaining the internal temperature below about 30° C. At about 25° C., methylene chloride (2.8 L) was added and stirring continued for about 15 min. The layers were allowed to settle and the lower organic layer was removed. The aqueous layer was extracted with methylene chloride (2×2.2 L). The combined organic layers were dried over potassium carbonate (650 g). The carbonate was removed via filtration and the filtrate concentrated in vacuo at about 25° C. to give a free base as a yellow oil.

The oil was transferred to a 50 liter vessel with the aid of ethanol (1.8 L). Ethyl acetate (4.1 L) was added at about 25° C. The solution was cooled to about 15° C. and HCl gas (600 g) was sparged in over about 3 hours, while keeping batch temperature below about 40° C. At about 20–25° C., ethyl acetate (5.8 L) was added to the slurry, followed by cooling to about −5° C. over about 1 hour. The slurry was aged at about −5° C. for about 1 hour and the solids isolated via filtration. The cake was washed with a chilled mixture of EtOAc/EtOH (9:1 v/v) (1×3.8 L), then the cake was washed with chilled EtOAc (2×3.8 L). The solids were dried in vacuo at about 25° C. to provide the above-titled compound.

$^1$H NMR (250 MHz, $CDCl_3$): δ7.83–7.79 (d, 2H), 7.60–7.57 (d, 2H), 4.79 (s, 2H), 4.25 (s, 2H); $^{13}$C NMR (62.9 MHz, $CDCl_3$): δ149.9, 139.8, 134.2, 131.2, 119.7, 113.4, 49.9, 49.5, 49.2, 48.8, 48.5, 48.2, 43.8.

Method 2 (Phosphate Salt)

A slurry of HMTA in 2.5 L EtOH was added gradually over about 30 min to about 60 min to a stirred slurry of cyanobenzyl-bromide in 3.5 L EtOH and maintained at about 48–53° C. with heating & cooling in a 22 L neck flask (small exotherm). Then the transfer of HMTA to the reaction mixture was completed with the use of 1.0 L EtOH. The reaction mixture was heated to about 68–73° C. and aged at about 68–73° C. for about 90 min. The reaction mixture was a slurry containing a granular precipitate which quickly settled when stirring stopped.

The mixture was cooled to a temperature of about 50° C. to about 55° C. Propionic acid was added to the mixture and the mixture was heated and maintained at a temperature of about 50° C. to about 55° C. Phosphoric acid was gradually added over about 5 min to about 10 min, maintaining the reaction mixture below about 65° C. to form a precipitate-containing mixture. Then the mixture was gradually warmed to about 65° C. to about 70° C. over about 30 min and aged at about 65° C. to about 70° C. for about 30 min. The mixture was then gradually cooled to about 20–25° C. over about 1 hour and aged at about 20–25° C. for about 1 hour.

The reaction slurry was then filtered. The filter cake was washed four times with EtOH, using the following sequence, 2.5 L each time. The filter cake was then washed with water five times, using 300 mL each time. Finally, the filter cake was washed twice with MeCN (1.0 L each time) and the above identified compound was obtained.

Step 2

Preparation of 1-(4-Cyanobenzyl)-2-Mercapto-5-Hydroxymethylimidazole

7% water in acetonitrile (50 mL) was added to a 250 mL roundbottom flask. Next, an amine phosphate salt (12.49 g), prepared as described in Step 1, was added to the flask. Next potassium thiocyanate (6.04 g) and dihydroxyacetone (5.61 g) was added. Lastly, propionic acid (10.0 mL) was added. Acetonitrile/water 93:7 (25 mL) was used to rinse down the sides of the flask. This mixture was then heated to 60° C., aged for about 30 minutes and seeded with 1% thioimidazole. The mixture was then aged for about 1.5 to about 2 hours at 60° C. Next, the mixture was heated to 70° C., and aged for 2 hours. The temperature of the mixture was then cooled to room temperature and was aged overnight. The thioimidazole product was obtained by vacuum filtration. The filter cake was washed four times acetonitrile (25 mL each time) until the filtrates became nearly colorless. Then the filter cake was washed three times with water (approximately 25–50 mL each time) and dried in vacuo to obtain the above-identified compound.

Step 3

Preparation of 1-(4-Cyanobenzyl)-5-Hydroxymethylimidazole

A 1 L flask with cooling/heating jacket and glass stirrer (Lab-Max) was charged with water (200 mL) at 25° C. The thioimidazole (90.27 g), prepared as described in Step 2, was added, followed by acetic acid (120 mL) and water (50 mL) to form a pale pink slurry. The reaction was warmed to 40° C. over 10 minutes. Hydrogen peroxide (90.0 g) was added slowly over 2 hours by automatic pump maintaining a temperature of 35–45° C. The temperature was lowered to 25° C. and the solution aged for 1 hour.

The solution was cooled to 20° C. and quenched by slowly adding 20% aqueous $Na_2SO_3$ (25 mL) maintaining the temperature at less than 25° C. The solution was filtered through a bed of DARCO G-60 (9.0 g) over a bed of SolkaFlok (1.9 g) in a sintered glass funnel. The bed was washed with 25 mL of 10% acetic acid in water.

The combined filtrates were cooled to 15° C. and a 25% aqueous ammonia was added over a 30 minute period, maintaining the temperature below 25° C., to a pH of 9.3. The yellowish slurry was aged overnight at 23° C. (room temperature). The solids were isolated via vacuum filtration. The cake (100 mL wet volume) was washed with 2×250 mL 5% ammonia (25%) in water, followed by 100 ML of ethyl acetate. The wet cake was dried with vacuum/$N_2$ flow and the above-titled compound was obtained.

$^1$H NMR (250 MHz, CDCl$_3$): δ7.84–7.72 (d, 2H), 7.31–7.28 (d, 2H), 6.85 (s, 1H), 5.34 (s, 2H), 5.14–5.11 (t, 1H), 4.30–4.28 (d, 2H), 3.35 (s, 1H).

Step 4
Preparation of 1-(4-cyanobenzyl)-5-chloromethyl Imidazole HCl Salt
Method 1

1-(4-Cyanobenzyl)-5-hydroxymethylimidazole (1.0 kg), prepared as described above in Step 3, was slurried with DMF (4.8 L) at 22° C. and then cooled to −5° C. Thionyl chloride (390 mL) was added dropwise over 60 min during which time the reaction temperature rose to a maximum of 9° C. The solution became nearly homogeneous before the product began to precipitate from solution. The slurry was warmed to 26° C. and aged for 1 h.

The slurry was then cooled to 5° C. and 2-propanol (120 mL) was added dropwise, followed by the addition of ethyl acetate (4.8 L). The slurry was aged at 5° C. for 1 h before the solids were isolated and washed with chilled ethyl acetate (3×1 L). The product was dried in vacuo at 40° C. overnight to provide the above-titled compound.

$^1$H NMR (250 MHz DMSO-d$_6$): δ9.44 (s, 1H), 7.89 (d, 2H, 8.3 Hz), 7.89 (s, 1H), 7.55 (d, 2H, 8.3 Hz), 5.70 (s, 2H), 4.93 (s, 2H). $^{13}$C NMR (75.5 MHz DMSO-d$_6$): δ$_c$ 139.7, 137.7, 132.7, 130.1, 128.8, 120.7, 118.4, 111.2, 48.9, 33.1.
Method 2

To an ice cold solution of dry acetonitrile (3.2 L, 15 L/Kg hydroxymethylimidazole) was added 99% oxalyl chloride (101 mL, 1.15 mol. 1.15 equiv.), followed by dry DMF (178 mL, 2.30 mol, 2.30 equiv.), at which time vigorous evolution of gas was observed. After stirring for about 5 to 10 min following the addition of DMF, solid hydroxymethylimidazole (213 g, 1.00 mol), prepared as described above in Step 3, was added gradually. After the addition, the internal temperature was allowed to warm to a temperature of about 23° C. to about 25° C. and stirred for about 1 to 3 hours. The mixture was filtered, then washed with dry acetonitrile (400 mL displacement wash, 550 mL slurry wash, and a 400 mL displacement wash). The solid was maintained under a $N_2$ atmosphere during the filtration and washing to prevent hydrolysis of the chloride by adventitious $H_2O$. This yielded the crystalline form of the chloromethylimidazole hydrochloride.

$^1$H NMR (250 MHz DMSO-d$_6$): δ9.44 (s, 1H), 7.89 (d, 2H, 8.3 Hz), 7.89 (s, 1H), 7.55 (d, 2H, 8.3 Hz), 5.70 (s, 2H), 4.93 (s, 2H). $^{13}$C NMR (75.5 MHz DMSO-d$_6$): δ$_c$ 139.7, 137.7, 132.7, 130.1, 128.8, 120.7, 118.4, 111.2, 48.9, 33.1.
Method 3

To an ice cold solution of dry DMF (178 mL, 2.30 mol, 2.30 equiv.) in dry acetonitrile (2.56 L, 12 L/Kg Hydroxymethylimidazole) was added oxalyl chloride (101 mL, 1.15 mol, 1.15 equiv). The heterogeneous mixture in the reagent vessel was then transferred to a mixture of hydroxymethylimidazole (213 g, 1.00 mol), prepared as described in Step 3 above, in dry acetonitrile (1.7 L, 8 L/Kg hydroxymethylimidazole). Additional dry acetonitrile (1.1–2.3 L, 5–11 L/Kg hydroxymethylimidazole) was added to the remaining solid Vilsmeier reagent in the reagent vessel. This, now nearly homogenous, solution was transferred to the reaction vessel at $T_i$≦+6° C. The reaction vessel temperature was warmed to a temperature of about 23° C. to about 25° C. and stirred for about 1 to 3 hours. The mixture was then cooled to 0° C. and aged 1 h. The solid was filtered and washed with dry, ice cold acetonitrile (400 mL displacement wash, 550 mL slurry wash, and a 400 mL displacement wash). The solid was maintained under a $N_2$ atmosphere during the filtration and washing to prevent hydrolysis of the chloride by adventitious $H_2O$. This yielded the crystalline form of the chloromethylimidazole hydrochloride.

Example 2
Preparation of 1-(4'-Cyanobenzyl)imidazol-5-ylmethyl Piperazine

Step 1
Preparation of 1-(4'-Cyanobenzyl)imidazol-5-ylmethyl Piperazine-4-carboxylic Acid Benzyl Ester To an acetonitrile solution of 1-(4'-cyanobenzyl)-5-chloromethylimidazole (7.45 mmol), prepared as described in Example 1, Step 4, and diisopropylethyl amine (22.4 mmol) was added 1-benzyl 1-piperazine carboxylate (10.4 mmol). This solution was stirred for 4.0 hours at 80° C. The product was isolated after silica column purification.

$^1$H-NMR (CDCl$_3$): δ7.65 (d, 2H); 7.55 (s, 1H); 7.38 (m, 5H); 7.15 (d, 2H); 7.0 (s, 1H); 5.3 (s, 2H); 5.1 (s, 1H); 3.4 (m, 4H); 3.3 (s, 2H); 2.3 (m, 4H).

Step 2
Preparation of 1-(4'-Cyanobenzyl)imidazol-5-ylmethyl Piperazine

The product from Step 1 (6.17 mmol) was dissolved in absolute ethanol followed by the introduction of 10% Pd/C catalyst then hydrogen under atmospheric pressure. The catalyst was removed via filtration through filter-aid and the product was isolated by removing the solvent under reduced pressure.

$^1$H-NMR (CD$_3$OD): δ7.8 (s, 1H); 7.75 (d, 2H); 7.3 (d, 2H); 6.9 (s, 1H); 5.45 (s, 2H); 3.3 (m, 4H); 2.6 (s, 2H); 2.3 (m, 4H).

Example 3
Preparation of 1-[1-(4'-Cyanobenzyl)imidazol-5-ylmethyl]-4-[1-phenyl-1-cyclopentylcarbonyl]piperazine Bis Hydrochloride 1-(4'-Cyanobenzyl)imidazol-5-ylmethyl piperazine (prepared as described in Example 2, Step 2), dissolved in DMF (25 mL), was treated with HOBT (450 mg, 2.47 mmol), EDC (560 mg. 2.47 mmol), 1-phenyl-1-cyclopentane carboxylic acid (420 mg, 2.2 mmol), and triethylamine (1.2 mL). The mixture was stirred at room temperature for 20 hours (pH-8). The mixture was partitioned between EtOAc and $H_2O$. The organic layer was washed twice with $H_2O$ and dried (Na$_2$SO$_4$). The solution was filtered and evaporated in vacuo. The crude product was chromatographed (2% MeOH in CHCl$_3$) on silica gel and then converted to the bis HCl salt to give the title compound.

FAB MS Calcd for $C_{28}H_{31}N_5O$ 454.5 (MH$^+$), found 454.3. Anal. Calcd for $C_{28}H_{31}N_5O$.2.2 HCl.0.40 EtOH: C, 62.61; H, 6.60; N, 12.53. Found: C, 62.64; H, 6.50; N, 12.68.

Example 4
Preparation of 1-[1-(4'-Cyanobenzyl)imidazol-5-ylmethyl]-4-[cyclohexylphenylacetyl]piperazine Using the appropriate starting materials, the method described in Example 3 was employed to prepare the title compound, except that conversion to the salt was omitted.

FAB MS Calcd for $C_{30}H_{35}N_5O$ 482.6 (MH$^+$), found 482.4. Anal. Calcd for $C_{30}H_{35}N_5O \cdot 0.25$ CHCl$_3$: C, 71.03; H, 6.95; N, 13.69. Found: C, 71.03; H, 7.10; N, 13.69.

Example 5
Preparation of 1-[1-(4'-Cyanobenzyl)imidazol-5-ylmethyl]-4-[1-(3-methoxyphenyl)-1-cyclopentylcarbonyl]piperazine Bis Hydrochloride

Step 1
Preparation of Methyl1-(3-methoxyphenyl)-1-cyclopentylcarboxylate

Lithium bis(trimethylsilyl)amide (1M in hexane; 22 mL, 22 mmol) was added slowly to a solution of methyl 3-methoxyphenylacetate (1.8 g, 10 mmol) in dry THF under Ar at −78° C. After stirring for ~½ hour, 1,4-dibromobutane (1.3 mL, 11 mmol) was added slowly and the reaction mixture was slowly warmed to room temperature over 6 hours. Stirring at room temperature was continued under Ar for 16 hours. The reaction mixture was quenched with sat. NH$_4$Cl and then partitioned between EtOAc and H$_2$O. The organic layer was washed twice with H$_2$O, brine, and dried (Na$_2$SO$_4$). The solution was filtered and evaporated in vacuo. The crude product was chromatographed (CHCl$_3$) to give the title compound as a nearly colorless oil.

EI MS Calcd for $C_{14}H_{18}O_3$ 234.2 (MH$^+$), found 234.1

Step 2
Preparation of 1-(3-Methoxyphenyl)-1-cyclopentanecarboxylic Acid

The ester from Step 1 (1.75 g, 7.5 mmol) dissolved in EtOH (15 mL)-H$_2$O (15 mL) was treated with sodium hydroxide (2.5 g, 62.5 mmol) and the solution was stirred at 60–65° for 20 hours. The reaction mixture was cooled, diluted with H$_2$O and extracted with EtOAc. The aqueous layer was cooled to ~10° C. and acidified with conc. HCl to pH~1. The product was extracted into EtOAc then washed with water and dried (Na$_2$SO$_4$). The solution was filtered and evaporated in vacuo to give the title compound.

FAB MS Caled for $C_{13}H_{16}O_3$ 221.2 (MH$^+$), found 221.3.

Step 3
Preparation of 1-[1-(4'-Cyanobenzyl)imidazol-5-ylmethyl]-4-[1-(3-methoxyphenyl)-1-cyclopentylcarbonyl]piperazine Bis Hydrochloride The title compound was prepared from the product from Step 2 using the procedure described in Example 3.

FAB HRMS exact mass Calcd for $C_{29}H_{33}N_5O_2$ 484.2707 (MH$^+$), found 484.2707. Anal Calcd for $C_{29}H_{33}N_5O_2 \cdot 0.20$ EtOH·2.45 HCl: C, 60.66; H, 6.35; N, 12.03. Found: C, 60.66; H, 6.20; N, 11.99.

Example 6
Preparation of 1-[1-(4'-Cyanobenzyl)imidazol-5-ylmethyl]-4-[1-(3-phenoxyphenyl)-1-cyclopentylcarbonyl]piperazine Bis Hydrochloride The title compound was prepared using the procedures described in Example 5, Steps 1–3, replacing methyl 3-methoxyphenylacetate with methyl 3-phenoxyphenylacetate.

FAB HRMS exact mass Calcd for $C_{34}H_{35}N_5O2$ 546.2855 (MH$^+$), found 546.2863. Anal. Calcd for $C_{34}H_{35}N_5O_2 \cdot 0.25$ EtOH·2.35 HCl: C, 64.45; H, 6.09; N, 10.90. Found: C, 64.44; H, 5.72; N, 10.54.

Example 7
Preparation of 1-[1-(4'-Cyano-3-fluorobenzyl)imidazol-5-ylmethyl]-4-[1-(3-hydroxyphenyl)-1-cyclohexylcarbonyl]piperazine

Step 1
Preparation of Methyl-1-[1-(3-methoxyphenyl)-1-cyclohexyl]carboxylate Using the appropriate starting materials, the method described in Example 5, Step 1, was employed to prepare the title compound.

Step 2
Preparation of 1-(3-Hydroxyphenyl)-1-cyclohexanecarboxylic Acid

The ester from Step 1 was dissolved in HOAc: 48% HBr (1:2) and the mixture was refluxed for 4 hours. The clear solution was evaporated in vacuo to provide title compound.

FAB MS Calcd for $C_{13}H_{16}O_3$ 221.1 (MH$^+$), found 221.1; (M-CO$_2$H) 175.1.

Step 3
Preparation of 4-(tert-Butyloxycarbonyl)-1-[1-(3-hydroxyphenyl-1-cyclohexylcarbonyl]-piperazine The title compound was prepared from the product from Step 2 and tert-butyloxycarbonyl piperazine using the procedure described in Example 4.

FAB MS Calcd for $C_{22}H_{32}N_2O_4$ 389.5 (MH$^+$), found 389.3 (M-tBu)=333.2.

Step 4
Preparation of 1-[1-(3-Hydroxyphenyl)-1-cyclohexylcarbonyl]piperazine Hydrochloride The carbamate from Step 3 was treated with EtOAc saturated with HCl at 0° C. for ½ hour. Evaporation in vacuo provided the title compound as a white powder.

FAB MS Calcd for $C_{17}H_{24}N_2O_2$ 289.3 (MH$^+$), found 289.1.

Step 5
Preparation of 1-(4-cyano-3-fluorobenzyl)-5-imidazolecarboxaldehyde

Step A
Preparation of 1-triphenylmethyl-4-(hydroxymethyl)-imidazole

To a solution of 4-(hydroxymethyl)imidazole hydrochloride (35.0 g, 260 mmol) in 250 mL of dry DMF at room temperature was added triethylamine (90.6 mL, 650 mmol). A white solid precipitated from the solution. Chlorotriphenylmethane (76.1 g, 273 mmol) in 500 mL of DMF was added dropwise. The reaction mixture was stirred for 20 hours, poured over ice, filtered, and washed with ice water. The resulting product was slurried with cold dioxane, filtered, and dried in vacuo to provide the titled product as a white solid which was sufficiently pure for use in the next step.

Step B
Preparation of 1-triphenylmethyl-4-(acetoxymethyl) imidazole

Alcohol from Step A (260 mmol, prepared above) was suspended in 500 mL of pyridine. Acetic anhydride (74 mL, 780 mmol) was added dropwise, and the reaction was stirred for 48 hours during which it became homogeneous. The solution was poured into 2 L of EtOAc, washed with water (3×1 L), 5% aq. HCl soln. (2×1 L), sat. aq. NaHCO$_3$, and brine, then dried (Na$_2$SO$_4$), filtered, and concentrated in vacuo to provide the crude product. The acetate was isolated as a white powder which was sufficiently pure for use in the next reaction.

61

Step C
Preparation of 4-cyano-3-fluorotoluene

To a degassed solution of 4-bromo-3-fluorotoluene (50.0 g, 264 mmol) in 500 mnL of DMF was added $Zn(CN)_2$ (18.6 g, 159 mmol) and $Pd(PPh_3)_4$ (6.1 g, 5.3 mmol). The reaction was stirred at 80° C. for 6 hours, then cooled to room temperature. The solution was poured into EtOAc, washed with water, sat. aq. $NaHCO_3$, and brine, then dried $(Na_2SO_4)$, filtered, and concentrated in vacuo to provide the crude product. Purification by silica gel chromatography (0–5% EtOAc/hexane) provided the titled product.

Step D
Preparation of 4-cyano-3-fluorobenzylbromide

To a solution of the product from Step C (22.2 g, 165 mmol) in 220 mL of carbontetrachloride was added N-bromosuccinimide (29.2 g, 164 mmol) and benzoylperoxide (1.1 g). The reaction was heated to reflux for 30 minutes, then cooled to room temperature. The solution was concentrated in vacuo to one-third the original volume, poured into EtOAc, washed with water, sat. aq. $NaHCO_3$, and brine, then dried $(Na_2SO_4)$, filtered, and concentrated in vacuo to provide the crude product. Analysis by 1H NMR indicated only partial conversion, so the crude material was resubjected to the same reaction conditions for 2.5 hours, using 18 g (102 mmol) of N-bromosuccinimide. After workup, the crude material was purified by silica gel chromatography (0–10% EtOAc/hexane) to provide the desired product.

Step E
Preparation of 1-(4cyano-3-fluorobenzyl)-5-(acetoxmethyl)-imidazole Hydrobromide A solution of the product from Step B (36.72 g, 96.14 mmol) and the product from Step D (20.67 g, 96.14 mmol) in 250 mL of EtOAc was stirred at 60° C. for 20 hours, during which a white precipitate formed. The reaction was cooled to room temperature and filtered to provide the solid imidazolium bromide salt. The filtrate was concentrated in vacuo to a volume of 100 mL, reheated at 60° C. for two hours, cooled to room temperature, and filtered again. The filtrate was concentrated in vacuo to a volume 40 mL, reheated at 60° C. for another two hours, cooled to room temperature, and concentrated in vacuo to provide a pale yellow solid. All of the solid material was combined, dissolved in 300 mL of methanol, and warmed to 60° C. After two hours, the solution was reconcentrated in vacuo to provide a white solid which was triturated with hexane to remove soluble materials. Removal of residual solvents in vacuo provided the titled product hydrobromide as a white solid which was used in the next step without further purification.

Step F
Preparation of 1-(4-cyano-3-fluorobenzyl)-5-(hydroxymethyl)imidazole

To a solution of the product from Step E (31.87 g, 89.77 mmol) in 300 mL of 2:1 THF/water at 0° C. was added lithium hydroxide monohydrate (7.53 g, 179 mmol). After two hours, the reaction was concentrated in vacuo to a 100 mL volume, stored at 0° C. for 30 minutes, then filtered and washed with 700 mL of cold water to provide a brown solid. This material was dried in vacuo next to $P_2O_5$ to provide the titled product as a pale brown powder which was sufficiently pure for use in the next step without further purification.

Step G
Preparation of 1-(4-cyano-3-fluorobenzyl)-5-imidazolecarboxaldehyde

To a solution of the alcohol from Step F (2.31 g, 10.0 mmol) in 20 mL of DMSO at 0° C. was added triethylamine (5.6 mL, 40 mmol), then $SO_3$-pyridine complex (3.89 g, 25 mmol). After 30 minutes, the reaction was poured into EtOAc, washed with water and brine, dried $(Na_2SO_4)$, filtered, and concentrated in vacuo to provide the aldehyde as a pale yellow powder which was sufficiently pure for use in the next step without further purification.

Step 6
Preparation of 1-[1-(4'-Cyano-3-fluorobenzyl)imidazol-5-ylmethyl]-4-[1-(3-hydroxyphenyl)-1-cyclohexylcarbonyl]piperazine To a solution of the product from Step 4 (280 mg, 850 μmol) in 1,2-dichloroethane (15 mL) was added 4A powdered molecular sieves (400 mg) and sodium triacetoxyborohydride (300 mg, 1.27 mmol). 1-(4-cyano-3-fluorobenzyl)-5-imidazolecarboxaldehyde (140 mg, 700 μmol) from Step 5 was added and the reaction mixture was stirred at room temperature for 16 hours. The reaction was poured into EtOAc and $H_2O$. The organic layer was extracted with sat. aq. $NaHCO_3$ solution and brine, then dried $(Na_2SO_4)$ and concentrated in vacuo. The crude product was chromatographed (2% MeOH in $CHCl_3$) on silica gel to give the title compound.

FAB MS Calcd for $C_{29}H_{32}FN_5O_2$ 502.6 ($MH^+$), found 502.2. Anal. Calcd for $C_{29}H_{32}FN_5O_2$ (0.60 $CHCl_3$: C, 62.02; H, 5.73; N, 12.22. Found: C, 62.37; H, 5.72; N, 11.86.

Example 8
Preparation of 1-[1-(4'-Cyanobenzyl)imidazol-5-ylmethyl]piperazine-4-carboxylic Acid-(2,6-dimethoxy)benzyl Ester

Step 1
Preparation of 2,6-Dimethoxybenzyloxy-(4-nitropheny)carbonate

A THF:acetonitrile (7:1, 2 mL) solution of 4-nitrophenyl chloroformate (0.61 mmol) was added to a THF:acetonitrile (7:1, 2 mL) solution of 2,6-dimethoxybenzyl alcohol (0.103 g, 0.61 mmol) at 25° C. and then stirred for 0.25 hour. Pyridine (0.61 mmol) was then added dropwise over 1 minute. Stirring was continued for 2 hours at 25° C. and then the reaction was diluted with ethyl acetate and washed with water, a saturated sodium chloride solution, dried with sodium sulfate and then evaporated to give the title compound.

$^1$H-NMR ($CDCl_3$): δ8.3 (d, 2H); 7.4 (d, 2H); 7.3 (t, 1H); 6.6 (d, 2H); 5.5 (s, 2H); 3.9 (d, 6H).

Step 2
Preparation of 1-[1-(4'-Cyanobenzyl)imidazol-5-ylmethyl]piperazine-4-carboxylic Acid-(2,6-dimethoxy)benzyl Ester To a DMF solution (2 ml) of 1-(4'-cyanobenzyl)imidazol-5-ylmethyl piperazine (0.067 g, 0.24 mmol) (prepared as described in Example 2, Step 2) and diisopropylethyl amine (0.48 mmol) was added the product from Step 1 (0.084 g, 0.25 mmol) with stirring for 12 hours at 25° C. The title compound was isolated after purification on a preparative hplc via lyophilization.

FAB-MS: calc: 475.5, found: 476.3. $^1$H-NMR ($CD_3OD$): δ8.2 (s, 1H); 7.8 (d, 2H); 7.3 (m, 3H); 7.1 (s, 1H); 6.6 (d, 2H); 5.5 (s, 2H); 5.1 (s, 2H); 3.8 (s, 6H); 3.4 (s, 2H); 3.2 (m, 4H); 2.3 (m, 4H).

Example 9
Preparation of 1-[1-(4'-Cyanobenzyl)imidazol-5-ylmethyl]piperazine-4-(DL-2-hydroxy-2-(o-methoxyphenyl))acetamide

Step 1
Preparation of 2-(DL-O-tert-butyl diphenylsilyl)-2-(2-methoxyphenyl)acetic Acid The title product was obtained by treating DL-2-methoxymandelic acid (0.20 g, 1.1 mmol) with tert-butyldiphenyl silyl chloride (2.42 mmol) and imidazole (11 mmol) followed by selective hydrolysis as outlined in J. Chem. Soc., Perkin Trans I, 1985, 2361. For example, the silyl ester was selectively hydrolyzed by treatment with 10% aqueous $K_2CO_3$ followed by acidification (pH 3) with 1M $KHSO_4$. $^1$H-NMR (CDCl$_3$): δ6.8–7.7 (m, 14H); 5.4 (s, 1H); 3.65 (s, 3H); 1.05 (s, 9H).

Step 2
Preparation of 1-[1-(4'-Cyanobenzyl)imidazol-5-ylmethyl] piperazine-4-(DL-2-hydroxy-2-(o-methoxyphenyl)) acetamide A DMF solution of the product from Step 1 (0.346 g, 0.826 mmol), 1-(4'-cyanobenzyl)imidazol-5-ylmethyl piperazine (0.116 g, 0.413 mmol) (prepared as described in Example 2, Step 2), HOBt (0.132 g, 0.87 mmol), EDC (0.173 g, 0.91 mmol) and NMM (1.24 mmol) was stirred for 18 hours at 25° C. The pure deprotected and protected products were obtained directly after preparative hplc separation and lyophilization. FAB-MS: calc: 445.5, found: 446.2. $^1$H-NMR (CD$_3$OD): δ8.2 (s, 1H); 7.7 (d, 2H); 7.3–7.4 (m, 4H); 6.95–7.1 (m, 3H); 5.7 (s, 1H); 5.5 (s, 2H); 3.85 (s, 3H); 3.5 (m, 1H); 3.0–3.3 (m, 5H); 2.35 (m, 1H); 2.15 (m, 2H); 1.75 (m, 1H).

Example 10
Preparation of 1-[1-(4'-cyanobenzyl)imidazol-5-ylmethyl]-4-[1-(2,6-dimethylbenzyloxycarbonyl]piperazine Bis Trifloroacetate Salt A solution of 250 mg (1.84 mmol) of 2,5-dimethylbenzyl alcohol and 409 mg (2.03 mmol) of p-nitrophenylchloroformate in 5 ml of 7:1 THF/acetonitrile under an argon atmosphere was treated with 164 ml (2.03 mmol) of pyridine, and the resulting suspension was stirred vigorously at room temp. for 18 h. The reaction was concentrated in vacuo to give a clear oil. The oil was dissolved in a minimum of chloroform and was chromatographed over silica gel with 9:1 hexanes/ethyl acetate as eluant. Product fractions were combined and concentrated in vacuo to give the carbonate intermediate as an off-white solid.

400 Mhz H$^1$ NMR(CDCl$_3$): δ2.44 (d, 6H), 5.44 (s, 2H), 7.09 (d, 2H), 7.20 (t, 1H), 7.40 (d, 2H), 8.29 (d, 2H).

A solution of 219 mg (0.71 mmol) of the above prepared carbonate intermediate, 200 mg (0.71 mmol) of 1-(4'-Cyanobenzyl)imidazol-5-ylmethyl piperazine (prepared as described in Example 2, Step 2) and 247 ml (1.42 mmol) of DIEA in 2 ml of methylene chloride was stirred at room temp. for 18 h. The reaction was concentrated in vacuo to a yellow oil. The oil was purified by reversed phase preparatory LC, and the pure fractions combined and concentrated to remove volatiles. Lyophilization of the aqueous residue provided the bis trifluoroacetic acid salt of the desired product as an amorphous fluffy white powder. FAB MS: M+=444.2. 400 Mhz H$^1$ NMR(CDCl$_3$): δ2.39 (s, 6H), 2.65 (br s, 4H), 3.58 (br s, 4H), 3.67 (s, 2H), 5.22 (s, 2H), 5.57 (s, 2H), 7.04 (d, 2H), 7.18 (t, 1H), 7.26 (d, 2H), 7.54 (s, 1H), 7.72 (d, 2H), 8.80 (s, 1H).

Example 11
Preparation of 1-[1-(4'-Cyanobenzyl)imidazol-5-ylmethyl]-4-[1-(2-methoxyphenyl)-1-cyclopentylcarbonyl]piperazine Bis Hydrochloride

Step 1
Preparation of Methyl 1-(2-methoxyphenyl)-1-cyclopentylcarboxylate

Using the appropriate starting materials, the method described in Example 5, Step 1 was employed to prepare the title compound.

EI MS Calcd for $C_{14}H_{18}O_3$ 234.2 (M$^+$), found 234.1; (M$^+$—CO$_2$CH$_3$) 175.1.

Step 2
Preparation of 1-(2-Methoxyphenyl)-1-cyclopentanecarboxylic Acid

The ester from Step 1 was hydrolyzed as in Example 5, Step 2, except that the reaction was stirred at 65° C. for 5 days and then worked up as before to give the title compound, mp 116–124° C.

FAB MS Calcd for $C_{13}H_{16}O_3$ 221.2 (MH$^+$), found 221.1; (M$^+$—CO$_2$H) 175.1.

Step 3
Preparation of 1-[1-(4'-Cyanobenzyl)imidazol-5-ylmethyl]-4-[1-(2-methoxyphenyl)-1-cyclopentylcarbonyl]piperazine Bis Hydrochloride The title compound was prepared from the product from Step 2 using the procedure described in Example 3.

FAB HRMS exact mass Calcd for $C_{29}H_{33}N_5O_2$ 484.2707 (MH$^+$), found 484.2682.

Example 12
Preparation of (±) 1-[1-(4'-Cyanobenzyl)imidazol-5-ylmethyl]-4-[1-(bicyclo[3.1.0]hex-3-yl)-1-(3-methoxyphenyl)-carbonyl]piperazine

Step 1
Preparation of Cis Cyclopropanebismethanol

A solution of lithium aluminum hydride (1M in THF; 48 mL, 48 mmol) was added slowly to a solution of 3-oxabicyclo[3.1.0]hexane-2,4-dione (1.12 g, 10 mmol) in dry THF (15 mL) under Ar at 10° C. The reaction mixture was stirred vigorously at 60° C. for 3 hours. The reaction mixture was then cooled in ice and then quenched by sequential addition of H$_2$O (2 mL)—20% NaOH (2 mL)—H$_2$O (6 mL). Et$_2$O (100 mL) was added and the solution was dried (Na$_2$SO$_4$). The solution was filtered and evaporated in vacuo to give the title compound as a colorless oil.

Step 2
Preparation of Cis 1.2(bisbromomethyl)cyclopropane

Phosphorous tribromide (530 μL, 5.62 mmol) was added dropwise to a solution of the product from Step 1 (810 mg, 7.9 mmol) in Et$_2$O (4 mL) at 10° C. After the addition, the cooling bath was removed and the reaction mixture was stirred at room temperature for 3 hours. The mixture was poured into ice-water and the product extracted into Et$_2$O. The organic layer was washed with brine and dried (Na$_2$SO$_4$). The solution was filtered and evaporated in vacuo to give the title compound as a nearly colorless oil.

EI MS Calcd for $C_5H_8Br_2$ 227.9 (M$^+$), found 227.9; (M$^+$−2HBr) 67.1.

Step 3
Preparation of Methyl(±)3-phenylbicyclo[3.1.0]hexane-3-carboxylate

The title compound was prepared using the procedure in Example 5, Step 1 replacing 1,4-dibromobutane with the product from Step 2 above.

EI MS Calcd for $C_{15}H_{18}O_3$ 246.3 (M$^+$), found 246.2.

Step 4
Preparation of (±) 3-Phenylbicyclo[3.1.0]hexane-3-carboxylic Acid

The ester from Step 3 was hydrolyzed as in Example 5, Step 2 to give the title compound as a 1:1.3 mixture of isomers, mp 78–125° C. 1D-NOE indicated the major isomer has the cyclopropyl moiety directed away from the aromatic ring.

EI MS Calcd for $C_{14}H_{16}O_3$ 232.2 ($M^+$), found 232.2; ($M^+$—$CO_2H$) 187.2.

Step 5
Preparation of (±) 1-[1-(4'-Cyanobenzyl)imidazol-5-ylmethyl]-4-[1-(bicyclo[3.1.0]hex-3-yl)-1-(3-methoxyphenyl)carbonyl]piperazine Using the appropriate starting materials, the method in Example 3 was employed to prepare the title compound, except that conversion to the salt was omitted.

FAB HRMS exact mass Calcd for $C_{30}H_{33}N_5O_2$ 496.2707 ($MH^+$), found 496.2721. Anal. Calcd for $C_{30}H_{33}N_5O_2 \cdot 0.25$ $CHCl_3$; C, 69.14; H, 6.83; N, 13.33. Found: C, 69.01; H, 6.57; N, 13.27.

Example 13
Preparation of (R/S) 2-[4-((Phenyl)methyloxycarbonyl-1-piperazine)]-2-[1-(4'-cyanobenzyl)-2-methyl-5-imidazol] acetonitrile Step 1
Preparation of 1-(4-Cyanobenzyl)-2-methylimidazole-5-carboxaldehyde Step A
Preparation of 4-Bromo-2-methylimidazole-5-carboxaldehyde 4-Bromo-5-hydroxymethyl-2-methylimidazole was prepared according to the procedure described by S. P. Watson, Synthetic Communications, 22, 2971–2977 (1992). A solution of 4-bromo-5-hydroxymethyl-2-methylimidazole (4.18 g, 21.9 mmol) was refluxed with manganese dioxide (16.1 g) in 1:1 methylene chloride:dioxane (200 mL) for 16 h. The cooled reaction was filtered through celite and concentrated to yield the title compound as a pale yellow solid.

$^1$H NMR ($CDCl_3$, 300 MHz) δ9.57 (1H, s), 2.52 (3H, s).

Step B
4-Bromo-1-(4-cyanobenzyl)-2-methylimidazole-5-carboxaldehyde

4-Cyanobenzylbromide (1.05 g, 5.39 mmol) was added to a solution of 4-bromo-2-methylimidazole-5-carboxaldehyde (1.02 g, 5.39 mmol) (Step A) in dimethylacetamide (15 mL). The solution was cooled to −10° C. and powdered potassium carbonate (0.745 g, 5.39 mmol) added. The reaction was stirred at −10° C. for 2 h, and a further 4 h at 20° C. The reaction was diluted with water and extracted with ethyl acetate. The organic phase was washed with water, saturated brine, and dried over magnesium sulfate. Solvent evaporation yielded a white solid.

$^1$H NMR ($CDCl_3$, 400 MHz) δ9.68 (1H, s), 7.64 (2H, d, J=7 Hz), 7.15 (2H, d, J=7 Hz), 5.59 (2H, s), 2.40 (3H, s).

Step C
1-(4-Cyanobenzyl)-2-methylimidazole-5-carboxaldehyde

A solution of 4-bromo-1-(4-cyanobenzyl)-2-methylimidazole-5-carboxaldehyde (1.33 g, 4.37 mmol) (Step B) and imidazole (0.600 g, 8.74 mmol) in 1:1 ethyl acetate-alcohol (150 mL) was stirred with 10% palladium on carbon (0.020 g) under 1 atm hydrogen. After 2 h, the reaction was filtered through celite and concentrated to give the title compound as a white solid.

$^1$H NMR (DMSO-$d_6$, 400 MHz): δ9.62 (1H, s), 7.90 (1H, s), 7.81 (2H, d, J=8 Hz), 7.20 (2H, d, J=8 Hz), 5.64 (2H, s), 2.33 (3H, s).

Step 2
Preparation of (R/S) 2-[4-((Phenyl)methyloxycarbonyl-1-piperazine)]-2-[1-(4'-cyanobenzyl)-2-methyl-5-imidazol] acetonitrile To a round bottomed flask were added 1-(4-Cyanobenzyl)-2-methylimidazole-5-carboxaldehyde (180.0 mg, 0.8 mmol) (prepared as described in Step 1), benzyl 1-piperazinecarboxylate (180.0 mg, 0.8 mmol), titanium(IV) isopropoxide (350 ul, 1.2 mmol), and ethanol (100 ul). The reaction was stirred at RT for 1.0 hr and sodiumcyanoborohydride (55.3 mg, 0.9 mmol) added along with ethanol (100 ul). The reaction stirred at RT for 18 hr. The reaction was diluted with water/methanol/ethylacetate (0.5 ml/1.0 ml/1.0 ml) and filtered through filterpaper. The filtrate was concentrated and redisolved into methanol and purified on a preparative HPLC column yielding the diflouroacetic acid salt of the title compound.

400 Mhz $H^1$ NMR ($CD_3OD$): δ2.46 (br s, 4H), 2.61 (s, 2H), 3.13 (br s, 2H), 3.27 (br s, 2H), 5.10 (s, 2H), 5.30 (s, 1H), 5.60 (q, 2H), 7.33 (m, 7H), 7.79 (d, 3H). High res. FAB MS: Theoretical Mass 455.2174, Measured Mass 455.2189 ($C_{26}H_{26}N_6O_2+H^+$)

Example 14
Preparation of 1-[1-(4'-methylbenzyl)imidazol-5-ylmethyl]-4-[1-(2,6-dimethylbenzyloxycarbonyl)piperazine Step 1
Preparation of 1-(4-methylbenzyl)-5-[(1H-piperazin-4-yl] methylimidazole A solution of 1.51 g (3.35 mmol) of 1-(4-cyanobenzyl)-5-[1-(carbobenzyloxy)piperazin-4-yl] methylimidazole in 25 ml of abs. ethanol was hydrogenated at atmospheric pressure over 1.0 g of 10% Pd on C catalyst. After 24 h, an additional 0.5 g of catalyst was added, and the hydrogenation continued. After another 24 h, a second 0.5 g portion of catalyst was added, and the hydrogenation continued for an additional 48 h. The reaction was filtered, and concentrated in vacuo to give the title compound.

Step 2
Preparation of 1-[1-(4'-methylbenzyl)imidazol-5-ylmethyl]-4-[1-(2,6-dimethylbenzyloxycarbonyl)piperazine In a manner identical to that described above in Example 10, from 250.00 mg of (2,6-dimethylbenzyl)-(4-nitrophenyl)-carbonate (prepared as in Example 10 from p-nitrophenylchloroformate and 2,6-dimethylbenzyl alcohol) and 273 mg (0.89 mmol) of 1-(4-methylbenzyl)-5-[(1H-piperazin-4-yl] methylimidazole was obtained the bis trifluoroacetic acid salt of the desired product as an amorphous fluffy white powder.

High Res. FAB MS: M+theo.=433.2625, obs.=433.2616. 400 Mhz $H^1$ NMR($CDCl_3$): δ2.37 (s, 3H), 2.38 (s, 6H), 2.60 (br s, 4H), 3.58 (br s, 4H), 5.23 (s, 2H), 5.39 (s, 2H), 7.02–7.10 (complex, 5H), 7.16 (d, 1H), 7.22 (d, 2H), 7.26 (d, 1H), 7.47 (s, 1H), 8.53 (s, 1H).

Example 15
Preparation of 1-[1-(4'-Cyanobenzyl)imidazol-5-ylmethyl] piperazine-4-carboxylic Acid-(4-nitro)phenyl Ester To 1-(4'-Cyanobenzyl)imidazol-5-ylmethyl piperazine (0.355 mmol) (prepared as described in Example 2, Step 2) in methanol was added 4-nitrophenyl chloroformate (0.359 mmol) dissolved in THF:acetonitrile (7:1, 0.5 mL) and pyridine (0.718 mmol). The solution was stirred for 0.5 hour at 25° C. and the title product was isolated via preparative hplc followed by lyophilization.

FAB-MS: calc: 446.5, found: 447.2. $^1$H-NMR ($CD_3OD$): δ8.3 (d, 2H); 7.9 (s, 1H); 7.8 (d, 2H); 7.35 (m, 4H); 6.95 (s, 1H); 5.5 (s, 2H); 3.5 (m, 2H); 3.4 (m, 4H); 2.4 (m, 4H).

Example 16
Preparation of 1-[1-(4-Cyanobenzyl)imidazol-5-ylmethyl]-4-[3-(4-fluorophenyl)-3-(tricyclo[3.3.1.1$^{3,7}$]dec-2-yl)-propionyl]piperazine Using the appropriate starting materials, the method in Example 3 was employed to prepare the title compound, except that conversion to salt was omitted.

FAB HRMS exact mass Calcd for $C_{34}H_{38}FN_5O$ 552.3142 (MH$^+$), found 552.3133.

Anal. Calcd for $C_{34}H_{38}FN_5O \cdot 0.50$ CHCl$_3$: C, 67.77; H, 6.35; N, 11.46. Found: C, 67.49; H, 6.38; N, 11.69.

Example 17
Preparation of 2-(1-(4'-cyanobenzyl)imidazol-5-yl)-2-[4-(phenylmethyloxycarbonyl)piperazin-1-yl]acetamide

Step 1
Preparation of (R/S) 2-[4-((Phenyl)methyloxycarbonyl-1-piperazinyl)]-2-[1-(4-bromobenzyl)-2-methyl-5-imidazol]acetonitrile To a round bottom flask were added 1-(4-bromobenzyl)-2-methyl-5-formylimidazole (265.1.0 mg, 1.0 mmol), benzyl 1-piperazinecarboxylate (220.0 mg, 1.0 mmol), methanol (1.5 ml), potassium cyanide (65.0 mg, 1.0 mmol), and acetic acid (100 ul, 1.7 mmol). The reaction was allowed to stir at RT for one hour and then sodium bicarbonate was added (84.0 mg, 1.0 mmol). The reaction was then heated in a sealed tube at 80° C. for two hours, cooled and allowed to stand at RT over night. The reaction mixture was treated with trifluoroacetic acid (0.5 ml) and the mixture diluted with methanol (4.0 ml). The solution was then purified on a prep HPLC column. The title compound was isolated after lyophilization.

400 Mhz H$^1$ NMR (CD$_3$OD): δ2.60 (br s, 4H), 3.30 (br s, 2H), 3.42 (br s, 2H), 5.12 (s, 2H), 5.22 (s, 1H), 5.49 (q, 2H), 7.20 (s, 2H), 7.33 (m, 5H), 7.60 (d, 2H), 7.75 (s, 1H), 8.90 (s, 1H). High res. ES MS: Theoretical Mass 494.1186, Measured Mass 494.1193 ($C_{24}H_{24}BrN_5O_2+H^+$).

Step 2
Preparation of (R/S) 2-(1-(4-bromobenzyl)imidazol-5-yl)-2-(4-(benzylcarboxyl)piperazine-1-yl Acetamide To a round bottom flask were added (R/S) 2-[4-((Phenyl)methyloxycarbonyl-1-piperazinyl)]-2-[1-(4-bromobenzyl)-2-methyl-5-imidazol]acetonitrile (250.0 mg, 0.35 mmol) (prepared as described in Step 1), dimethyl sulfoxide (0.5 ml), and potassium carbonate (194.0 mg, 1.40 mmol). The reaction was cooled to 0° C. (ice/acetone) and hydrogen peroxide was added drop wise (2×0.5 ml of 30%). The reaction was then treated with saturated sodium bisulfite solution until there were no peroxides present (I$_2$/starch paper). The reaction was diluted with methylene chloride/water and the pH adjusted with concentrated ammonium hydroxide solution (Ph>10.0). The organic layer was separated and the aqueous phase reextracted with additional methylene chloride (3×10.0 ml). The combined extracts were dried (MgSO$_4$) and the solvents removed under high vacuum. The resulting gum was dissolved in methanol (4.5 ml) and purified on a prep HPLC column. Pure fractions were combined and lyophilized to give the title compound as a white solid.

400 Mhz H$^1$ NMR (CD$_3$OD): δ2.50 (br s, 4H), 3.93 (br s, 4H), 4.36 (s, 1H), 5.10 (s, 2H), 5.61 (q, 2H), 7.23 (d, 2H), 7.33 (m, 5H), 7.60 (s, 1H), 7.62 (d, 2H), 8.98 (s, 1H). High res. ES MS: Theoretical Mass 512.1292, Measured Mass 512.1296 ($C_{24}H_{26}BrN_5O_3+H^+$).

Step 3
Preparation of 2-(1-(4'-cyanobenzyl)imidazol-5-yl)-2-[4-(phenylmethyloxy carbonyl)piperazin-1-yl]acetamide 1-(1-(4-bromobenzyl)imidazol-5-yl carboxyamidomethyl)-4-(benzylcarboxyl)piperazine from Step 2 (100.0 mg, 0.14 mmol) was dissolved into water (5.0 ml) and the solution was basified with conc. ammonium hydroxide. The mixture was then extracted with methylene chloride. The methylene chloride was dried (MgSO$_4$), and the solvent removed under high vacuum giving a gum. The gum was dissolved in degassed dimethylforamide (2.0 ml) and added to a sealed pressure tube where additional argon was purged through the solution. Tetrakis (triphenylphosphine)palladium(0) (15.0 mg, 0.1 mmol) along with zinc cyanide (16.5 mg, 0.16 mmol) were added to the reaction tube and the reaction heated over night at 80° C. HPLC indicated the reaction to be incomplete. Copper iodide(I) was then added (11.5 mg, 0.06 mmol) and the reaction heated an additional 18 hours. HPLC indicated a new product had formed. The mixture was filtered and purified on a prep HPLC column. Pure fractions were combined and lyophilized to give the title compound as a white solid.

400 Mhz H$^1$ NMR (CD$_3$OD): δ2.55 (br s, 4H), 3.38 (br s, 4H), 4.41 (s, 1H), 5.10 (s, 2H), 5.77 (q, 2H), 7.30–7.40 (m, 5H), 7.47 (m, 2H), 7.70 (s, 1H), 7.81 (d, 2H), 9.09 (s, 1H). High res. ES MS: Theoretical Mass 459.2139, Measured Mass 459.2135 ($C_{25}H_{26}N_6O_3+H^+$).

Example 18
Preparation of 1-[1-(4'-cyanobenzyl)imidazol-5-ylmethyl]-4-[1-(2-methoxy-5-chlorobenzyloxycarbonyl]piperazine In a manner identical to that described above in Example 10, from 220 mg (0.64 mmol) of (2-methoxy-5-chlorobenzyl)-(4-nitrophenyl)carbonate (prepared as described above in Example 10 from p-nitrophenylchloroformate and 2-methoxy-5-chlorobenzyl alcohol) and 180 mg (0.64 mmol) of 1-(4'-Cyanobenzyl)imidazol-5-ylmethyl piperazine (prepared as described in Example 2, Step 2) was obtained the bis trifluoroacetic acid salt of the title compound as an amorphous fluffy white powder.

Fab MS: M+=480.18. 400 Mhz H$^1$ NMR(CDCl$_3$): δ2.62 (br s, 4H), 3.59 (br s, 2H+4H), 3.92 (s, 3H), 5.16 (s, 2H), 5.59 (s, 2H), 6.81 (d, 1H), 7.18–7.36 (complex, 2H+2H), 7.52 (s, 1H), 7.76 (d, 2H), 8.84 (s, 1H).

Example 19
Preparation of 1-[1-(4'-cyanobenzyl)imidazol-5-ylmethyl]-4-[1-(pentafluororobenzyloxycarbonyl]piperazine In a manner identical to that described above in Example 10, from 200 mg (0.55 mmol) of (pentafluorobenzyl)-(4-nitrophenyl)carbonate (prepared as described above in Example 10 from p-nitrophenylchloroformate and pentafluorobenzyl alcohol) and 154 mg (0.55 mmol) of 1-(4'-Cyanobenzyl)imidazol-5-ylmethyl piperazine (prepared as described above in Example 2, Step 2) was obtained the bis trifluoroacetic acid salt of the title compound as an amorphous fluffy white powder.

Fab MS: M+=506. 400 Mhz H$^1$ NMR(CDCl$_3$): δ2.38 (br s, 4H), 3.40 (s, 2H), 3.41 (br s, 4H), 5.22 (s, 2H), 5.56 (s, 2H), 7.28 (d, 2H), 7.35 (s, 1H), 7.74 (d, 2H), 8.79 (s, 1H).

Example 20
Preparation of 1-[1-(4'-cyanobenzyl)imidazol-5-ylmethyl]-4-[1-(2-ethoxybenzyloxycarbonyl]piperazine In a manner identical to that described above in Example 10, from 160 mg (0.53 mmol) of (2-ethoxybenzyl)-(4-nitrophenyl)carbonate (prepared as described above in Example 10 from p-nitrophenylchloroformate and 2-ethoxybenzyl alcohol) and 150 mg (0.53 mmol) of 1-(4'-

Cyanobenzyl)imidazol-5-ylmethyl piperazine (prepared as described above in Example 2, Step 2) was obtained the bis trifluoroacetic acid salt of the title compound as an amorphous fluffy white powder.

High Res. FAB MS: M+theo.=460.2343, obs.=460.2364. 400 Mhz H[1] NMR(DMSO-d$_6$): δ1.36 (t, 3H), 2.39 (br s, 4H), 3.21 (br s, 2H+4H), 3.56 (br s, 2H), 4.04 (q, 2H), 5.02 (s, 2H), 5.60 (s, 2H), 6.93 (t, 1H), 7.00 (d, 1H), 7.26 (t, 1H), 7.29 (d, 1H), 7.44 (d, 2H), 7.71 (s, 1H), 7.89 (d,2H), 9.18 (s, 1H).

Example 21

Preparation of 1-[1-(4'-cyanobenzyl)imidazol-5-ylmethyl]-4-{1-[(2-methoxypyridin-3-yl)methyloxycarbonyl]}piperazine In a manner identical to that described above in Example 10, from 205 mg (0.71 mmol) of (2-methoxypyridin-3-yl methyl)-(4-nitrophenyl)carbonate (prepared as described above in Example 10 from p-nitrophenylchloroformate and 2-methoxy-3-pyridinemethanol) and 200 mg (0.71 mmol) of 1-(4'-Cyanobenzyl)imidazol-5-ylmethyl piperazine (prepared as described in Example 2, Step 2) was obtained the tris trifluoroacetic acid salt of the title compound as an amorphous fluffy white powder.

400 Mhz H[1] NMR(DMSO-d$_6$): δ2.51 (br s, 4H), 3.31 (br s, 4H), 3.69 (br s, 2H), 3.89 (s, 3H), 5.02 (s, 2H), 5.62 (s, 2H), 7.02 (m, 1H), 7.46 (d, 2H), 7.66 (d, 1H), 7.76 (s, 1H), 7.89 (d, 2H), 8.16 (m, 1H), 9.22 (s, 1H).

Example 22

Preparation of 1-[1-(4'-cyanobenzyl)imidazol-5-ylmethyl]-4-[1-(2-trifluoromethoxybenzyloxycarbonyl]piperazine In a manner identical to that described above in Example 10, from 172 mg (0.51 mmol) of (2-trifluoromethoxybenzyl)-(4-nitrophenyl)carbonate (prepared as described above in Example 10 from p-nitrophenylchloroformate and 2-trifluoromethoxybenzyl alcohol) and 144 mg (0.51 mmol) of 1-(4'-Cyanobenzyl) imidazol-5-ylmethyl piperazine (prepared as described above in Example 2, Step 2) was obtained the bis trifluoroacetic acid salt of the title compound as an amorphous fluffy white powder.

400 Mhz H[1] NMR(DMSO-d$_6$): δ2.33 (br s, 4H), 3.18 (br s, 4H), 3.52 (br s, 2H), 5.14 (s, 2H), 5.60 (s, 2H), 7.37–7.55 (complex, 6H), 7.69 (s, 1H), 7.89 (d, 1H), 9.19 (br s, 1H).

Example 23

Preparation of 1-[1-(4'-cyanobenzyl)imidazol-5-ylmethyl]-4-[1-(2,3-methylenedioxybenzyloxycarbonyl]piperazine In a manner identical to that described above in Example 10, from 340 mg (1.07 mmol) of (2,3-methylenedioxybenzyl)-(4-nitrophenyl)carbonate (prepared as described above in Example 10 from p-nitrophenylchloroformate and 2,3-methylenedioxybenzyl alcohol) and 300 mg (1.07 mmol) of 1-(4-Cyanobenzyl) imidazol-5-ylmethyl piperazine (prepared as described above in Example 2, Step 2) was obtained the bis trifluoroacetic acid salt of the title compound as an amorphous fluffy white powder.

High Res FAB MS: M+theo.=460.1979, obs.=460.1975. 400 Mhz H[1] NMR(DMSO-d$_6$): δ2.42 (br s, 4H), 3.28 (br s, 4H), 3.66 (br s, 2H), 5.05 (s, 2H), 5.61 (s, 2H), 6.04 (s, 2H), 6.85 (m, 2H), 6.91 (m, 1H), 7.48 (d, 2H), 7.76 (s, 1H), 7.92 (d, 2H), 9.21 (s, 1H).

Example 24

Preparation of 1-[1-(4'-Cyanobenzyl)imidazol-5-ylmethyl]piperazine-4-carboxylic Acid Benzyl Ester To an acetonitrile solution of 1-(4'-cyanobenzyl)-5-chloromethylimidazole (7.45 mmol), prepared as described in Example 1, Step 4, and diisopropylethyl amine (22.4 mmol) was added 1-benzyl 1-piperazine carboxylate (10.4 mmol). This solution was stirred for 4.0 hours at 80° C. The title compound was isolated after silica column purification.

$^1$H-NMR (CDCl$_3$): δ7.65 (d, 2H); 7.55 (s, 1H); 7.38 (m, 5H); 7.15 (d, 2H); 7.0 (s, 1H); 5.3 (s, 2H); 5.1 (s, 1H); 3.4 (m, 4H); 3.3 (s, 2H); 2.3 (m, 4H).

Example 25

Preparation of 1-[1-(4'-Cyanobenzyl)imidazol-5-ylmethyl]-piperazine-3-carboxylic acid-4-carboxylic Acid Benzyl Ester Step 1

Preparation of 1-[1-(4'-Cyanobenzyl)imidazol-5-ylmethyl]-3-methyl carboxy -piperazine-4-carboxylic Acid Benzyl Ester To an acetonitrile solution of 1-(4'-cyanobenzyl)-5-chloromethylimidazole (0.886 mmol) (prepared as described in Example 1, Step 4) and diisopropylethyl amine (22.4 mmol) was added 1-benzylcarboxylate-2-methylcarboxylate-1-piperazine (1.24 mmol). This solution was stirred for 4.0 hour at 80° C. The product was isolated after preparative hplc purification.

FAB-MS: calc: 473.5, found: 474.2. $^1$H-NMR (CD$_3$OD): δ9.05 (s, 1H); 7.8 (d, 2H); 7.6 (s, 1H); 7.45 (d, 2H); 7.35 (m, 5H); 5.6 (s, 2H); 5.2 (s, 2H); 3.9 (t, 1H); 3.7 (s, 4H); 3.6 (m, 1H); 3.5 (q, 1H); 3.1 (m, 2H); 2.7 (m, 1H): 2.35 (dd, 1H); 2.1 (t, 1H).

Step 2

Preparation of 1-[1-(4'-Cyanobenzyl)imidazol-5-ylmethyl] piperazine-3-carboxylic acid-4-carboxylic Acid Benzyl Ester The product from Step 1 (0.296 mmol) was dissolved in THF and then aqueous lithium hydroxide was added (1.18 mmol). After stirring for 18 hours the product was purified via preparative hplc and the title compound was isolated via lyophilization.

FAB-MS: calc: 459.5, found: 460.2. $^1$H-NMR (CD$_3$OD): δ9.0 (s, 1H); 7.8 (d, 2H); 7.6 (s, 1H); 7.5 (d, 2H); 7.35 (m, 5H); 5.6 (s, 2H); 5.2 (m, 2H); 4.75 (s, 1H); 3.9 (t, 1H); 3.5 (q, 2H); 3.2 (m, 2H); 2.7 (m, 2H); 2.3 (dd, 1H); 2.1 (m, 1H).

Example 26

Preparation of 1-[1-(4'-Cyanobenzyl)imidazol-5-ylmethyl] piperazine-4-(N-3-isopropenyl-1,1-dimethylbenzyl) carboxamide To 1-(4'-Cyanobenzyl)imidazol-5-ylmethyl piperazine (prepared as described above in Example 2, Step 2) (0.292 mmol) in ethyl acetate was added 3-isopropenyl-1,1-dimethylbenzyl isocyanate (0.277 mmol) and diisopropylethyl amine (0.292 mmol). After stirring at 25° C. for 18 hours, the reaction was purified via preparative hplc and the title compound was isolated via lyophilization.

FAB-MS: calc: 482.5, found: 483.2. $^1$H-NMR (CD$_3$OD): δ9.05 (s, 1H); 8.0 (s, 1H); 7.8 (d, 2H); 7.5 (d, 2H); 7.45 (s, 1H); 7.25 (m, 3H); 5.8 (s, 2H); 5.3 (s, 1H); 5.05 (s, 1H); 4.3 (m, 2H); 3.0–3.6 (m, 8H); 2.1 (s, 3H); 1.6 (s, 6H).

Example 27

Preparation of 1-[(1-(4'-cyanobenzyl)imidazol-5-ylmethyl]-4-phenylmethanesulfonyl-(cis)-2,6-dimethylpiperazine To a round bottomed flask were added 3-chloro-4-hydroxyphenylacetic acid (50.0 mg, 0.3 mmol), a-toluenesulfonyl chloride (51.1 mg, 0.3 mmol), potassium carbonate (260.0 mg, 2.1 mmol), TEBAC (6.2 mg, 0.03 mmol), and benzene (1.0 ml). The reaction was heated at 100° C. for 40 minutes. 1-(1-(4-cyanobenzyl)imidazol-5-ylmethyl)-(cis)-2,6-dimethylpiperazine (112.0 mg, 0.3 mmol) (prepared in the same manner as the 1-(1-(4-Cyanobenzyl)imidazole-5-ylmethyl)-(trans)2,5-dimethylpiperazine in Example 41 below) was then added and the reaction heated an additional 10 minutes. The reaction was allowed to cool to RT over 40 minutes. The reaction was diluted with ethyl acetate (5.0 ml) and water (1.0 ml). Additional ethyl acetate was added and the mixture basified with dilute sodium hydroxide (1 drop). The layers were separated and the ethyl acetate removed under vacuum. The residue was dissolved in 4.5 ml of methanol and purified on a preparative HPLC column to give the diflouroacetic acid salt of the title compound.

400 Mhz $H^1$ NMR ($CD_3OD$): δ0.85 (d, 6H), 2.64 (m, 4H), 3.21 (d, 2H), 3.65 (s, 2H), 4.32 (s, 2H), 5.58 (s, 2H), 7.40 (m,7H), 7.60 (s, 1H), 7.82 (d, 2H), 9.01 (s, 1H). High Res. FAB MS: Theoretical Mass 464.2115, Measured Mass 464.2134 ($C_{25}H_{29}N_5O_2S+H^+$).

Example 28

Preparation of 2-(1-(4'-cyanobenzyl)-5-imidazolyl))-2-[(4'-phenylmethyloxycarbonyl) piperazin-1'-yl]acetonitrile Step 1
Preparation of 1-(4-cyanobenzyl)-5-imidazole Carboxaldehyde Step A
Preparation of 1-triphenylmethyl-4-(hydroxymethyl)-imidazole To a solution of 4-(hydroxy-methyl)imidazole hydrochloride (35.0 g, 260 mmol) in 250 mL of dry DMF at room temperature was added triethylamine (90.6 mL, 650 mmol). A white solid precipitated from the solution. Chlorotriphenylmethane (76.1 g, 273 mmol) in 500 mL of DMF was added dropwise. The reaction mixture was stirred for 20 hours, poured over ice, filtered, and washed with ice water. The resulting product was slurried with cold dioxane, filtered, and dried in vacuo to provide the titled product as a white solid which was sufficiently pure for use in the next step.

Step B
Preparation of 1-triphenylmethyl-4-(acetoxymethyl)-imidazole

Alcohol from Step A (260 mmol, prepared above) was suspended in 500 mL of pyridine. Acetic anhydride (74 mL, 780 mmol) was added dropwise, and the reaction was stirred for 48 hours during which it became homogeneous. The solution was poured into 2 L of EtOAc, washed with water (3×1 L), 5% aq. HCl soln. (2×1 L), sat. aq. $NaHCO_3$, and brine, then dried ($Na_2SO_4$), filtered, and concentrated in vacuo to provide the crude product. The acetate was isolated as a white powder which was sufficiently pure for use in the next reaction.

Step C
Preparation of 1-(4-cyanobenzyl)-5-(acetoxymethyl)-imidazole Hydrobromide A solution of the product from Step B (85.8 g, 225 mmol) and a-bromo-p-toluitnitrile (50.1 g, 232 mmol) in 500 mL of EtOAc was stirred at 60° C. for 20 hours, during which a pale yellow precipitate formed. The reaction was cooled to room temperature and filtered to provide the solid imidazolium bromide salt. The filtrate was concentrated in vacuo to a volume of 200 mL, reheated at 60° C. for two hours, cooled to room temperature, and filtered again. The filtrate was concentrated in vacuo to a volume of 100 mL, reheated at 60° C. for another two hours, cooled to room temperature, and concentrated in vacuo to provide a pale yellow solid. All of the solid material was combined, dissolved in 500 mL of methanol, and warmed to 60° C. After two hours, the solution was reconcentrated in vacuo to provide a white solid which was triturated with hexane to remove soluble materials. Removal of residual solvents in vacuo provided the titled product hydrobromide as a white solid which was used in the next step without further purification.

Step D
Preparation of 1-(4-cyanobenzyl)-5-(hydroxymethyl)-imidazole

To a solution of the acetate from Step C (50.4 g, 150 mmol) in 1.5 L of 3:1 THF/water at 0° C. was added lithium hydroxide monohydrate (18.9 g, 450 mmol). After one hour, the reaction was concentrated in vacuo, diluted with EtOAc (3 L), and washed with water, sat. aq. $NaHCO_3$ and brine. The solution was then dried ($Na_2SO_4$), filtered, and concentrated in vacuo to provide the crude product as a pale yellow fluffy solid which was sufficiently pure for use in the next step without further purification.

Step E
Preparation of 1-(4-cyanobenzyl)-5-imidazolecarboxaldehyde

To a solution of the alcohol from Step D (21.5 g, 101 mmol) in 500 mL of DMSO at room temperature was added triethylamine (56 mL, 402 mmol), then $SO_3$-pyridine complex (40.5 g, 254 mmol). After 45 minutes, the reaction was poured into 2.5 L of EtOAc, washed with water (4×1 L) and brine, dried ($Na_2SO_4$), filtered, and concentrated in vacuo to provide the aldehyde as a white powder which was sufficiently pure for use in a subsequent step without further purification.

Step 2
Preparation of 2-(1-(4'-cyanobenzyl)-5-imidazolyl))-2-[(4'-phenylmethyloxycarbonyl)piperazin-1'-yl]acetonitrile 1-(4'-cyanobenzyl)-5-imidazole carboxaldehyde (320 mg; 1.5 mmol) and carbobenzyloxypiperazine (330 mg; 1.5 mmol) were mixed with potassium cyanide in MeOH (2 ml) and glac. acetic acid (0.1 ml). Sodium bicarbonate (130 mg) was added and the mixture was heated at 80° C. for 4 hours. The crude mixture was filtered and the filtrate purified by preparative HPLC. Fractions containing pure product were lyophilized to a gum which was relyophilized from dioxane to give pure title compound.

NMR ($CD_3OD$): δ8.96 (1H), 7.80 (2H, d), 7.80 (1H, s), 7.42 (2H, d), 7.32 (1H, s), 5.61 (2H, dd), 5.23 (1H, s), 5.11 (2H, s), 3.38 and 3.23 (2H, m).

Example 29

Preparation of 1-[1-(4-Cyanobenzyl)imidazol-5-ylmethyl]-4-(2-tert-butyl-3-phenyl)propionyl Piperazine The title compound was prepared using the procedure in Example 3, replacing 1-phenyl-1-cyclopentane carboxylic acid with 2-tert-butyl-3-phenylpropionic acid.

Hi-Res MS: calc: 470.2899; found: 470.2914.

Example 30

Preparation of 1-[1-(4'-Cyanobenzyl)imidazol-5-ylmethyl]-4-[1-(4-methoxyphenyl)-1-cyclohexyl]carbonyl Piperazine The title compound was prepared using the procedure in Example 3, replacing 1-phenyl-1-cyclopentane carboxylic acid with 2-(4'-methyoxyphenyl) cyclohexane carboxylic acid.

Hi-Res MS: calc: 498.2859; found: 498.2863.

Example 31
Preparation of 1-(4-cyanobenzyl)-5-{1-[(2-ethoxypyridin-3-yl)methyloxycarbonyl]piperazin-4-yl}methylimidazole In a manner identical to that described above in Example 10, from 400 mg (1.32 mmol) of (2-ethoxypyridin-3-yl methyl)-(4-nitrophenyl)carbonate (prepared as above in Example 10 from p-nitrophenylchloroformate and 2-ethoxy-3-hydroxymethylypyridine) and 372 mg (1.32 mmol) of 1-(4'-Cyanobenzyl)imidazol-5-ylmethyl piperazine (prepared as described in Example 2, Step 2) was obtained the bis trifluoroacetic acid salt of the title compound as an oil.

High Res FAB MS: M+theo.=461.2301, obs.=461.2289. 400 Mhz $H^1$ NMR(DMSO-$d_6$): $\delta$1.39 (t, 3H), 2.41 (br s, 4H), 3.41 (s, 2H), 3.49 (br s, 4H), 4.41 (q, 2H), 5.14 (s, 2H), 5.60 (s, 2H), 6.90 (t, 1H), 7.34 (d, 2H), 7.36 (s, 1H), 7.57 (d, 1H), 7.73 (d, 2H), 8.12 (m, 1H), 8.91 (s, 1H).

Example 32
Preparation of 1-(4-cyanobenzyl)-5-[1-(2-methanesulfonylbenzyloxycarbonyl)piperazin-4-yl]methylimidazole In a manner identical to that described above in Example 10, from 298 mg (0.85 mmol) of (2-methanesufonylbenzyl)-(4-nitrophenyl)carbonate (prepared as described above in Example 10 from p-nitrophenylchloroformate and 2-methanesulfonylbenzyl alcohol) and 240 mg (0.85 mmol) of 1-(4'-Cyanobenzyl)imidazol-5-ylmethyl piperazine (prepared as described in Example 2, Step 2) was obtained the bis trifluoroacetic acid salt of the title compoound as an amorphous fluffy white powder.

High Res FAB MS: M+theo.=494.1856, obs.=494.1840. 400 Mhz $H^1$ NMR(DMSO-$d_6$): $\delta$2.42 (br s, 4H), 3.29 (br s, 4H), 3.31 (s, 3H), 3.59 (br s, 2H), 5.48 (s, 2H), 5.64 (s, 2H), 7.47 (d, 2H), 7.63 (m, 2H), 7.72 (s, 1H), 7.76 (t, 1H), 7.91 (d, 2H), 7.96 (d, 1H), 9.22 (s, 1H).

Example 33
Preparation of 1-(1(4-cyanobenzyl)imidazol-5-yl)piperazine-4-(N-(2-ethoxybenzyl)carbamide)

Dry methylene chloride (10.0 ml) was added to a round bottom flask along with Proton-Sponge[1,8-bis(dimethylamino)naphthalene, N,N,N',N'-tetramethyl-1,8-naphthalenediamine] (150.3 mg, 0.71 mmol), and 2-ethoxybenzylamine (0.106 ml, 0.71 mmol). The solution was cooled to 5° C. with an ice/water bath and phosgene (0.375 ml, 0.71 mmol, 20% in toluene) was added drop wise. The ice bath was removed and the reaction allowed to warm to RT over thirty-five minutes. The solution was placed into a sepratory funnel and the methylene chloride solution was extracted with cold dilute hydrochloric acid. The methylene chloride was filtered through $MgSO_4$. The filtrate was charged with 1-(1-(4-Cyanobenzyl)imidazole-5-yl-methyl)piprazine (200.0 mg, 0.71 mmol) (prepared as described in Example 2, Step 2) and diisopropylethyl amine (0.310 ml, 1.78 mmol). The reaction was stired at RT for 2.0 hours. The solvents were removed under vacuum and the residue disoloved into methanol (4.0 ml). The methanol solution was then purified by prep HPLC giving the title compound.

400 Mhz $H^1$ NMR ($CD_3OD$): $\delta$1.40 (t, 3H), 2.59 (t, 4H), 3.38 (t, 4H), 3.73 (s, 2H), 4.06 (q, 2H), 4.36 (s, 2H), 5.68 (s, 2H), 6.88 (m, 2H), 7.16 (m, 2H), 7.45 (d, 2H), 7.68 (s, 1H), 7.87 (d, 2H), 9.06 (s, 1H). High res. FAB MS: Theoretical Mass 459.2503, Measured Mass 459.2516 ($C_{26}H_{30}N_6O_2$+$H^+$).

Example 34
Preparation of [1-((1(4-cyanobenzyl)-2-methyl)imidazol-5-yl)-4-(benzyloxycarbonyl)]piperazine To a round bottom flask were added 1-(4-cyanobenzyl)-2-methyl-5-formylimidazole (prepared as described in Example 13, Step 1) (180.0 mg, 0.8 mmol), benzyl 1-piperazinecarboxylate (180.0 mg, 0.8 mmol), titanium(IV) isopropoxide (350 ul, 1.2 mmol), and ethanol (100 ul). The reaction was stirred at RT for 1.0 hr and sodiumcyanoborohydride (55.3 mg, 0.9 mmol) was added along with ethanol (100 ul). The reaction was stirred at RT for 18 hr. The reaction was diluted with water/methanol/ethylacetate (.5 ml/1.0 ml/1.0 ml) and filtered through filterpaper. The filtrate was concentrated and redisolved into methanol and purified on a preparative HPLC column yielding the diflouroacetic acid salt of the title compound.

400 Mhz $H^1$ NMR ($CD_3OD$): 2.37 (br s, 4H), 2.59 (s, 3H), 3.28 (br s, 4H), 3.51 (s, 2H), 5.10 (s, 2H), 5.64 (s, 2H), 7.34 (m, 7H), 7.51 (s, 1H), 7.79 (d, 2H). High res. FAB MS: Theoretical Mass 430.2237, Measured Mass 430.2242 ($C_{25}H_{27}N_5O_2$+$H^+$).

Example 35
Preparation of Ureas From Isocyanates and Chloroformates

To each of two previosly tared screw cap test tubes was added approximately 0.1 mmol of one of the isocyanates or chloroformates. Then 1 equivalent of a stock DMF solution of 1-(4'-Cyanobenzyl)imidazol-5-ylmethyl piperazine (prepared as described in Example 2, Step 2) was added to each tube followed by 0.5 mL of ethyl actate, 2 equivalents of DIEA and 0.3 mL of DCM. Each solution was stirred for 18 hours and then diluted with 1.0 mL each of ethyl acetate and water, vortex stirred and then centrifuged. The aqueous layer was removed and the organic layer was rotary speed evaporated to a pellet. The resulting pellets were dissolved in 2.0 mL of DMSO and submitted for LC and Hi-Res Mass spec analysis. The completness of reaction was estimated by comparing the AUC of each reaction against an independently prepared standard of known concentration that was also prepared in the library run. The following compounds were prepared by this method:

1-(4'-Cyanobenzyl)imidazol-5-ylmethyl piperazine-4-(N-3-methylbenzyl)carboxamide Hi-Res MS: calc: 429.2398; found: 429.2397.

1-(4'-Cyanobenzyl)imidazol-5-ylmethyl piperazine-4-(N-2-chlorobenzyl)carboxamide Hi-Res MS: calc: 449.1848; found: 449.1851.

Example 36
Preparation of 1-(1(4'-cyanobenzyl)imidazol-5-yl)-piperazine-4-(N-(2-methoxybenzyl)carboxamide)

Dry methylene chloride (1.0 ml) was added to a round bottom flask along with "proton-sponge" [1,8-bis(dimethylamino)naphthalene, N,N,N',N'-tetramethyl-1,8-naphthalenediamine] (428.0 mg. 2.0 mmol), and 2-methoxybenzylamine (137 mg, 1.0 mmol). The solution was cooled to 5° C. with an ice/water bath and phosgene (0.57 ml, 1.1 mmol, 20% in toluene) was added drop wise. The ice bath was removed and the reaction was allowed to warm to RT over thirty-five minutes. Cold dilute hydrochloric acid solution (1.0 ml, 1.0 N) was added and the mixture agitated. The aqueous layer was removed and the remaining methylenechloride solution dried ($MgSO_4$). An aliquot (0.05 mmol) of the stock isocyanate solution was then added to a tared test tube containing 1-(1-(4-Cyanobenzyl)imidazole-5-ylmethyl)piperazine (0.05 mmol in DMF) (prepared as described in Example 2, Step 2), ethyl acetate (1.0 ml), and diisopropylamine (0.022 ml, 0.13 mmol). The reaction was allowed to stand for 48 hours. Ethylacetate (1.5 ml) along with water (0.5 ml), and brine (0.5 ml) were added to the tube. The tube was shaken and the aqueous layer carefully removed. The test tube sample was concentrated in a rotary speed evaporator. The weight of the resulting pellet was then used to dilute the sample to standard concentrations for analytical and biological assays. Purity was checked using standard HPLC techniques and High res Mass Spect.

High res. FAB MS Theoretical Mass 437.3023, Measured Mass 445.2345 ($C_{25}H_{28}N_6O_2$+$H^+$).

Example 37
Preparation of 1-(1-(4'-cyanobenzyl)imidazol-5-yl)-piperazine-4-(N-(3-methoxy-6-chlorobenzyl) carboxamide)

The title compound was prepared as in Example 36.
High res. FAB MS: Theoretical Mass 479.1957, Measured Mass 479.1955 ($C_{25}H_{27}ClN_6O$+$H^+$).

Example 38
Preparation of 1-(1-(4'-cyanobenzyl)imidazol-5-yl)-piperazine-4(N-(2-methyl-5-chlorobenzyl)-carboxamide)

The title compound was prepared as in Example 36.
High res. FAB MS: Theoretical Mass 463.2008, Measured Mass 445.2009 ($C_{25}H_{27}ClN_6O$+$H^+$).

Example 39
Preparation of 1-(1-(4'-cyanobenzyl)imidazol-5-yl)-piperazine-4-(N-(3-phenylpropyl) carboxamide)

The title compound was prepared as in Example 36.
High res. FAB MS: Theoretical Mass 443.2554, Measured Mass 443.2570 ($C_{26}H_{30}N_6O$+$H^+$).

Example 40
Preparation of [1-(1(4'-cyanobenzyl)imidazol-5-yl)-piperazine-4-(N-(2,5-dimethylbenzyl)carbamide)

The title compound was prepared as in Example 36.
High res. FAB MS: Theoretical Mass 443.2554, Measured Mass 443.2582 ($C_{26}H_{30}N_6O$+$H^+$).

Example 41
Preparation of 1-(1-(4-Cyanobenzyl)imidazole-5-ylmethyl)-4-benzyloxycarbonyl)-(trans)-2,5-dimethylpiperazine Step 1
Preparation of (trans) 2,5-Dimethyl-4-tertbutyloxycarbonylpiperazine To a round bottom flask were added (trans)-2,5-dimethylpiperazine (2.5 gm, 21.1 mmol) and dichloromethane (75 ml). The solution was cooled to 5° C. with an ice/water bath and di-tert-butyl dicarbonate (2.39 gm, 10.9 mmol) in dichloromethane (10 ml) was added dropwise. After the addition, the reaction was allowed to warm to room temperature and was stir over night. The methylenechloride was washed with water (3×25 ml). The methylenechloride was then extracted with a 10% solution of citric acid (50 ml) and the citric acid layer was washed with additional methylene chloride (50 ml). The citric acid layer was then basified with excess concentrated ammonium hydroxide and the basic mixture extracted with ethylacetate (2×250 ml). The combined extracts were washed with brine (2×75 ml), and dried (MgSO$_4$). The solvent was removal under vacuum to give the title compound. The material was used with out further purification.

Step 2
Preparation of 1-(1-(4-Cyanobenzyl)imidazole-5-ylmethyl)-4-(tert-butyloxycarbonyl)-(trans)2,5-dimethylpiperazine To a round bottom flask were added 1-(4-cyanobenzyl)-5-formylimidazole (250.0 mg, 1.2 mmole) along with titanium(IV)isopropoxide (1.0 ml, 3.65 mmol), (trans) 2,5-Dimethyl-4-tertbutyloxycarbonylpiprizine (253.7 mg, 1.2 mmol) (prepared as described in Step 1), and tetrahydrofuran (0.4 ml). The reaction was heated at 60° C. for 1.25 hour. The reaction was cooled and sodiumcyanoborohydride (95.0 mg, 1.5 mmol) was added along with ethanol (0.5 ml) and the reaction was stirred at RT for 18 hours. The reaction was diluted with methanol/water (3 ml/1 ml) and the mixture filtered through celite. The filtrate was then concentrated to an oil, dissolved into methanol and put through a High Pressure Liquid Chromatography column. The desired fractions were collected, concentrated, and lyophilized to give the ditrifluoroacetic acid salt of the title compound.

400 Mhz $H^1$ NMR (CD$_3$OD): δ0.97 (d, 3H), 1.14 (d, 3H), 1.46 (s, 9H), 2.28 (d, 1H), 2.77 (d of d, 1H), 2.88 (br s, 1H), 3.20 (d of d, 1H), 3.53–3.68 (m, 3H), 4.21 (t, 1H), 5.73 (d, 2H), 7.45 (d, 2H), 7.64 (s, 1H), 7.82 (d of d, 2H), 9.05 (s, 1H). High res. FAB MS: Theoretical Mass 410.2550, Measured Mass 410.2550 ($C_{23}H_{31}N_5O_2$+$H^+$).

Step 3
Preparation of 1-(1-(4-Cyanobenzyl)imidazole-5-ylmethyl)-(trans)2,5-dimethylpiperazine To a round bottom flask were added 1-(1-(4-Cyanobenzyl)imidazole-5-ylmethyl)-4-(tert-butyloxycarbonyl)-(trans)-2,5-dimethylpiprazine (270.0 mg, 0.4 mmol) (prepared as described in Step 2) along with trifluoroacetic acid (neat). After 2.0 hours HPLC showed the Boc group removal to be complete. The solvent was removed to give the trifluoroacetic acid salt of the title compound. The material was used with out further purification.

400 Mhz $H^1$ NMR (CD$_3$OD): δ1.11 (d, 3H), 1.18 (d, 3H), 2.03 (t, 2H), 2.52–2.60 (m, 1H), 2.65 (t, 1H), 2.76–2.80 (d of d, 1H), 2.80–2.90 (m, 1H), 3.23–3.28 (d of d, 2H), 4.12 (d, 1H), 5.67 (q, 2H), 7.42 (d, 2H), 7.67 (s, 1H), 7.82 (d, 2H), 9.10 (s, 1H). High res. FAB MS: Theoretical Mass 310.2026, Measured Mass 410.2040 ($C_{23}H_{31}N_5O_2$+$H^+$).

Step 4
Preparation of 1-(1-(4-Cyanobenzyl)imidazole-5-ylmethyl)-4-benzyloxycarbonyl)-(trans)-2,5-dimethylpiperazine To a round bottom flask were added N-benzyloxycarbonyloxy-5-norbornene-2,3-dicarboximide (75.1 mg, 0.2 mmol) along with 1-(1-(4-Cyanobenzyl)imidazole-5-ylmethyl)-(trans)2,5-dimethylpiprazine (142.0 mg, 0.2 mmol) (prepared as described in Step 3), diisopropylethylamine (0.227 ml, 1.30 mmol), and dimethylforamide (4.0 ml). The reaction was allowed to stir for 48 hr. Solvents were removed under high vac. and the residue dissolved into 4.5 ml of methanol and purified on a preparative HPLC column yielding the title compound as a white solid.

400 Mhz $H^1$ NMR (CD$_3$OD): δ0.93 (d, 3H), 1.14 (d, 3H), 2.25 (d of d, 1H), 2.75 (d of d, 1H), 2.85 (m, 1H), 3.24 (d of d, 1H), 3.55 (q, 2H), 3.72 (d, 1H), 4.26 (m, 1H), 5.12 (q, 2H), 5.71 (q, 2H), 7.32 (m, 5H), 7.43 (d, 2H), 7.61 (s, 1H), 7.80 (d, 2H), 9.03 (s, 1H). High res. ES MS: Theoretical Mass 444.2394, Measured Mass 444.2368($C_{27}H_{37}N_5O_2$+$H^+$).

Example 42
1-[1-(4-cyanobenzyl)-2-methylimidazol-5-ylmethyl]-4-[2-ethoxybenzyloxycarbonyl]piperazine Step 1
1-[1-(4-cyanobenzyl)-2-methylimidazol-5-ylmethyl]-4-piperazine A mixture of 2.50 g(11.05 mmol) of 1-(4-cyanobenzyl)-2-methylimidazole-5-carboxaldehyde (prepared as described in Example 13, Step 1), 2.44 g (11.05 mmol) of 1-(benzyloxycarbonyl)piperazine, and 4.11 ml (13.81 mmol) of titanium isopropoxide in 5 ml anh. THF was stirred at RT for 1 h. The reaction was diluted with 5 ml of anh. EtOH, and the solution treated with 695 mg(11.05 mmol) of sodium cyanoborohydride. The reaction was heated at 65° C. for 1 h, and was stirred at RT for an additional 18 h. The reaction was poured into excess water, and the suspension stirred vigorously for 10 min. The mixture was diluted with ethyl acetate, and was filtered through a Celite pad. The filtrate was separated, and the organic layer dried and concentrated in vacuo to give a brown oil. The oil was purified by column chromatography over silica gel using acetonitrile followed by 5% methanol/chloroform to give 2 g of a yellow oil. The oil was dissolved in 15 ml abs. ethanol, and was hydrogenated at atmospheric pressure over 250 mg of 10% Pd on C catalyst. After approx. 30 h, the reaction was filtered through a celite pad to give the desired product as a pale yellow oil. $H^1$ NMR(CDCl$_3$): 2.29(s,3H), 2.30(br s, 4H), 2.90(br s, 4H), 3.29(s,2H), 5.14 (s,2H), 6.87(s,1H), 7.05(d,2H), 7.62(d,2H).

Step 2
1-[1-(4-cyanobenzyl)-2-methylimidazol-5-ylmethyl]-4-[2-ethoxybenzyloxycarbonyl]pipiperazine In the manner described in Example 10, from 148 mg (0.49 mmol) of 2-(ethoxybenzyl)-(4-nitrophenyl)carbonate (prepared as described in Example 10 from p-nitrophenyl chloroformate and 2-ethoxybenzyl alcohol) and 145 mg(0.49 mmol) of 1-[1-(4-cyanobenzyl)imidazol-5-ylmethyl]-4-piperazine (prepared as described in Example 42, Step 1) was obtained the bis trifluoroacetic acid salt of the title compound as an amorphous fluffy white powder.

High Res. FAB MS: M+theo.=474.2500; obs.=474.2500. 400 MHz $H^1$ NMR(DMSO-d$_6$): 1.34(t,3H), 2.38(br s, 4H), 2.55(s,3H), 3.16(br s, 4H), 3.52(br s, 2H), 4.04(q,2H), 5.03(s,2H), 5.58(s,2H), 6.93(t,1H), 6.97(d,1H), 7.24(m,2H), 7.37(d,2H), 7.64(s,1H), 7.88(d,2H).

Example 43
1-[1-(4-cyanobenzyl)-2-methylimidazol-5-ylmethyl]-4-[2-(trifluoromethoxy)benzyloxycarbonyl]piperazine Using the reaction methods described in Example 10, from 269 mg (0.75 mmol) of 2-(trifluoromethoxybenzyl)-(4-nitrophenyl)carbonate (prepared as described in Example 10 from p-nitrophenyl chloroformate and 2-trifluoromethoxybenzyl alcohol) and 222 mg(0.75 mmol) of 1-[1-(4-cyanobenzyl)-2-methylimidazol-5-ylmethyl]-4-piperazine (prepared as described in Example 42, Step 1) was obtained the bis trifluoroacetic acid salt of the title compound as an amorphous fluffy white powder. High Res. FAB MS: M+theo.=514.2066, M+obs.=514.2053. 400 MHz $H^1$ NMR(DMSO-d$_6$): 2.39(br s, 4H), 2.55(s,3H), 3.19(br s, 4H), 3.59(s,2H), 5.16(s,2H), 5.60(s,2H), 7.36(d,2H), 7.40 (m,2H), 7.51(m,2H), 7.66(s,1H), 7.86(d,2H).

Example 44
1-[1-(2-4-cyanobenzyl)-2-methylimidazol-5-ylmethyl]-4-[2,3-(difluoromethylenedioxy)benzyloxycarbonyl]piperazine Using the reaction methods described in Example 10, from 223 mg (0.0.63 mmol) of 2-(difluoromethylenedioxybenzyl)-(4-nitrophenyl) carbonate (prepared as described in Example 10 from p-nitrophenyl chloroformate and 2,3-(difluoromethylenedioxy)benzyl alcohol) and 185 mg (0.63 mmol) of 1-[1-(4-cyano-benzyl)-2-methylimidazol-5-ylmethyl]-4-piperazine (prepared as described in Example 42, Step 1) was obtained the bis trifluoro-acetic acid salt of the title compound as an amorphous glass. High Res. FAB MS: M+theo.=510.1947, M+obs.=510.1964. 400 MHz $H^1$ NMR(DMSO-d$_6$): 2.41(br s, 4H), 2.57(s,3H), 3.20(br s, 4H), 3.58(s,2H), 5.18(s,2H), 5.60(s,2H), 7.20(m,2H), 7.38(m,3H), 7.67(s,1H), 7.87(d, 2H).

Example 45
1-[1-(4-cyanobenzyl)-2-methylimidazol-5-ylmethyl]-4-[3-ethoxybenzyloxy)carbonyl]piperazine Using the reaction methods described in Example 10, from 174 mg (0.55 mmol) of 3-(ethoxybenzyl)-(4-nitrophenyl)carbonate(prepared as described in Example 10 from p-nitrophenyl chloroformate and 2-ethoxybenzyl alcohol) and 162 mg(0.55 mmol) of 1-[1-(4-cyanobenzyl)-2-methylimidazol-5-ylmethyl]-4-piperazine (prepared as described in Example 42, Step 1) was obtained the bis trifluoroacetic acid salt of the title compound as an amorphous glass.

High Res. FAB MS: M+theo.=474.2500; obs.=474.2526. 400 MHz $H^1$ NMR(DMSO-d$_6$): 1.33(t,3H), 2.38(br s, 4H), 2.56(s,3H), 3.18(br s, 4H), 3.56(br s, 2H), 4.02(q,2H), 5.02(s,2H), 5.59(s,2H), 6.88(m,2H), 7.26(m,1H), 7.36(d, 2H), 7.66(s,1H), 7.87(d,2H).

Example 46
1-[1-(4-cyanobenzyl)-2-methylimidazol-5-ylmethyl]-4-[2-(difluoromethoxy)benzyloxycarbonyl]piperazine Using the reaction methods described in Example 10, from 214 mg (0.63 mmol) of 2-(difluoromethoxybenzyl)-(4-nitrophenyl)carbonate(prepared as described in Example 10 from p-nitrophenyl chloroformate and 2-(difluoromethoxybenzyl alcohol) and 185 mg(0.63 mmol) of 1-[1-(4-cyanobenzyl)-2-methylimidazol-5-ylmethyl]-4-piperazine (prepared as described in Example 42, Step 1) was obtained the bis trifluoroacetic acid salt of the title compound as an amorphous glassy solid. High Res. FAB MS: M+theo.=96.2155; obs.=495.2161. 400 MHz $H^1$ NMR (DMSO-d$_6$): 2.38(br s, 4H), 2.57(s,3H), 3.18(br s, 4H), 3.55(br s, 2H), 5.09(s,2H), 5.59(s,2H), 7.23(complex,3H), 7.39(complex,4H), 7.64(s,1H), 7.86(d,2H).

Example 47
1-[1-(4-cyanobenzyl)-2-methylimidazol-5-ylmethyl]-4-[2-(trifluoromethyl)benzyloxycarbonyl]piperazine Using the reaction methods described in Example 10, from 175 mg (0.51 mmol) of 2-(trifluoromethylbenzyl)-(4-nitrophenyl)carbonate(prepared as described in Example 10 from p-nitrophenyl chloroformate and 2-trifluormethylbenzyl alcohol) and 150 mg(0.51 mmol) of 1-[1-(4-cyanobenzyl-2-methylimidazol-5-ylmethyl]-4-piperazine (prepared as described in Example 42, Step 1) was obtained the bis trifluoroacetic acid salt of the title compound as an amorphous fluffy white powder. High Res. FAB MS: M+theo.=498.2111; obs.=498.2091. 400 MHz $H^1$ NMR(DMSO-d$_6$): 2.41(br s, 4H), 2.57(s,3H), 3.20(br s, 4H), 3.59(br s, 2H), 5.22(s,2H), 5.60(s,2H), 7.36(d,2H), 7.69 (complex,5H), 7.86(d,2H).

Example 48
1-[1-(4-cyanobenzyl)-2-methylimidazol-5-ylmethyl]-4-[2-(difluoromethoxy)-5-methylbenzyloxycarbonyl]piperazine Using the reaction methods described in Example 10, from 50 mg (0.14 mmol) of 2-(difluoromethoxy)-5-methybenzyl-(4-nitrophenyl)carbonate(prepared as described in Example 10 from p-nitrophenyl chloroformate and 2-(difluoromethoxy)-5-methyl-benzyl alcohol) and 42 mg(0.14 mmol) of 1-[1-(4cyanobenzyl)-2-methylimidazol-5-ylmethyl]-4-piperazine (prepared as described in Example 42, Step 1) was obtained the bis trifluoroacetic acid salt of the title compound as an amorphous glass. High Res. FAB MS: M+theo.=510.2311; obs.=510.2322. 400 MHz $H^1$ NMR (DMSO-$d_6$): 2.30(s,3H), 2.38(br s, 4H), 2.57(s,3H), 3.18(br s, 4H), 3.56(br s, 2H), 5.02(s,2H), 5.60(s,2H), 7.15(d,1H), 7.16(s,1H), 7.22(d,1H),7.23(s,1H), 7.65(s,1H), 7.89(d,2H).

Example 49

1-[1-(4-cyanobenzyl)-2-methylimidazol-5-ylmethyl]-4-[2-(trifluormethylsulfonyl)benzyloxycarbonyl]piperazine Using the reaction methods described in Example 10, from 191 mg (0.47 mmol) of 2-(trifluoromethylsulfonylbenzyl)-(4-nitrophenyl)carbonate (prepared as described in Example 10 from p-nitrophenyl chloroformate and 2-(trifluoromethyl-sulfony)lbenzyl alcohol) and 139 mg(0.47 mmol) of 1-[1-(4-cyanobenzyl)-2-methylimidazol-5-ylmethyl]-4-piperazine (prepared as described in Example 42, Step 1) was obtained the bis trifluoroacetic acid salt of the title compound as an oil. High Res. FAB MS: M+theo.=562.1730; obs.=562.1723. 400 MHz $H^1$ NMR(DMSO-$d_6$): 2.38(br s, 4H), 2.57(s,3H), 3.20 (br s, 4H), 3.52(br s, 2H), 5.44(s,2H), 5.61(s,2H), 7.39(d, 2H), 7.64(s,1H), 7.81(t,1H), 7.89(d,2H), 8.05(t,1H), 8.19(d, 1H).

Example 50

(±)-1-[1-(4-cyanobenzyl)-2-methylimidazol-5-ylmethyl]-4-[2-(triflurormethylsulfoxy)benzyloxycarbonyl]piperazine Using the reaction methods described in Example 10, from 60 mg (0.15 mmol) of (±)-2-(trifluoromethylsulfoxylbenzyl)-(4-nitrophenyl)carbonate (prepared as described in Example 10 from p-nitrophenyl chloroformate and (±)-2-(trifluoromethylsulfoxy)lbenzyl alcohol) and 46 mg(0.15 mmol) of 1-[1-(4-cyanobenzyl-2-methylimidazol-5-ylmethyl]-4-piperazine (prepared as described in Example 42, Step 1) was obtained the bis trifluoroacetic acid salt of the title compound as an amorphous white powder. FAB MS: M+=546.18. 400 MHz $H^1$ NMR(DMSO-$d_6$): 2.31(br s, 4H), 2.58(s,3H), 3.08(br s, 4H), 3.48(br s, 2H), 5.24(s,2H), 5.59(s,2H), 7.37(d,2H), 7.63(d, 1H), 7.64(s,1H), 7.77(m,2H), 7.85(d,2H), 8.03(d,1H).

Example 51

1-[1-(4-cyanobenzyl)-2-methylimidazol-5-ylmethyl]-4-[2-(triflurormethylthio)benzyloxycarbonyl]piperazine Using the reaction methods described in Example 10, from 191 mg (0.51 mmol) of 2-[(trifluoromethylthio)benzyl]-(4-nitrophenyl)carbonate (prepared as described in Example 10 from p-nitrophenyl chloroformate and 2-(trifluoromethylthio)lbenzyl alcohol) and 150 mg(0.51 mmol) of 1-[1-(4-cyanobenzyl)-2-methyl-imidazol-5-ylmethyl]-4-piperazine (prepared as described in Example 42, Step 1) was obtained the bis trifluoroacetic acid salt of the title compound as an amorphous tacky white powder. High Res. FAB MS: M+theo.=530.1832; obs.=530.1852. 400 MHz $H^1$ NMR(DMSO-$d_6$): 2.28(br s, 4H), 2.53(s,3H), 3.12(br s, 4H), 3.44(br s, 2H), 5.24(s,2H), 5.57(s,2H), 7.37 (d,2H), 7.58(complex,4H), 7.78(d,1H), 7.86(d,2H).

Example 52

1-[1-(4'-Cyanobenzyl)imidazole-5-ylmethyl]-4-[2-(2,2,2-trifluoroethoxy)benzyloxycarbonyl [piperazine To a round bottomed flask were added 2-[2-(2,2,2-trifluoroethoxyl)benzyl-(4-nitrophenyl)-carbonate (prepared by the synthetic method described in Example 10) (152.0 mg, 0.4 mmol) along with 1-[1-(4-cyanobenzyl)imidazole-5-ylmethyl]-piperazine (prepared as described in Example 2) (110 mg, 0.4 mmol), diiso-propylethylamine(0.4 ml, 2.2 mmol) and dichloromethane (5.0 ml). The reaction stirred at RT for 18 hr. The solvent was removed under vacuum and the residue dissolved into ethyl acetate(25.0 ml). The organic layer was washed with dilute ammonium hydroxide solution. The reaction was dried ($MgSO_4$) and the solvent removed to give an oil which was purified using a prep HPLC column. After lyophilization 1-[1-(4'-Cyano-benzyl)imidazole-5-ylmethyl]-4-[2-(2,2,2-trifluoro-ethoxy)benzyl-oxycarbonyl]piperazine diflouroacetic acid salt was isolated. 400 Mhz $H^1$ NMR ($CD_3OD$): 2.37(br s,4H), 2.58(s,3H), 3.26(br s,4H), 3.50(br s,2H), 4.57(q, 2H), 5.13(s,2H), 5.63 (s,2H), 7.04(d,2H), 7.33(m,4H), 7.50(s,1H)., 7.70(d,2H). High res. FAB MS: Theoretical Mass 528.2217, Measured Mass 528.2229 ($C_{27}H_{28}F_3N_5O_3+H^+$)

Example 53

(R/S) 2-[4-(2-ethoxyphenyl)methyloxycarbonyl-1-piperazine)]-2-[1-(4-cyanobenzyl)-2-methyl-5-imadazol] acetonitrile To a round bottomed flask were added 1-(4-cyanobenzyl)-2-methyl-5-formylimidazole (prepared as described in Example 13, Step 1) (225.25 mg, 1.0 mmol), 2-ethoxybenzyl-1-piperazinecarboxylate(300.78 mg, 1.0 mmol), KCN(65.12 mg, 1.0 mmol), acetic acid(100 ul,1.50 mmol), and methanol(2.0 ml). After 1.0 hr at RT sodium carbonate(84.01 mg, 1.0 mmol) was added and the reaction heated at 80° C. for 2.0 hr. The reaction was cooled and trifluoroacetic acid (0.5 ml) added. After the effervescence had subsided, the volume was adjusted to 5.0 ml with methanol and the mixture purified on a prep HPLC column. After lyophilization, (R/S) 2-[4-(2-ethoxyphenyl)methyloxycarbonyl-1-piperazine)]-2-[1-(4-cyanobenzyl)-2-methyl-5-imadazol]acetonitrile was isolated. 400 Mhz $H^1$ NMR ($CD_3OD$): 1.38(t,3H), 2.46(br s,4H), 2.61(s,3H), 3.13 (br s,2H), 3.24(br s,2H), 4.06(q, 2H), 5.13(s,2H), 5.31(s, 1H), 5.58(q,2H), 6.93(m,2H), 7.25(m,2H), 7.32(d,2H), 7.79 (d,2H), 7.81(s,1H). High res. FAB MS: Theoretical Mass 499.2458, Measured Mass 499.2457 ($C_{28}H_{30}N_6O_3+H^+$)

Example 54

1-(4'-Cyanobenzyl)-2-methyl-imidazol-5-ylmethyl Piperazine-4-(N-2-trifluoromethoxybenzyl)carboxamide Step 1

2-(Trifluoromethoxy)benzylisocyanate

To a methylene chloride solution of commercially available 2-(trifluoromethoxy)benzyl amine (2.81 mmol) at 0° C. was added solid Proton sponge (2.81 mmol) then a 20% solution of phosgene in toluene (2.81 mmol). The solution was stirred at 25° C. for 1 hour and then washed with 1N HCl (40 mL). The methylene chloride was then dried with sodium sulfate and evaporated. $^1$H-NMR ($CDCl_3$): 7.5 ppm (d, 1H); 7.4 ppm (m, 2H); 7.3 ppm (d, 1H); 4.6 ppm (s, 2H).

Step 2

1-(4'-Cyanobenzyl)-2-methyl-imidazol-5-ylmethyl Piperazine-4-(N-2-trifluoromethoxybenzyl)-carboxamide To the product from Example 42, Step 1 (0.254 mmol) and the product from Step 1 (0.254 mmol) in methylene chloride was added diisopropylethyl amine (0.51 mmol). After stirring for 1 hour the reaction was evaporated and purified via preparative hplc and isolated via lyophilization.

HI-RES FAB-MS: calc: 513.2220 found: 513.2226. ¹H-NMR (CD₃OD): 7.75 ppm (d, 2H); 7.4–7.2 ppm (m, 6H); 7.0 ppm (s, 1H); 5.45 ppm (s, 2H); 4.4 ppm (d, 2H); 3.4 ppm (s, 2H); 3.2 ppm (m, 4H); 2.3 ppm (m, 7H).

Example 55
1-(4'-Cyanobenzyl)-2-methyl-imidazol-5-ylmethyl Piperazine-4-{N-[2-(3-trifluoromethylphenyl)ethyl]}carboxamide Step 1
2-(3-Trifluoromethylphenyl)ethylisocyanate To a methylene chloride solution of commercially available 2-(3-trifluoromethylphenyl)ethylamine (5.65 mmol) at 0° C. was added solid Proton sponge (5.65 mmol) then a 20% solution of phosgene in toluene (5.65 mmol). The solution was stirred at 25° C. for 1 hour and then washed with 1N HCl (40 mL). The methylene chloride was then dried with sodium sulfate and evaporated. ¹H-NMR (CDCl₃): 7.5 ppm (m, 4H); 3.6 ppm (t, 2H); 2.95 ppm (t, 2H).

Step 2
1-(4'-Cyanobenzyl)-2-methyl-imidazol-5-ylmethyl Piperazine-4-{N-[2-(3-trifluoromethylphenyl)-ethyl]}carboxamide To the product from Example 42, Step 1 (0.54 mmol) and the product from Step 1 (0.614 mmol) in methylene chloride was added diisopropylethyl amine (1.08 mmol). After stirring for 1 hour the reaction was evaporated and purified via preparative hplc and isolated via lyophilization. HI-RES MS: calc: 511.2438 found: 511.2438. ¹H-NMR (CD₃OD): 7.73 ppm (d, 2H); 7.47 ppm (m, 4H); 7.19 ppm (d, 2H); 6.94 ppm (s, 1H); 5.45 ppm (s, 2H); 3.37 ppm(m, 4H); 3.10 ppm (m, 4H); 2.84 ppm (t, 2H); 2.33 ppm (s, 3H); 2.28 ppm (t, 4H).

Example 56
1-(4'-Cyanobenzyl)-2-methyl-imidazol-5-ylmethyl Piperazine-4-N-(2-fluoro-5-trifluoromethylbenzyl) carboxamide Step 1
2-Fluoro-5-trifluoromethylbenzylisocyanate To a methylene chloride solution of commercially available 2-fluoro-5-trifluoromethyl benzyl amine(5.23 mmol) at 0° C. was added solid Proton sponge (5.23 mmol) then a 20% solution of phosgene in toluene (5.23 mmol). The solution was stirred at 25° C. for 1 hour and then washed with 1N HCl (40 mL). The methylene chloride was then dried with sodium sulfate and evaporated to provide the title compound. ¹H-NMR (CDCl₃): 7.7 ppm (t, 1H); 7.60 ppm (m, 1H); 7.2 ppm (m, 1H); 4.64 ppm (s, 2H).

Step 2
1-(4'-Cyanobenzyl)-2-methyl-imidazol-5-ylmethyl Piperazine-4-N-(2-fluoro-5-trifluoromethylbenzyl)-carboxamide To the product from Example 42, Step 1 (0.54 mmol) and the product from Step 1 (0.51 mmol) in methylene chloride was added diisopropylethyl amine (1.02 mmol). After stirring for 1 hour the reaction was evaporated and purified via preparative hplc and the title compound isolated via lyophilization. HI-RES MS: calc: 515.2177 found: 515.2192. ¹H-NMR (CD₃OD): 7.74 ppm (d, 2H); 7.60 (m, 2H); 7.24 ppm (m, 3H); 7.14 ppm (s, 1H); 5.24 ppm (s, 2H); 4.42 ppm (s, 2H); 3.43 ppm (s, 2H); 3.20 ppm (m, 4H); 2.42 ppm (s, 3H); 2.34 ppm (m, 4H).

Example 57
1-(4'-Cyanobenzyl)-2-methyl Imidazol-5-ylmethyl Piperazine-4-carboxylic Acid-(2-fluoro-3-trifluoromethyl)benzyl Ester Step 1
2-Fluoro-3-trifluoromethylbenzyl-(4-nitrophenyl)-carbonate A THF:acetonitrile (7:1, 10 mL) solution of 4-nitrophenyl chloroformate (4.79 mmol)was added to a THF:acetonitrile (7:1, 20 mL) solution of 2-fluoro-3-trifluoromethylbenzyl alcohol (4.74 mmol) at 25° C. and then stirred for 0.25 hour. Pyridine (4.79 mmol) was then added dropwise over 4 minutes. Stirring was continued for 2 hours at 25° C. and then the reaction was diluted with ethyl acetate and washed with water, a saturated sodium chloride solution, dried with sodium sulfate and then evaporated and purified on a silica column eluted with EtOAc:hex (1:9 to 3:7) to provide the title compound. ¹H-NMR (CDCl₃): 8.3 ppm (d, 2H); 7.7 ppm (m, 2H); 7.4 ppm (d, 2H); 7.31 ppm (t, 1H); 5.4 ppm (s, 2H).

Step 2
1-(4'-Cyanobenzyl)-2-methyl Imidazol-5-ylmethyl Piperazine-4-carboxylic Acid-(2-fluoro-3-trifluoromethyl)benzyl Ester The product from Step 1 (0.516 mmol) and the product Example 42, Step 1 (70.54 mmol) were dissolved in methylene chloride and then diisopropylethyl amine (1.13 mmol) was added followed by stirring at 45° C. for 18 hours. The product was purified via preperative hplc and isolated via lyophilization to provide the title compound. HI-RES FAB-MS: calc: 516.2017 found: 516.2047. ¹H-NMR (CD₃OD): 7.75 ppm (d, 2H); 7.67 ppm (m, 2H); 7.35 ppm (t, 1H); 7.23 ppm (d, 2H); 7.15 ppm (s, 1H); 5.51 ppm (s, 2H); 5.21 ppm (s, 2H); 3.42 ppm (s, 2H); 3.25 ppm (s, 4H); 2.42 ppm (s, 3H); 2.33 ppm (s, 4H).

Example 58
Preparation of Carbamates From Alcohols

To each of eleven previously tared screw cap test tubes was added approxmately 1.25 equivalents of one of the eleven alcohols. After determining the weights of alcohols by difference the appropriate amount of p-nitrophenyl chloroformate (1.27 equivalents) was added to each tube as a freshly made tetrahydrofuran:acetonitrile (7:1) solution. This was stirred for 10 minutes and then pryidine (1.37 equivalents) was added to each tube followed by stirring for 1.5 hours. Each tube was diluted with 1.5 mL each of ethyl acetate and water. The aqueous layer was removed and the organic layer was rotary speed evaporated to a pellet. To each tube was added 1.0 mL of ethyl actate:DCM:methanol (1:1:0.1) and 0.1 mmol of a stock DMF solution of 1-(4'-Cyanobenzyl)imidazol-5-ylmethyl piperazine (prepared as described in Example 2) and 0.2 mmol DIEA. Stir for 18 hours. To each tube was added 1.0 mL of ethyl acetate then each tube was washed with 5×1 mL of 1.0N NaOH. The organic layer was then rotary speed evaporated to a pellet. The resulting pellet was dissolved in 2.0 mL of DMSO and submitted for LC and HI-RES Mass spec analysis. The completness of reaction was estimated by comparing the AUC of each reaction against an independently prepared standard of known concentration that was also prepared in the library run. The following compounds were prepared by this method:

1-[(4-cyanophenyl)methylimidazol-5-ylmethyl] piperazine-4-(2,4-dimethylbenzyloxycarbonyl)
HI-RES MS: calc. 444.239, found 444.239

1-[(4-cyanophenyl)methylimidazol-5-ylmethyl]piperazine-4-(2-methylbenzyloxycarbonyl)
HI-RES MS: calc. 430.2237, found 430.2257

1-[(4-cyanophenyl)methylimidazol-5-ylmethyl]piperazine-4-(4'-acetamidobenzyloxycarbonyl)
HI-RES MS: calc. 473.2295, found 473.229

1-[(4-cyanophenyl)methylimidazol-5-ylmethyl]piperazine-4-[(3'-methylbenzyloxycarbonyl)
HI-RES MS: calc. 430.2237, found 430.223

1-[(4-cyanophenyl)methylimidazol-5-ylmethyl]piperazine-4-(2'-methoxybenzyloxycarbonyl)
HI-RES MS: calc. 446.2186, found 446.2173

1-[(4-cyanophenyl)methylimidazol-5-ylmethyl]piperazine-4-(3'-methoxybenzyloxycarbonyl)
HI-RES MS: calc. 446.2186, found 446.2163

1-[(4-cyanophenyl)methylimidazol-5-ylmethyl]piperazine-4-(1-oxypyridine-3-methyloxycarbonyl)
HI-RES MS: calc. 433.1982, found 433.1968

1-[(4-cyanophenyl)methylimidazol-5-ylmethyl]piperazine-4-(3-pyridinemethyloxycarbonyl)
HI-RES MS: calc. 417.2033, found 417.2018

1-[(4-cyanophenyl)methylimidazol-5-ylmethyl]piperazine-4-(4'-pyridinemethyloxycarbonyl)
HI-RES MS: calc. 417.2033, found 417.2017

1-[(4-cyanophenyl)methylimidazol-5-ylmethyl]piperazine-4-(2',5'-dimethylbenzyloxycarbonyl)
HI-RES MS: calc. 444.2394, found 444.2375

1-[(4-cyanophenyl)methylimidazol-5-ylmethyl]piperazine-4-[(1,3-benzodioxolan-5-methyl)oxycarbonyl]
HI-RES MS: calc. 460.1979, found 460.1962

Example 59
In vitro Inhibition of ras Farnesyl Transferase

Transferase Assays. Isoprenyl-protein transferase activity assays are carried out at 30° C. unless noted otherwise. A typical reaction contains (in a final volume of 50 μL): [$^3$H]farnesyl diphosphate, Ras protein, 50 mM HEPES, pH 7.5, 5 mM MgCl$_2$, 5 mM dithiothreitol, 10 μM ZnCl$_2$, 0.1% polyethyleneglycol (PEG) (15,000–20,000 mw) and isoprenyl-protein transferase. The FPTase employed in the assay is prepared by recombinant expression as described in Omer, C. A., Kral, A. M., Diehl, R. E., Prendergast, G. C., Powers, S., Allen, C. M., Gibbs, J. B. and Kohl, N. E. (1993) Biochemistry 32:5167–5176. After thermally pre-equilibrating the assay mixture in the absence of enzyme, reactions are initiated by the addition of isoprenyl-protein transferase and stopped at timed intervals (typically 15 min) by the addition of 1 M HCl in ethanol (1 mL). The quenched reactions are allowed to stand for 15 m (to complete the precipitation process). After adding 2 mL of 100% ethanol, the reactions are vacuum-filtered through Whatman GF/C filters. Filters are washed four times with 2 mL aliquots of 100% ethanol, mixed with scintillation fluid (10 mL) and then counted in a Beckman LS3801 scintillation counter.

For inhibition studies, assays are run as described above, except inhibitors are prepared as concentrated solutions in 100% dimethyl sulfoxide and then diluted 20-fold into the enzyme assay mixture. Substrate concentrations for inhibitor IC$_{50}$ determinations are as follows: FTase, 650 nM Ras-CVLS (SEQ.ID.NO.: 1), 100 nM farnesyl diphosphate.

The compounds of the instant invention described in the above Examples 3–58 were tested for inhibitory activity against human FPTase by the assay described above and were found to have an IC$_{50}$ of ≦5 μM.

Example 60
Modified In vitro GGTase Inhibition Assay

The modified geranylgeranyl-protein transferase inhibition assay is carried out at room temperature. A typical reaction contains (in a final volume of 50 μL): [$^3$H] geranylgeranyl diphosphate, biotinylated Ras peptide, 50 mM HEPES, pH 7.5, a modulating anion (for example 10 mM glycerophosphate or 5 mM ATP), 5 mM MgCl$_2$, 10 μM ZnCl$_2$, 0.1% PEG (15,000–20,000 mw), 2 mM dithiothreitol, and geranylgeranyl-protein transferase type I(GGTase). The GGTase-type I enzyme employed in the assay is prepared as described in U.S. Pat. No. 5,470,832, incorporated by reference. The Ras peptide is derived from the K4B-Ras protein and has the following sequence: biotinyl-GKKKKKKSKTKCVIM (single amino acid code) (SEQ.ID.NO.: 2). Reactions are initiated by the addition of GGTase and stopped at timed intervals (typically 15 min) by the addition of 200 μL of a 3 mg/mL suspension of streptavidin SPA beads (Scintillation Proximity Assay beads, Amersham) in 0.2 M sodium phosphate, pH 4, containing 50 mM EDTA, and 0.5% BSA. The quenched reactions are allowed to stand for 2 hours before analysis on a Packard TopCount scintillation counter.

For inhibition studies, assays are run as described above, except inhibitors are prepared as concentrated solutions in 100% dimethyl sulfoxide and then diluted 25-fold into the enzyme assay mixture. IC$_{50}$ values are determined with Ras peptide near K$_M$ concentrations. Enzyme and substrate concentrations for inhibitor IC$_{50}$ determinations are as follows: 75 pM GGTase-I, 1.6 μM Ras peptide, 100 nM geranylgeranyl diphosphate.

The compounds of the instant invention described in the above Examples 3–58 were tested for inhibitory activity against human GGTase-type I by the assay described above and were found to have an IC$_{50}$ of ≦5 μM.

Example 61
Cell-based In vitro ras Farnesylation Assay

The cell line used in this assay is a v-ras line derived from either Rat1 or NIH3T3 cells, which expressed viral Ha-ras p21. The assay is performed essentially as described in DeClue, J. E. et al., Cancer Research 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labeled in 3 ml methionine-free DMEM supplemented with 10% regular DMEM, 2% fetal bovine serum and 400 μCi[$^{35}$S]methionine (1000 Ci/mmol). After an additional 20 hours, the cells are lysed in 1 ml lysis buffer (1% NP40/20 mM HEPES, pH 7.5/5 mM MgCl$_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., J. Virol. 43:294–304, (1982)). Following a 2 hour antibody incubation at 4° C., 200 μl of a 25% suspension of protein A-Sepharose coated with rabbit anti rat IgG is added for 45 min. The immuno-precipitates are washed four times with IP buffer (20 nM HEPES, pH 7.5/1 mM EDTA/1% Triton X-100.0.5% deoxycholate/0.1%/SDS/0.1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

Example 62
Cell-based In vitro Growth Inhibition Assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of $1\times10^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

Example 63
Construction of SEAP Reporter Plasmid pDSE100

The SEAP reporter plasmid, pDSE100 was constructed by ligating a restriction fragment containing the SEAP coding sequence into the plasmid pCMV-RE-AKI. The SEAP gene is derived from the plasmid pSEAP2-Basic (Clontech, Palo Alto, Calif.). The plasmid pCMV-RE-AKI was constructed by Deborah Jones (Merck) and contains 5 sequential copies of the 'dyad symmetry response element' cloned upstream of a 'CAT-TATA' sequence derived from the cytomegalovirus immediate early promoter. The plasmid also contains a bovine growth hormone poly-A sequence.

The plasmid, pDSE100 was constructed as follows. A restriction fragment encoding the SEAP coding sequence was cut out of the plasmid pSEAP2-Basic using the restriction enzymes EcoR1 and HpaI. The ends of the linear DNA fragments were filled in with the Klenow fragment of *E. coli* DNA Polymerase I. The 'blunt ended' DNA containing the SEAP gene was isolated by electrophoresing the digest in an agarose gel and cutting out the 1694 base pair fragment. The vector plasmid pCMV-RE-AKI was linearized with the restriction enzyme Bgl-II and the ends filled in with Klenow DNA Polymerase I. The SEAP DNA fragment was blunt end ligated into the pCMV-RE-AKI vector and the ligation products were transformed into DH5-alpha *E. coli* cells (Gibco-BRL). Transformants were screened for the proper insert and then mapped for restriction fragment orientation. Properly oriented recombinant constructs were sequenced across the cloning junctions to verify the correct sequence. The resulting plasmid contains the SEAP coding sequence downstream of the DSE and CAT-TATA promoter elements and upstream of the BGH poly-A sequence.

Alternative Construction of SEAP Reporter Plasmid, pDSE101

The SEAP repotrer plasmid, pDSE101 is also constructed by ligating a restriction fragment containing the SEAP coding sequence into the plasmid pCMV-RE-AKI. The SEAP gene is derived from plasmid pGEM7zf(−)/SEAP.

The plasmid pDSE101 was constructed as follows: A restriction fragment containing part of the SEAP gene coding sequence was cut out of the plasmid pGEM7zf(−)/SEAP using the restriction enzymes Apa I and KpnI. The ends of the linear DNA fragments were chewed back with the Klenow fragment of *E. coli* DNA Polymerase I. The "blunt ended" DNA containing the truncated SEAP gene was isolated by electrophoresing the digest in an agarose gel and cutting out the 1910 base pair fragment. This 1910 base pair fragment was ligated into the plasmid PCMV-RE-AKI which had been cut with Bgl-II and filled in with *E. coli* Klenow fragment DNA polymerase. Recombinant plasmids were screened for insert orientation and sequenced through the ligated junctions. The plasmid pCMV-RE-AKI is derived from plasmid pCMVIE-AKI-DHFR (Whang, Y., Silberklang, M., Morgan, A., Munshi, S., Lenny, A. B., Ellis, R. W., and Kieff, E. (1987) J. Virol., 61, 1796–1807) by removing an EcoRI fragment containing the DHFR and Neomycin markers. Five copies of the fos promoter serum response element were inserted as described previously (Jones, R. E., Defeo-Jones, D., McAvoy, E. M., Vuocolo, G. A., Wegrzyn, R. J., Haskell, K. M. and Oliff, A. (1991) Oncogene, 6, 745–751) to create plasmid pCMV-RE-AKI.

The plasmid pGEM7zf(−)/SEAP was constructed as follows. The SEAP gene was PCRed, in two segments from a human placenta cDNA library (Clontech) using the following oligos.

Sense strand N-terminal SEAP:

5' GAGAGGGAATTCGGGCCCTTCCTGCAT-
GCTGCTGCTGCTGCTGCTGGGC 3'  (SE Q.ID NO.:3)

Antisense strand N-terminal SEAP:

5' GAGAGAGCTCGAGGTTAACCCGGGT-
GCGCGGCGTCGGTGGT 3'  (SEQ.ID.NO.:4)

Sense strand C-terninal SEAP:

5' GAGAGAGTCTAGAGTTAACCCGTGGTC-
CCCGCGTTGCTTCCT 3'  (SEQ.ID.NO.:5)

Antisense strand C-terminal SEAP:

5' GAAGAGGAAGCTTGGTACCGC-
CACTGGGCTGTAGGTGGTGGCT 3'  (SEQ.ID.NO.:6)

The N-terminal oligos (SEQ.ID.NO.: 4 and SEQ.ID.NO.: 5) were used to generate a 1560 bp N-terminal PCR product that contained EcoRI and HpaI restriction sites at the ends. The Antisense N-terminal oligo (SEQ.ID.NO.: 4) introduces an internal translation STOP codon within the SEAP gene along with the HpaI site. The C-terminal oligos (SEQ.ID.NO.: 5 and SEQ.ID.NO.: 6) were used to amplify a 412 bp C-terminal PCR product containing HpaI and HindIII restriction sites. The sense strand C-terminal oligo (SEQ.ID.NO.: 5) introduces the internal STOP codon as well as the HpaI site. Next, the N-terminal amplicon was digested with EcoRI and HpaI while the C-terminal amplicon was digested with HpaI and HindIII. The two fragments comprising each end of the SEAP gene were isolated by electrophoresing the digest in an agarose gel and isolating the 1560 and 412 base pair fragments. These two fragments were then co-ligated into the vector pGEM7zf(−) (Promega) which had been restriction digested with EcoRI and HindIII and isolated on an agarose gel. The resulting clone, pGEM7zf(−)/SEAP contains the coding sequence for the SEAP gene from amino acids.

Construction of a Constitutively Expressing SEAP Plasmid pCMV-SEAP

An expression plasmid constitutively expressing the SEAP protein was created by placing the sequence encoding a truncated SEAP gene downstream of the cytomegalovirus (CMV) IE-1 promoter. The expression plasmid also includes the CMV intron A region 5' to the SEAP gene as well as the 3' untranslated region of the bovine growth hormone gene 3' to the SEAP gene.

The plasmid pCMVIE-AKI-DHFR (Whang et al, 1987) containing the CMV immediate early promoter was cut with EcoRI generating two fragments. The vector fragment was isolated by agarose electrophoresis and religated. The resulting plasmid is named pCMV-AKI. Next, the cytomegalovirus intron A nucleotide sequence was inserted downstream of the CMV IE1 promter in PCMV-AKI. The intron A sequence was isolated from a genomic clone bank and subcloned into pBR322 to generate plasmid p16T-286. The intron A sequence was mutated at nucleotide 1856 (nucleotide numbering as in Chapman, B. S., Thayer, R. M., Vincent, K. A. and Haigwood, N. L., Nuc.Acids Res. 19, 3979–3986) to remove a SacI restriction site using site directed mutagenesis. The mutated intron A sequence was PCRed from the plasmid p16T-287 using the following oligos.

Sense strand:

5' GGCAGAGCTCGTTTAGTGAACCGTCAG 3'(SEQ.ID.NO.: 7)

Antisense strand:

5' GAGAGATCTCAAGGACGGTGACTGCAG 3(SEQ.ID.NO.: 8)

These two oligos generate a 991 base pair fragment with a SacI site incorporated by the sense oligo and a Bgl-II fragment incorporated by the antisense oligo. The PCR fragment is trimmed with SacI and Bgl-II and isolated on an agarose gel. The vector pCMV-AKI is cut with SacI and Bgl-II and the larger vector fragment isolated by agarose gel electrophoresis. The two gel isolated fragments are ligated at their respective SacI and Bgl-II sites to create plasmid pCMV-AKI-InA.

The DNA sequence encoding the truncated SEAP gene is inserted into the pCMV-AKI-InA plasmid at the Bgl-II site of the vector. The SEAP gene is cut out of plasmid pGEM7zf (−)/SEAP (described above) using EcoRI and HindIII. The fragment is filled in with Klenow DNA polymerase and the 1970 base pair fragment isolated from the vector fragment by agarose gel electrophoresis. The pCMV-AKI-InA vector is prepared by digesting with Bgl-II and filling in the ends with Klenow DNA polymerase. The final construct is generated by blunt end ligating the SEAP fragment into the pCMV-AKI-InA vector. Transformants were screened for the proper insert and then mapped for restriction fragment orientation. Properly oriented recombinant constructs were sequenced across the cloning junctions to verify the correct sequence. The resulting plasmid, named pCMV-SEAP, contains a modified SEAP sequence downstream of the cytomegalovirus immediately early promoter IE-1 and intron A sequence and upstream of the bovine growth hormone poly-A sequence. The plasmid expresses SEAP in a constitutive manner when transfected into mammalian cells.

Cloning of a Myristylated Viral-H-ras Expression Plasmid

A DNA fragment containing viral-H-ras can be PCRed from plasmid "H-1" (Ellis R. et al. J. Virol. 36, 408, 1980) or "HB-11 (deposited in the ATCC under Budapest Treaty on Aug. 27, 1997, and designated ATCC 209,218) using the following oligos.

Sense strand:

5'TCTCCTCGAGGCCACCATGGGGAGTAG-
CAAGAGCAAGCCTAAGGACCCCAGC-
CAGCGCCGGATGACAGAATACAAGCTT
GTGGTGG 3'.                                    (SEQ.ID.NO.: 9)

Antisense:

5'CACATCTAGATCAGGACAGCACAGACTT
GCAGC 3'.                                       (SEQ.ID.NO.: 10)

A sequence encoding the first 15 aminoacids of the v-src gene, containing a myristylation site, is incorporated into the sense strand oligo. The sense strand oligo also optimizes the 'Kozak' translation initiation sequence immediately 5' to the ATG start site. To prevent prenylation at the viral-ras C-terminus, cysteine 186 would be mutated to a serine by substituting a G residue for a C residue in the C-terminal antisense oligo. The PCR primer oligos introduce an XhoI site at the 5' end and a XbaI site at the 3'end. The XhoI-XbaI fragment can be ligated into the mammalian expression plasmid pCI (Promega) cut with XhoI and XbaI. This results in a plasmid in which the recombinant myr-viral-H-ras gene is constitutively transcribed from the CMV promoter of the pCI vector.

Cloning of a Viral-H-ras-CVLL Expression Plasmid

A viral-H-ras clone with a C-terminal sequence encoding the amino acids CVLL can be cloned from the plasmid "H-1" (Ellis R. et al. J. Virol. 36, 408, 1980) or "HB-11 (deposited in the ATCC under Budapest Treaty on Aug. 27, 1997, and designated ATCC 209,218) by PCR using the following oligos.

Sense strand:

5'TCTCCTCGAGGCCACCATGACAGAATA-
CAAGCTTGTGGTGG-3'                (SEQ.ID.NO.: 11)

Antisense strand:

5°CACTCTAGACTGGTGTCAGAGCAGCACACACTTGCAGC-
3'                                              (SEQ.ID.NO.: 12)

The sense strand oligo optimizes the 'Kozak' sequence and adds an XhoI site. The antisense strand mutates serine 189 to leucine and adds an XbaI site. The PCR fragment can be trimmed with XhoI and XbaI and ligated into the XhoI-XbaI cut vector pCI (Promega). This results in a plasmid in which the mutated viral-H-ras-CVLL gene is constitutively transcribed from the CMV promoter of the pCI vector.

Cloning of c-H-ras-Leu61 Expression Plasmid

The human c-H-ras gene can be PCRed from a human cerebral cortex cDNA library (Clontech) using the following oligonucleotide primers.

Sense strand:

5'-GAGAGAATTCGCCACCATGACGGAATATAAGCTGGTGG-
3'                                              (SEQ.ID.NO.: 13)

Antisense strand:

5'-GAGAGTCGACGCGTCAGGAGAGCACA
CACTTGC-3'                                     (SEQ.ID.NO.: 14)

The primers will amplify a c-H-ras encoding DNA fragment with the primers contributing an optimized 'Kozak' translation start sequence, an EcoRI site at the N-terminus and a Sal I stite at the C-terminal end. After trimming the ends of the PCR product with EcoRI and Sal I, the c-H-ras fragment can be ligated ligated into an EcoRI-Sal I cut mutagenesis vector pAlter-1 (Promega). Mutation of glutamine-61 to a leucine can be accomplished using the manufacturer's protocols and the following oligonucleotide:

5'-CCGCCGGCCTGGAGGAGTACAG-3'    (SEQ.ID.NO.: 15)

After selection and sequencing for the correct nucleotide substitution, the mutated c-H-ras-Leu61 can be excised from the pAlter-1 vector, using EcoRI and Sal I, and be directly ligated into the vector pCI (Promega) which has been digested with EcoRI and Sal I. The new recombinant plasmid will constitutively transcribe c-H-ras-Leu61 from the CMV promoter of the pCI vector.

Cloning of a c-N-ras-Val-12 Expression Plasmid

The human c-N-ras gene can be PCRed from a human cerebral cortex cDNA library (Clontech) using the following oligonucleotide primers.

Sense strand:

5'-GAGAGAATTCGCCACCATGACTGAGTACAAACTGGTGG-3' (SEQ.ID.NO.: 16)

Antisense strand:

5'-GAGAGTCGACTTGTTACATCACCACAC ATGGC-3' (SEQ.ID.NO.: 17)

The primers will amplify a c-N-ras encoding DNA fragment with the primers contributing an optimized 'Kozak' translation start sequence, an EcoRI site at the N-terminus and a Sal I stite at the C-terminal end. After trimming the ends of the PCR product with EcoRI and Sal I, the c-N-ras fragment can be ligated into an EcoRI-Sal I cut mutagenesis vector pAlter-1 (Promega). Mutation of glycine-12 to a valine can be accomplished using the manufacturer's protocols and the following oligonucleotide:

5'-GTTGGAGCAGTTGGTGTTGGG-3' (SEQ.ID.NO.: 18)

After selection and sequencing for the correct nucleotide substitution, the mutated c-N-ras-Val-12 can be excised from the pAlter-1 vector, using EcoRI and Sal I, and be directly ligated into the vector pCI (Promega) which has been digested with EcoRI and Sal I. The new recombinant plasmid will constitutively transcribe c-N-ras-Val-12 from the CMV promoter of the pCI vector.

Cloning of a c-K-ras-Val-12 Expression Plasmid

The human c-K-ras gene can be PCRed from a human cerebral cortex cDNA library (Clontech) using the following oligonucleotide primers.

Sense strand:

5'-GAGAGGTACCGCCACCATGACTGAA TATAAACTTGTGG3' (SEQ.ID.NO.: 19)

Antisense strand:

5'-CTCTGTCGACGTATTTACATAATTACAC ACTTTGTC-3' (SEQ.ID.NO.: 20)

The primers will amplify a c-K-ras encoding DNA fragment with the primers contributing an optimized 'Kozak' translation start sequence, a KpnI site at the N-terminus and a Sal I stite at the C-terminal end. After trimming the ends of the PCR product with Kpn I and Sal I, the c-K-ras fragment can be ligated into a KpnI-Sal I cut mutagenesis vector pAlter-1 (Promega). Mutation of cysteine-12 to a valine can be accomplished using the manufacturer's protocols and the following oligonucleotide:

5'-GTAGTTGGAGCTGTTGGCGTAGGC-3' (SEQ.ID.NO.: 21)

After selection and sequencing for the correct nucleotide substitution, the mutated c-K-ras-Val-12 can be excised from the pAlter-1 vector, using KpnI and Sal I, and be directly ligated into the vector pCI (Promega) which has been digested with KpnI and Sal I. The new recombinant plasmid will constitutively transcribe c-K-ras-Val-12 from the CMV promoter of the pCI vector.

SEAP Assay

Human C33A cells (human epitheial carcenoma—ATTC collection) are seeded in 10 cm tissue culture plates in DMEM+10% fetal calf serum+1× Pen/Strep+1× glutamine+1× NEAA. Cells are grown at 37° C. in a 5% $CO_2$ atmosphere until they reach 50–80% of confluency.

The transient transfection is performed by the $CaPO_4$ method (Sambrook et al., 1989). Thus, expression plasmids for H-ras, N-ras, K-ras, Myr-ras or H-ras-CVLL are co-precipitated with the DSE-SEAP reporter construct. For 10 cm plates 600 µl of $CaCl_2$-DNA solution is added dropwise while vortexing to 600 µl of 2×HBS buffer to give 1.2 ml of precipitate solution (see recipes below). This is allowed to sit at room temperature for 20 to 30 minutes. While the precipitate is forming, the media on the C33A cells is replaced with DMEM (minus phenol red; Gibco cat. #31053–028)+0.5% charcoal stripped calf serum+1× (Pen/Strep, Glutamine and nonessential aminoacids). The $CaPO_4$-DNA precipitate is added dropwise to the cells and the plate rocked gently to distribute. DNA uptake is allowed to proceed for 5–6 hrs at 37° C. under a 5% $CO_2$ atmosphere.

Following the DNA incubation period, the cells are washed with PBS and trypsinized with 1 ml of 0.05% trypsin. The 1 ml of trypsinized cells is diluted into 10 ml of phenol red free DMEM+0.2% charcoal stripped calf serum+1× (Pen/Strep, Glutamine and NEAA). Transfected cells are plated in a 96 well microtiter plate (100 µl/well) to which drug, diluted in media, has already been added in a volume of 100 µl. The final volume per well is 200 µl with each drug concentration repeated in triplicate over a range of half-log steps.

Incubation of cells and drugs is for 36 hrs at 37° C. under $CO_2$. At the end of the incubation period, cells are examined microscopically for evidence of cell distress. Next, 100 µl of media containing the secreted alkaline phosphatase is removed from each well and transferred to a microtube array for heat treatment at 65° C. for 1 hr to inactivate endogenous alkaline phosphatases (but not the heat stable secreted phosphatase).

The heat treated media is assayed for alkaline phosphatase by a luminescence assay using the luminescence reagent CSPD® (Tropix, Bedford, Mass.). A volume of 50 µl media is combined with 200 µl of CSPD cocktail and incubated for 60 minutes at room temperature. Luminesence is monitored using an ML2200 microplate luminometer (Dynatech). Luminescence reflects the level of activation of the fos reporter construct stimulated by the transiently expressed protein.

| $DNA-CaPO_4$ precipitate for 10 cm. plate of cells | |
|---|---|
| Ras expression plasmid (1 µg/µl) | 10 µl |
| DSE-SEAP Plasmid (1 µg/µl) | 2 µl |
| Sheared Calf Thymus DNA (1 µg/µl) | 8 µl |
| 2M $CaCl_2$ | 74 µl |
| $dH_2O$ | 506 µl |

2×HBS Buffer
  280 mM NaCl
  10 mM KCl
  1.5 mM $Na_2HPO_4$ $2H_2O$
  12 mM dextrose
  50 mM HEPES
  Final pH=7.05

| Luminesence Buffer (26 ml) | |
|---|---|
| Assay Buffer | 20 ml |
| Emerald Reagent™ (Tropix) | 2.5 ml |
| 100 mM homoarginine | 2.5 ml |
| CSPD Reagent ® (Tropix) | 1.0 ml |

Assay Buffer
  Add 0.05M $Na_2CO_3$ to 0.05M $NaHCO_3$ to obtain pH 9.5.
  Make 1 mM in $MgCl_2$

Example 64

The processing assays employed are modifications of that described by DeClue et al [Cancer Research 51, 712–717, 1991].

K4B-Ras Processing Inhibition Assay

PSN-1 (human pancreatic carcinoma) or viral-K4B-ras-transformed Rat1 cells are used for analysis of protein processing. Subconfluent cells in 100 mm dishes are fed with 3.5 ml of media (methionine-free RPMI supplemented with 2% fetal bovine serum or cysteine-free/methionine-free DMEM supplemented with 0.035 ml of 200 mM glutamine (Gibco), 2% fetal bovine serum, respectively) containing the desired concentration of test compound, lovastatin or solvent alone. Cells treated with lovastatin (5–10 $\mu$M), a compound that blocks Ras processing in cells by inhibiting a rate-limiting step in the isoprenoid biosynthetic pathway, serve as a positive control. Test compounds are prepared as 1000× concentrated solutions in DMSO to yield a final solvent concentration of 0.1%. Following incubation at 37° C. for two hours 204 $\mu$Ci/ml [$^{35}$S]Pro-Mix (Amersham, cell labeling grade) is added.

After introducing the label amino acid mixture, the cells are incubated at 37° C. for an additional period of time (typically 6 to 24 hours). The media is then removed and the cells are washed once with cold PBS. The cells are scraped into 1 ml of cold PBS, collected by centrifugation (10,000×g for 10 sec at room temperature), and lysed by vortexing in 1 ml of lysis buffer (1% Nonidet P-40, 20 mM HEPES, pH 7.5, 150 mM NaCl, 1 mM EDTA, 0.5% deoxycholate, 0.1% SDS, 1 mM DTT, 10 $\mu$g/ml AEBSF, 10 $\mu$g/ml aprotinin, 2 $\mu$g/ml leupeptin and 2 $\mu$g/ml antipain). The lysate is then centrifuged at 15,000×g for 10 min at 4° C. and the supernatant saved.

For immunoprecipitation of Ki4B-Ras, samples of lysate supernatant containing equal amounts of protein are utilized. Protein concentration is determined by the bradford method utilizing bovine serum albumin as a standard. The appropriate volume of lysate is brought to 1 ml with lysis buffer lacking DTT and 8 $\mu$g of the pan Ras monoclonal antibody, Y13-259, added. The protein/antibody mixture is incubated on ice at 4° C. for 24 hours. The immune complex is collected on pansorbin (Calbiochem) coated with rabbit antiserum to rat IgG (Cappel) by tumbling at 4° C. for 45 minutes. The pellet is washed 3 times with 1 ml of lysis buffer lacking DTT and protease inhibitors and resuspended in 100 $\mu$l elution buffer (10 mM Tris pH 7.4, 1% SDS). The Ras is eluted from the beads by heating at 95° C. for 5 minutes, after which the beads are pelleted by brief centrifugation (15,000×g for 30 sec. at room temperature).

The supernatant is added to 1 ml of Dilution Buffer 0.1% Triton X-100, 5 mM EDTA, 50 mM NaCl, 10 mM Tris pH 7.4) with 2 $\mu$g Kirsten-ras specific monoclonal antibody, c-K-ras Ab-1 (Calbiochem). The second protein/antibody mixture is incubated on ice at 4° C. for 1–2 hours. The immune complex is collected on pansorbin (Calbiochem) coated with rabbit antiserum to rat IgG (Cappel) by tumbling at 4° C. for 45 minutes. The pellet is washed 3 times with 1 ml of lysis buffer lacking DTT and protease inhibitors and resuspended in Laemmli sample buffer. The Ras is eluted from the beads by heating at 95° C. for 5 minutes, after which the beads are pelleted by brief centrifugation. The supernatant is subjected to SDS-PAGE on a 12% acrylamide gel (bis-acrylamide:acrylamide, 1:100), and the Ras visualized by fluorography.

hDJ Processing Inhibition Assay

PSN-1 cells are seeded in 24-well assay plates. For each compound to be tested, the cells are treated with a minimum of seven concentrations in half-log steps. The final solvent (DMSO) concentration is 0.1%. A vehicle-only control is included on each assay plate. The cells are treated for 24 hours at 37° C./5% $CO_2$.

The growth media is then aspirated and the samples are washed with PBS. The cells are lysed with SDS-PAGE sample buffer containing 5% 2-mercaptoethanol and heated to 95° C. for 5 minutes. After cooling on ice for 10 minutes, a mixture of nucleases is added to reduce viscosity of the samples.

The plates are incubated on ice for another 10 minutes. The samples are loaded onto pre-cast 8% acrylamide gels and electrophoresed at 15 mA/gel for 3–4 hours. The samples are then transferred from the gels to PVDF membranes by Western blotting.

The membranes are blocked for at least 1 hour in buffer containing 2% nonfat dry milk. The membranes are then treated with a monoclonal antibody to hDJ-2 (Neomarkers Cat. #MS-225), washed, and treated with an alkaline phosphatase-conjugated secondary antibody. The membranes are then treated with a fluorescent detection reagent and scanned on a phosphorimager.

For each sample, the percent of total signal corresponding to the unprenylated species of hDJ (the slower-migrating species) is calculated by densitometry. Dose-response curves and $EC_{50}$ values are generated using 4-parameter curve fits in SigmaPlot software.

Example 65

Rap1 Processing Inhibition Assay

Protocol A

Cells are labeled, incubated and lysed as described in Example 64.

For immunoprecipitation of Rap1, samples of lysate supernatant containing equal amounts of protein are utilized. Protein concentration is determined by the bradford method utilizing bovine serum albumin as a standard. The appropriate volume of lysate is brought to 1 ml with lysis buffer lacking DTT and 2 $\mu$g of the Rap1 antibody, Rap1/Krev1 (121) (Santa Cruz Biotech), is added. The protein/antibody mixture is incubated on ice at 4° C. for 1 hour. The immune complex is collected on pansorbin (Calbiochem) by tumbling at 4° C. for 45 minutes. The pellet is washed 3 times with 1 ml of lysis buffer lacking DTT and protease inhibitors and resuspended in 100 $\mu$l elution buffer (10 mM Tris pH 7.4, 1% SDS). The Rap1 is eluted from the beads by heating at 95° C. for 5 minutes, after which the beads are pelleted by brief centrifuigation (15,000×g for 30 sec. at room temperature).

The supernatant is added to 1 ml of Dilution Buffer (0.1% Triton X-100, 5 mM EDTA, 50 mM NaCl, 10 mM Tris pH 7.4) with 2 $\mu$g Rap1 antibody, Rap1/Krev1 (121) (Santa Cruz Biotech). The second protein/antibody mixture is incubated on ice at 4° C. for 1–2 hours. The immune complex is collected on pansorbin (Calbiochem) by tumbling at 4° C. for 45 minutes. The pellet is washed 3 times with 1 ml of lysis buffer lacking DTT and protease inhibitors and resuspended in Laemmli sample buffer. The Rap1 is eluted from the beads by heating at 95° C. for 5 minutes, after which the beads are pelleted by brief centrifugation. The supernatant is subjected to SDS-PAGE on a 12% acrylamide gel (bis-acrylamide:acrylamide, 1:100), and the Rap1 visualized by fluorography.

Protocol B

PSN-1 cells are passaged every 3–4 days in 10 cm plates, splitting near-confluent plates 1:20 and 1:40. The day before the assay is set up, $5 \times 10^6$ cells are plated on 15 cm plates to ensure the same stage of confluency in each assay. The media for these cells is RPM1 1640 (Gibco), with 15% fetal bovine serum and 1×Pen/Strep antibiotic mix.

The day of the assay, cells are collected from the 15 cm plates by trypsinization and diluted to 400,000 cells/mil in media. 0.5 ml of these diluted cells are added to each well of 24-well plates, for a final cell number of 200,000 per well. The cells are then grown at 37 C. overnight.

The compounds to be assayed are diluted in DMSO in ½-log dilutions. The range of final concentrations to be assayed is generally 0.1–100 $\mu$M. Four concentrations per compound is typical. The compounds are diluted so that each concentration is 1000× of the final concentration (i.e., for a 10 $\mu$M data point, a 10 mM stock of the compound is needed).

2 $\mu$L of each 1000×compound stock is diluted into 1 ml media to produce a 2×stock of compound. A vehicle control solution (2 $\mu$L DMSO to 1 ml media) is utilized. 0.5 ml of the 2×stocks of compound are added to the cells.

After 24 hours, the media is aspirated from the assay plates. Each well is rinsed with 1 ml PBS, and the PBS is aspirated. 180 $\mu$L SDS-PAGE sample buffer (Novex) containing 5% 2-mercapto-ethanol is added to each well. The plates are heated to 100° C. for 5 minutes using a heat block containing an adapter for assay plates. The plates are placed on ice. After 10 minutes, 20 $\mu$L of an RNAse/DNase mix is added per well. This mix is 1 mg/ml DNaseI (Worthington Enzymes), 0.25 mg/ml Rnase A (Worthington Enzymes), 0.5M Ths-HCl pH8.0 and 50 mM $MgCl_2$. The plate is left on ice for 10 minutes. Samples are then either loaded on the gel, or stored at −70° C. until use.

Each assay plate (usually 3 compounds, each in 4-point titrations, plus controls) requires one 15-well 14% Novex gel. 25 $\mu$l of each sample is loaded onto the gel. The gel is run at 15 mA for about 3.5 hours. It is important to run the gel far enough so that there will be adequate separation between 21 kd (Rap1) and 29 kd (Rab6). The gels are then transferred to Novex pre-cut PVDF membranes for 1.5 hours at 30V (constant voltage). Immediately after transferring, the membranes are blocked overnight in 20 ml Western blocking buffer (2% nonfat dry milk in Western wash buffer (PBS+0.1% Tween-20). If blocked over the weekend, 0.02% sodium azide is added. The membranes are blocked at 4° C. with slow rocking.

The blocking solution is discarded and 20 ml fresh blocking solution containing the anti Rap1a antibody (Santa Cruz Biochemical SC1482) at 1:1000 (diluted in Western blocking buffer) and the anti Rab6 antibody (Santa Cruz Biochemical SC310) at 1:5000 (diluted in Western blocking buffer) are added. The membranes are incubated at room temperature for 1 hour with mild rocking. The blocking solution is then discarded and the membrane is washed 3 times with Western wash buffer for 15 minutes per wash. 20 ml blocking solution containing 1:1000 (diluted in Western blocking buffer) each of two alkaline phosphatase conjugated antibodies (Alkaline phosphatase conjugated Anti-goat IgG and Alkaline phosphatase conjugated anti-rabbit IgG [Santa Cruz Biochemical]) is then added. The membrane is incubated for one hour and washed 3× as above.

About 2 ml per gel of the Amersham ECF detection reagent is placed on an overhead transparency (ECF) and the PVDF membranes are placed face-down onto the detection reagent. This is incubated for one minute, then the membrane is placed onto a fresh transparency sheet.

The developed transparency sheet is scanned on a phosphorimager and the Rap1a Minimum Inhibitory Concentration is determined from the lowest concentration of compound that produces a detectable Rap1a Western signal. The Rap1a antibody used recognizes only unprenylated/unprocessed Rap1a, so that the precence of a detectable Rap1a Western signal is indicative of inhibition of Rap1a prenylation.

Protocol C

This protocol allows the determination of an $EC_{50}$ for inhibition of processing of Rap1a. The assay is run as described in Protocol B with the following modifications. 20 $\mu$l of sample is run on pre-cast 10–20% gradient acrylamide mini gels (Novex Inc.) at 15 mA/gel for 2.5–3 hours. Prenylated and unprenylated forms of Rap1a are detected by blotting with a polyclonal antibody (Rap1/Krev-1 Ab#121;Santa Cruz Research Products #sc-65), followed by an alkaline phosphatase-conjugated anti-rabbit IgG antibody. The percentage of unprenylated Rap1a relative to the total amount of Rap1a is determined by peak integration using Imagequant6 software (Molecular Dynamics). Unprenylated Rap1a is distinguished from prenylated protein by virtue of the greater apparent molecular weight of the prenylated protein. Dose-response curves and $EC_{50}$ values are generated using 4-parameter curve fits in SigmaPlot software.

Example 66

In vivo Tumor Growth Inhibition Assay (Nude Mouse)

In vivo efficacy as an inhibitor of the growth of cancer cells may be confirmed by several protocols well known in the art. Examples of such in vivo efficacy studies are described by N. E. Kohl et al. (Nature Medicine, 1:792–797 (1995)) and N. E. Kohl et al. (Proc. Nat. Acad. Sci. U.S.A., 91:9141–9145 (1994)).

Rodent fibroblasts transformed with oncogenically mutated human Ha-ras or Ki-ras ($10^6$ cells/animal in 1 ml of DMEM salts) are injected subcutaneously into the left flank of 8–12 week old female nude mice (Harlan) on day 0. The mice in each oncogene group are randomly assigned to a vehicle, compound or combination treatment group. Animals are dosed subcutaneously starting on day 1 and daily for the duration of the experiment. Alternatively, the farnesyl-protein transferase inhibitor may be administered by a continuous infusion pump. Compound, compound combination or vehicle is delivered in a total volume of 0.1 ml. Tumors are excised and weighed when all of the vehicle-treated animals exhibited lesions of 0.5–1.0 cm in diameter, typically 11–15 days after the cells were injected. The average weight of the tumors in each treatment group for each cell line is calculated.

What is claimed is:

1. A compound of the formula B which is:

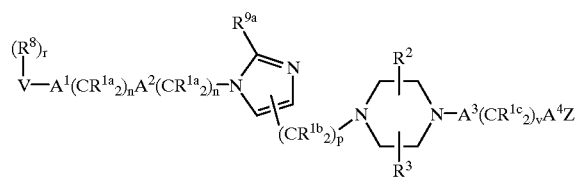

B wherein:

$R^{1a}$ and $R^{1b}$ are independently selected from:
  a) hydrogen,
  b) aryl, heterocycle, cycloalkyl, CN, $R^{10}O-$, $R^{10}NC(O)-$, $-N(R^{10})_2$ or $C_2-C_6$ alkenyl,
  c) $C_1-C_6$ alkyl unsubstituted or substituted by aryl, heterocycle, cycloalkyl, alkenyl, $R^{10}O-$, or $-N(R^{10})_2$;

$R^{1c}$ is independently selected from:
  a) hydrogen,
  b) $C_3-C_{10}$ cycloalkyl, $R^{10}O-$, $R^{10}C(O)NR^{10}-$, $(R^{10})_2NC(O)-$, $R^{10}_2N-C(NR^{10})-$, CN, $NO_2$, $R^{10}C(O)-$, $N_3$, $-N(R^{10})_2$ or $R^{11}OC(O)NR^{10}-$,
  c) unsubstituted or substituted $C_1-C_6$ alkyl wherein the substituent on the substituted $C_1-C_6$ alkyl is selected from $R^{10}O-$, $R^{10}C(O)NR^{10}-$, $(R^{10})_2NC(O)-$, $R^{10}_2N-C(NR^{10})-$, CN, $R^{10}C(O)-$, $N_3$, $-N(R^{10})_2$ and $R^{11}OC(O)-NR^{10}-$; or two $R^{1c}$s on the same carbon are combined with that carbon to form a $C_4-C_6$ cycloalkyl or $C_6-C_{10}$ multicyclic alkyl ring;

$R^3$ is selected from H a $CH_3$;
$R^2$ is selected from H;

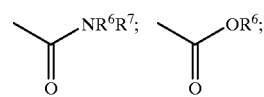

or $C_{1-5}$ alkyl, unbranched or branched, unsubstituted or substituted with one or more of:

1) aryl,
  2) heterocycle,
  3) $OR^6$,
  4) $SR^{6a}$, $SO_2R^{6a}$, or
  5)

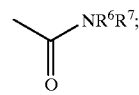

and $R^2$ and $R^3$ are optionally attached to the same carbon atom;

$R^6$ and $R^7$ are independently selected from: H; $C_{1-4}$ alkyl, $C_{3-6}$ cycloalkyl, aryl, heterocycle, unsubstituted or substituted with:
  a) $C_{1-4}$ alkoxy,
  b) halogen, or
  c) aryl or heterocycle;

$R^{6a}$ is selected from: $C_{1-4}$ alkyl or $C_{3-6}$ cycloalkyl, unsubstituted or substituted with:
  a) $C_{1-4}$ alkoxy,
  b) halogen, or
  c) aryl or heterocycle;

$R^8$ is independently selected from:
  a) hydrogen,
  b) $C_1-C_6$ alkyl, $C_2-C_6$ alkenyl, $C_2-C_6$ alkynyl, $C_1-C_6$ perfluoroalkyl, F, Cl, $R^{10}O-$, $R^{10}C(O)NR^{10}-$, CN, $NO_2$, $(R^{10})_2N-C(NR^{10})-$, $R^{10}C(O)-$, $-N(R^{10})_2$, or $R^{11}OC(O)NR^{10}-$, and
  c) $C_1-C_6$ alkyl substituted by $C_1-C_6$ perfluoroalkyl, $R^{10}O-$, $R^{10}C(O)NR^{10}-$, $(R^{10})_2N-C(NR^{10})-$, $R^{10}C(O)-$, $-N(R^{10})_2$, or $R^{11}C(O)NR^{10}-$;

$R^{9a}$ is hydrogen, $C_1-C_6$ alkyl or chloro;
$R^{10}$ is independently selected from hydrogen, $C_1-C_6$ alkyl, benzyl and aryl;
$R^{11}$ is independently selected from $C_1-C_6$ alkyl and aryl;
$A^1$ and $A^2$ are independently selected from: a bond, $-CH=CH-$, $-C\equiv C-$, $-C(O)-$, $-C(O)NR^{10}-$, $O$, $-N(R^{10})-$, or $S(O)_m$;
$A^3$ is selected from: $-C(O)-$, $-C(O)NR^{10}-$, $-C(O)O-$ and $S(O)_m$;
$A^4$ is selected from: a bond, O, and $NR_{10}$;

V is selected from:
  a) hydrogen,
  b) heterocycle selected from pyrrolidinyl, imidazolyl, pyridinyl, thiazolyl, pyridonyl, 2-oxopiperidinyl, indolyl, quinolinyl, isoquinolinyl, and thienyl,
  c) aryl,
  d) $C_1$–$C_{20}$ alkyl wherein from 0 to 4 carbon atoms are replaced with a heteroatom selected from O, S, and N, and
  e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

Z is unsubstituted or substituted aryl or unsubstituted or substituted heteroaryl;

m is 0, 1 or 2;

n is 0, 1, 2, 3 or 4;

p is 0, 1, 2, 3 or 4;

r is 0 to 5, provided that r is 0 when V is hydrogen; and v is 0, 1, 2 or 3; provided that v is not 0 if $A^3$ is —C(O)— or $S(O)_m$;

or the pharmaceutically acceptable salts thereof.

2. The compound according to claim 1 of the formula D:

$$D$$

wherein:

$R^{1a}$ and $R^{1b}$ are independently selected from:
  a) hydrogen,
  b) aryl, heterocycle, cycloalkyl, CN, $R^{10}O$—, $R^{10}NC(O)$—, —$N(R^{10})_2$ or $C_2$–$C_6$ alkenyl,
  c) $C_1$–$C_6$ alkyl unsubstituted or substituted by aryl, heterocycle, cycloalkyl, alkenyl, $R^{10}O$—, or —$N(R^{10})_2$;

$R^{1c}$ is independently selected from:
  a) hydrogen,
  b) $C_3$–$C_{10}$ cycloalkyl, $R^{10}O$—, $R^{10}C(O)NR^{10}$—, $(R^{10})_2NC(O)$—, $R^{10}_2N$—$C(NR^{10})$—, CN, $NO_2$, $R^{10}C(O)$—, $N_3$, —$N(R^{10})_2$ or $R^{11}OC(O)NR^{10}$—,
  c) unsubstituted or substituted $C_1$–$C_6$ alkyl wherein the substituent on the substituted $C_1$–$C_6$ alkyl is selected from $R^{10}O$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$ and $R^{11}OC(O)$—$NR^{10}$—;or two $R^{1c}$s on the same carbon are combined with that carbon to form a $C_4$–$C_6$ cycloalkyl or $C_6$–$C_{10}$ multicyclic alkyl ring;

$R^3$ is selected from H and $CH_3$;

$R^2$ is selected from H;

$$\overset{NR^6R^7;}{\underset{O}{\|}} \quad \overset{OR^6;}{\underset{O}{\|}}$$

or $C_{1-5}$ alkyl, unbranched or branched, unsubstituted or substituted with one or more of:

1) aryl,
  2) heterocycle,
  3) $OR^6$,
  4) $SR^{6a}$, $SO_2R^{6a}$, or
  5)

$$\overset{NR^6R^7;}{\underset{O}{\|}}$$

and $R^2$ and $R^3$ are optionally attached to the same carbon atom;

$R^6$ and $R^7$ are independently selected from: H; $C_{1-4}$ alkyl, $C_{3-6}$ cycloalkyl, aryl, heterocycle, unsubstituted or substituted with:
  a) $C_{1-4}$ alkoxy,
  b) halogen, or
  c) aryl or heterocycle;

$R^{6a}$ is selected from: $C_{1-4}$ alkyl or $C_{3-6}$ cycloalkyl, unsubstituted or substituted with:
  a) $C_{1-4}$ alkoxy,
  b) halogen, or
  c) aryl or heterocycle;

$R^8$ is independently selected from:
  a) hydrogen,
  b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
  c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

$R^{9a}$ is hydrogen, $C_1$–$C_6$ alkyl or chloro;

$R^{10}$ is independently selected from hydrogen, $C_1$–$C_6$ alkyl, benzyl and aryl;

$R^{11}$ is independently selected from $C_1$–$C_6$ alkyl and aryl;

$A^1$ is selected from: a bond, —CH=CH—, —C≡C—, —C(O)—, —C(O)NR^{10}—, O, —N(R^{10})—, or $S(O)_m$;

$A^3$ is selected from: —C(O)—, —C(O)NR^{10}—, —C(O)O— and $S(O)_m$;

V is selected from:
  a) heterocycle selected from pyridinyl and quinolinyl, and
  b) aryl;

Z is unsubstituted or substituted aryl or unsubstituted or substituted heteroaryl;

m is 0, 1 or 2;

n is 0, 1, 2, 3 or 4;

p is 0, 1, 2, 3 or 4;

r is 0 to 5, and v is 0, 1, 2 or 3; provided that v is not 0 if $A^3$ is —C(O)— or $S(O)_m$;

or the pharmaceutically acceptable salts thereof.

3. A compound which is selected from:

1-[1-(4'-Cyanobenzyl)imidazol-5-ylmethyl]-4-[1-phenyl-1-cyclopentylcarbonyl]piperazine 1-[1-(4'-Cyanobenzyl)imidazol-5-ylmethyl]-4-[Cyclohexylphenylacetyl]piperazine 1-[1-(4'-Cyanobenzyl)imidazol-5-ylmethyl]-4-[1-(3-methoxyphenyl)-1-cyclopentylcarbonyl]piperazine 1-[1-(4'-Cyanobenzyl)imidazol-5-ylmethyl]-4-[1-(3-phenoxyphenyl)-1-cyclopentylcarbonyl]piperazine 1-[1-(4'-Cyano-3-fluorobenzyl)imidazol-5-ylmethyl]-4-[1-(3-hydroxyphenyl)-1-cyclohexylcarbonyl]piperazine 1-[1-(4'-Cyanobenzyl)imidazol-5-ylmethyl]piperazine-4-carboxylic acid-(2,6-dimethoxy)benzyl ester
1-[1-(4'-Cyanobenzyl)imidazol-5-ylmethyl]piperazine-4-(DL-2-hydroxy-2-(o-methoxyphenyl))acetamide
1-[1-(4'-Cyanobenzyl)imidazol-5-ylmethyl]-4-[1-(2,6-dimethylbenzyloxycarbonyl]piperazine
1-[1-(4'-Cyanobenzyl)imidazol-5-ylmethyl]-4-[1-(2-methoxyphenyl)-1-cyclopentylcarbonyl]piperazine
(±) 1-[1-(4'-Cyanobenzyl)imidazol-5-ylmethyl]-4-[1-(bicyclo[3.1.0]hex-3-yl)-1-(3-methoxyphenyl)-carbonyl]piperazine
(R/S) 2-[4-((Phenyl)methyloxycarbonyl-1-piperazine)]-2-[1-(4'-cyanobenzyl)-2-methyl-5-imidazol]acetonitrile
1-[1-(4'-methylbenzyl)imidazol-5-ylmethyl]-4-[1-(2,6-dimethylbenzyloxycarbonyl]piperazine
1-[1-(4'-Cyanobenzyl)imidazol-5-ylmethyl]piperazine-4-carboxylic acid-(4-nitro)phenyl ester
1-[1-(4-Cyanobenzyl)imidazol-5-ylmethyl]-4-[3-(4-fluorophenyl)-3-(tricyclo[3.3.1.1$^{3,7}$]dec-2-yl)-propionyl]piperazine
2-(1-(4'-cyanobenzyl)imidazol-5-yl)-2-[4-(phenylmethyloxy carbonyl)piperazin-1-yl]acetamide
1-[1-(4'-cyanobenzyl)imidazol-5-ylmethyl]-4-[1-(2-methoxy-5-chlorobenzyloxycarbonyl]piperazine
1-[1-(4'-cyanobenzyl)imidazol-5-ylmethyl]-4-[1-(pentafluororobenzyloxycarbonyl]piperazine
1-[1-(4'-cyanobenzyl)imidazol-5-ylmethyl]-4-[1-(2-ethoxybenzyloxycarbonyl]piperazine
1-[1-(4'-cyanobenzyl)imidazol-5-ylmethyl]-4-{1-[(2-methoxypyridin-3-yl)methyloxycarbonyl]}piperazine
1-[1-(4'-cyanobenzyl)imidazol-5-ylmethyl]-4-[1-(2-trifluoromethoxybenzyloxycarbonyl]piperazine
1-[1-(4'-cyanobenzyl)imidazol-5-ylmethyl]-4-[1-(2,3-methylenedioxybenzyloxycarbonyl]piperazine
1-[1-(4'-Cyanobenzyl)imidazol-5-ylmethyl]piperazine-4-carboxylic acid benzyl ester
1-[1-(4'-Cyanobenzyl)imidazol-5-ylmethyl]-piperazine-3-carboxylic acid-4-carboxylic acid benzyl ester
1-[1-(4'-Cyanobenzyl)imidazol-5-ylmethyl]-3-methyl carboxy-piperazine-4-carboxylic acid benzyl ester
1-[1-(4'-Cyanobenzyl)imidazol-5-ylmethyl]piperazine-4-(N-3-isopropenyl-1,1-dimethylbenzyl)carboxamide
1-[1-(4'-cyanobenzyl)imidazol-5-ylmethyl]-4-phenylmethanesulfonyl-(cis)-2,6-dimethylpiperazine
2-(1-(4'-cyanobenzyl)-5-imidazolyl))-2-[(4'-phenylmethyloxycarbonyl)piperazin-1'-yl]acetonitrile
1-[1-(4'-Cyanobenzyl)imidazol-5-ylmethyl]-4-(2-tert-butyl-3-phenyl)propionyl piperazine
1-[1-(4-Cyanobenzyl)imidazol-5-ylmethyl]-4-[1-(4-methoxyphenyl)-1-cyclohexyl]carbonyl piperazine
1-[1-(4'-Cyanobenzyl)imidazol-5-ylmethyl]-4-{1-[(2-ethoxypyridin-3-yl)methyloxycarbonyl]piperazine
1-[1-(4'-Cyanobenzyl)imidazol-5-ylmethyl]-4-1-(2-methanesulfonylbenzyloxycarbonyl)piperazine
1-[1-(4'-Cyanobenzyl)imidazol-5-yl)-piperazine-4-(N-(2-(ethoxybenzyl)carbamide)
1-[1-(4'-Cyanobenzyl)-2-methyl)imidazol-5-yl)-4-(benzyloxycarbonyl)]piperazine
1-[1-(4'-Cyanobenzyl)imidazol-5-ylmethyl]piperazine-4-(N-3-methylbenzyl)carboxamide
1-[1-(4'-Cyanobenzyl)imidazol-5-ylmethyl]piperazine-4-(N-2-chlorobenzyl)carboxamide
1-[1-(4-Cyanobenzyl)imidazol-5-yl)]piperazine-4-(N-2-methoxybenzyl)carboxamide
1-[1-(4-Cyanobenzyl)imidazol-5-yl]piperazine-4-(N-3-methoxy-6-chlorobenzyl)carboxamide
1-[1-(4'-Cyanobenzyl)imidazol-5-yl]piperazine-4-(N-(2-methyl-5-chlorobenzyl))carboxamide
1-[1-(4-Cyanobenzyl)imidazol-5-yl]piperazine-4-(N-(3-phenylpropyl))carboxamide
1-[1-(4'-Cyanobenzyl)imidazol-5-yl]piperazine-4-(N-(2,5-dimethylbenzyl))carbamide
1-[1-(4'-Cyanobenzyl)imidazole-5-ylmethyl]-4-benzyloxycarbonyl)-(trans)-2,5-dimethylpiperazine
1-[(4-cyanophenyl)methylimidazol-5-ylmethyl]piperazine-4-2,4-dimethylbenzyloxycarbonyl
1-[1-(4-cyanophenyl)methylimidazol-5-ylmethyl]piperazine-4-(2-methylbenzyloxycarbonyl)
1-[1-(4-cyanophenyl)methylimidazol-5-ylmethyl]piperazine-4-(4'-acetamidobenzyloxycarbonyl)
1-[1-(4-cyanophenyl)methylimidazol-5-ylmethyl]piperazine-4-[(3'-methylbenzyloxycarbonyl)
1-[1-(4-cyanophenyl)methylimidazol-5-ylmethyl]piperazine-4-(2'-methoxybenzyloxycarbonyl)
1-[1-(4-cyanophenyl)methylimidazol-5-ylmethyl]piperazine-4-(3'-methoxybenzyloxycarbonyl)
1-[1-(4-cyanophenyl)methylimidazol-5-ylmethyl]piperazine-4-(1-oxypyridine-3-methyloxycarbonyl)
1-[1-(4-cyanophenyl)methylimidazol-5-ylmethyl]piperazine-4-(3-pyridinemethyloxycarbonyl)
1-[1-(4-cyanophenyl)methylimidazol-5-ylmethyl]piperazine-4-(4'-pyridinemethyloxycarbonyl)
1-[1-(4-cyanophenyl)methylimidazol-5-ylmethyl]piperazine-4-(2',5'-dimethylbenzyloxycarbonyl)
1-[1-(4-cyanophenyl)methylimidazol-5-ylmethyl]piperazine-4-[(1,3-benzodioxolan-5-methyl)oxycarbonyl]
1-[1-(4-cyanobenzyl)-2-methylimidazol-5-ylmethyl]-4-[2-ethoxybenzyloxycarbonyl]piperazine
1-[1-(4-cyanobenzyl)-2-methylimidazol-5-ylmethyl]-4-[2-(trifluoromethoxy)benzyloxycarbonyl]piperazine
1-[1-(4-cyanobenzyl)-2-methylimidazol-5-ylmethyl]-4-[2,3-(difluoromethylenedioxy)benzyloxycarbonyl]piperazine
1-[1-(4-cyanobenzyl)-2-methylimidazol-5-ylmethyl]-4-[3-ethoxybenzyloxy)carbonyl]piperazine
1-[1-(4-cyanobenzyl)-2-methylimidazol-5-ylmethyl]-4-[2-(difluoromethoxy)benzyloxycarbonyl]piperazine
1-[1-(4-cyanobenzyl)-2-methylimidazol-5-ylmethyl]-4-[2-(trifluoromethyl)benzyloxycarbonyl]piperazine
1-[1-(4-cyanobenzyl)-2-methylimidazol-5-ylmethyl]-4-[2-(difluoromethoxy)-5-methylbenzyloxycarbonyl]piperazine
1-[1-(4-cyanobenzyl)-2-methylimidazol-5-ylmethyl]-4-[2-(triflurormethylsulfonyl)benzyloxycarbonyl]piperazine
(±)-1-[1-(4-cyanobenzyl)-2-methylimidazol-5-ylmethyl]-4-[2-(triflurormethylsulfoxy)benzyloxycarbonyl]piperazine
1-[1-(4-cyanobenzyl)-2-methylimidazol-5-ylmethyl]-4-[2-(triflurormethylthio)benzyloxycarbonyl]piperazine
1-[1-(4'-Cyanobenzyl)imidazole-5-ylmethyl]-4-[2-(2,2,2-trifluoroethoxy)benzyloxycarbonyl]piperazine
(R/S) 2-[4-((2-ethoxyphenyl)methyloxycarbonyl-1-piperazine)]-2-[1-(4-cyanobenzyl)-2-methyl-5-imadazol]acetonitrile
1-[1-(4'-Cyanobenzyl)-2-methyl-imidazol-5-ylmethyl]piperazine-4-(N-2-trifluoromethoxybenzyl)carboxamide
1-[1-(4'-Cyanobenzyl)-2-methyl-imidazol-5-ylmethyl]piperazine-4-{N-[2-(3-trifluoromethylphenyl)ethyl]}carboxamide
1-[1-(4'-Cyanobenzyl)-2-methyl-imidazol-5-ylmethyl]piperazine-4-N-(2-fluoro-5-trifluoromethylbenzyl)carboxamide
1-[1-(4'-Cyanobenzyl)-2-methyl imidazol-5-ylmethyl]piperazine-4-carboxylic acid-(2-fluoro-3-trifluoromethyl)benzyl ester or the pharmaceutically acceptable salts or optical isomers thereof.

4. The compound according to claim 3 which is:
1-[1-(4'-Cyanobenzyl)imidazol-5-ylmethyl]piperazine-4-carboxylic acid-(2,6-dimethoxy)benzyl ester

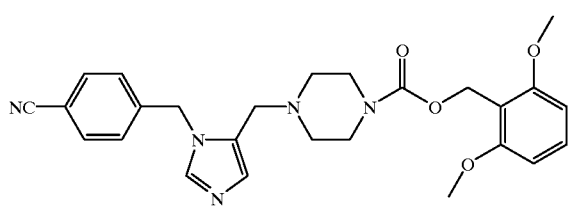

or the pharmaceutically acceptable salts or optical isomers thereof.

5. The compound according to claim 3 which is:
1-[1-(4'-Cyanobenzyl)imidazol-5-ylmethyl]-4-[1-(2,6-dimethylbenzyloxycarbonyl]piperazine

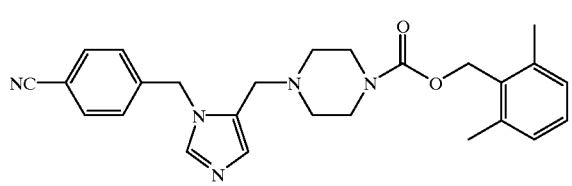

or the pharmaceutically acceptable salts or optical isomers thereof.

6. The compound according to claim 3 which is:
1-[1-(4'-methylbenzyl)imidazol-5-ylmethyl]-4-[1-(2,6-dimethylbenzyloxycarbonyl]piperazine

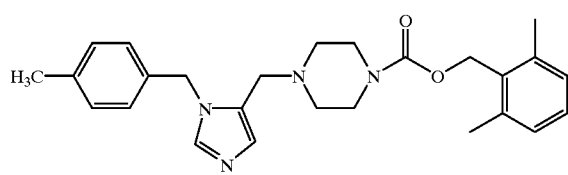

or the pharmaceutically acceptable salts or optical isomers thereof.

7. The compound according to claim 3 which is:
1-[1-(4'-cyanobenzyl)imidazol-5-ylmethyl]-4-[1-(2-ethoxybenzyloxycarbonyl]piperazine

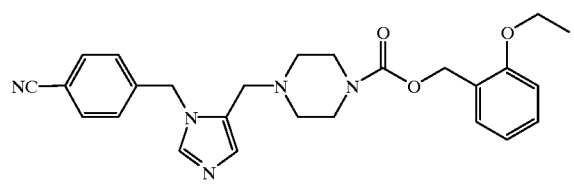

or the pharmaceutically acceptable salts or optical isomers thereof.

8. The compound according to claim 3 which is:
1-[1-(4'-Cyanobenzyl)imidazol-5-yl)-2-(ethoxybenzyl)]piperazine-4-carbamide

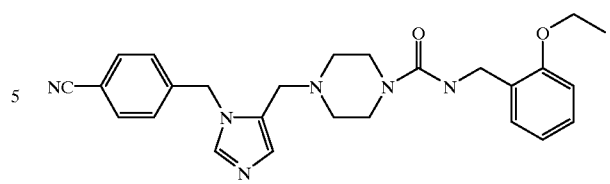

or the pharmaceutically acceptable salts or optical isomers thereof.

9. The compound according to claim 3 which is:
1-[1-1-(4'-Cyanobenzyl)imidazol-5-ylmethyl]-4-{1-[(2-ethoxypyridin-3-yl)methyloxycarbonyl]piperazine

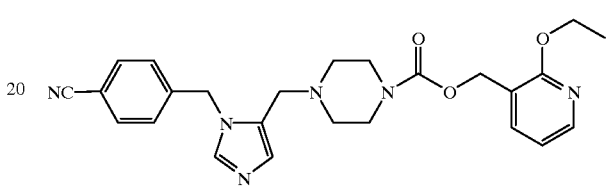

or the pharmaceutically acceptable salts or optical isomers thereof.

10. A pharmaceutically composition comprising a pharmaceutical carrier, and dispersed therein, a therapeutically effective amount of a compound of claim 1.

11. A pharmaceutical composition comprising a pharmaceutical carrier, and dispersed therein, a therapeutically effective amount of a compound of claim 3.

12. A method for treating cancer related to or caused by mutations in the ras gene, or mutations in the proteins that can regulate Ras activity, which comprises administering to a mammal in need thereof a therapeutically effective amount of a composition of claim 10.

13. A method according to claim 12 wherein the cancer is characterized by a mutated K4B-Ras protein.

14. A method for treating cancer related to or caused by mutations in the ras gene, or mutations in the proteins that can regulate Ras activity, which comprises administering to a mammal in need thereof a therapeutically effective amount of a composition of claim 11.

15. A method according to claim 14 wherein the cancer is characterized by a mutated K4B-Ras protein.

16. A method for treating neurofibromin benign proliferative disorder which comprises administering to a mammal in need thereof a therapeutically effective amount of a composition of claim 10.

17. A method for treating blindness related to retinal vascularization which comprises administering to a mammal in need thereof a therapeutically effective amount of a composition of claim 10.

18. A method for treating infections from hepatitis delta which comprises administering to a mammal in need thereof a therapeutically effective amount of a composition of claim 10.

19. A method for preventing restenosis which comprises administering to a mammal in need thereof a therapeutically effective amount of a composition of claim 10.

20. A method for treating polycystic kidney disease which comprises administering to a mammal in need thereof a therapeutically effective amount of a composition of claim 10.

21. A pharmaceutical composition made by combining the compound of claim 1 and a pharmaceutically acceptable carrier.

22. A process for making a pharmaceutical composition comprising combining a compound of claim 1 and a pharmaceutically acceptable carrier.

* * * * *